(12) United States Patent
Taylor

(10) Patent No.: US 8,633,211 B2
(45) Date of Patent: Jan. 21, 2014

(54) BICYCLIC ORGANIC COMPOUNDS SUITABLE FOR THE TREATMENT OF INFLAMMATORY OR ALLERGIC CONDITIONS

(75) Inventor: Roger John Taylor, Horsham (GB)

(73) Assignee: Novartis AG, Basel (CH)

( * ) Notice: Subject to any disclaimer, the term of this patent is extended or adjusted under 35 U.S.C. 154(b) by 867 days.

(21) Appl. No.: 12/449,537

(22) PCT Filed: Mar. 4, 2008

(86) PCT No.: PCT/EP2008/052614
§ 371 (c)(1),
(2), (4) Date: Aug. 11, 2009

(87) PCT Pub. No.: WO2008/107436
PCT Pub. Date: Sep. 12, 2008

(65) Prior Publication Data
US 2010/0113774 A1 May 6, 2010

(30) Foreign Application Priority Data

Mar. 6, 2007 (EP) .................................... 07103600

(51) Int. Cl.
*A61K 31/517* (2006.01)
*C07D 239/80* (2006.01)
*A61P 29/00* (2006.01)

(52) U.S. Cl.
USPC .................... 514/266.3; 544/283; 544/285

(58) Field of Classification Search
USPC ................................ 544/285, 283; 514/266.3
See application file for complete search history.

(56) References Cited

U.S. PATENT DOCUMENTS

| | | | | |
|---|---|---|---|---|
| 4,268,511 A | * | 5/1981 | Baronnet et al. | 514/234.5 |
| 4,299,833 A | * | 11/1981 | Philippossian et al. | 514/263.34 |
| 6,803,129 B2 | * | 10/2004 | Lin et al. | 428/690 |
| 6,924,295 B2 | * | 8/2005 | Tajima et al. | 514/311 |
| 2012/0009172 A1 | * | 1/2012 | Gretler et al. | 424/94.5 |

FOREIGN PATENT DOCUMENTS

| | | | |
|---|---|---|---|
| BE | 882223 | * | 9/1980 |
| EP | 995742 | | 4/2000 |
| FR | 2436781 | * | 4/1980 |
| JP | A-64-025767 | | 1/1989 |
| WO | WO 96/20710 | | 7/1996 |
| WO | WO 98/52948 | | 11/1998 |
| WO | WO 00/58305 | | 10/2000 |
| WO | WO 02/064572 | | 8/2002 |
| WO | WO 02/064752 | | 8/2002 |
| WO | WO 2004/007469 | | 1/2004 |
| WO | WO 2004/014381 | | 2/2004 |
| WO | WO 2005037779 | * | 4/2005 |

OTHER PUBLICATIONS

Qu, et al., Pubmed ID :22547907, May 1, 2012.*
Cordts, et al., Life Sciences, vol. 89, Issues 21-22, Nov. 21, 2011, 806-811.*
Lai, et al., Biosci Rep., Apr. 2011; 31(2):145-50.*
Inoki, et al., Biochem. & Biophys. Research Commun., 346 (2006) 293-300.*
Honess, et al., Radiotherapy and Oncology (1993), 28(3), 208-18.*
Maslankiewicz, et al., Acta Poloniae Pharmaceutica (1979), 36(5), 539-43.*
Dreyer, et al., Phytochemistry (Elsevier) (1980), 19(5), 935-9.*
Kellermann, Archiv fuer Verdauungs-Krankheiten Stoffwechselpathologie und Diaetetik (1931), 50, 335-50.*
Bollettino Chimico Farmaceutico (1914), 53, 70.*
Database Caplus, Chemical Abstracts Service XP00245847—Database Accession No. 1989:497274 abstract & JP 01 025767.
El-Helby et al., "Synthesis and Anticonvulsant Activity of 1,3-Disubstituted 2,4(1H,3H)Quinazolinedione" *Bull. Pharm Sci. Assuit Univ* 28:45-56, 2005.
El-Tamany et al., "Synthesis and Antimicrobial Activities of Some Quinazolinone Derivatives" *Egypt J. Chem.* 40:339-511, 1997.

* cited by examiner

*Primary Examiner* — James O Wilson
*Assistant Examiner* — Cecilia M Jaisle
(74) *Attorney, Agent, or Firm* — Michael G. Smith

(57) ABSTRACT

A compound of formula (I): in free or salt form, wherein A, $R^1$, $R^3$, $Q^a$, $Q^b$ and Q are as defined herein, for the treatment of a disease mediated by the S1P2 or S1P3 receptor, such as inflammatory or obstructive airways disease.

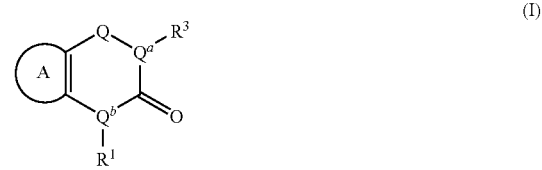

(I)

8 Claims, No Drawings

BICYCLIC ORGANIC COMPOUNDS SUITABLE FOR THE TREATMENT OF INFLAMMATORY OR ALLERGIC CONDITIONS

The present invention relates to organic compounds, their preparation and their use as pharmaceuticals.

In a first aspect, the present invention provides compounds of formula (I):

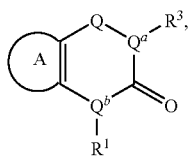

in free or salt form, wherein

Q is selected from $CH_2$, C(O), and C(S);

$Q^a$ and $Q^b$ are independently selected from N and CH;

is selected from $C_6$-$C_{15}$-aromatic carbocyclic group, $C_5$-$C_{15}$-carbocyclic group, and a 4- to 15-membered heterocyclic group having one or more heteroatoms selected from the group consisting of oxygen, nitrogen and sulphur;

$R^1$ is selected from $C_1$-$C_8$-alkyl optionally substituted by —OH, halogen, CN, O—$C_1$-$C_8$-alkyl, $NR^{1c}R^{1d}$, carboxy-$C_1$-$C_8$-alkyl, and COOH, —C($R^{1a}R^{1b}$)$_m$C(O)C$R^{1c}R^{1d}R^{1e}$, —C($R^{1a}R^{1b}$)$_m$C(O)N$R^{1c}R^{1d}$, —C($R^{1a}R^{1b}$)$_t$N$R^{1c}R^{1d}$, C($R^{1a}R^{1b}$)$_m$C$R^{1c}R^{1d}R^{1e}$, C($R^{1a}R^{1b}$)$_m$SO$_2R^{1f}$, C($R^{1a}R^{1b}$)$_m$SOR$^{1g}$, and C($R^{1a}R^{1b}$)$_m$SR$^{1h}$;

$R^{1f}$, $R^{1g}$ and $R^{1h}$ are independently selected from $C_1$-$C_8$-alkyl, $C_1$-$C_8$-hydroxyalkyl, $C_1$-$C_8$-allylamino($C_1$-$C_8$-alkyl), di($C_1$-$C_8$-alkyl)amino($C_1$-$C_8$-alkyl), $C_1$-$C_8$-cyanoalkyl, $C_6$-$C_{15}$-aromatic carbocyclic group, a $C_3$-$C_{15}$-carbocyclic group, $C_1$-$C_8$-haloalkyl and a 4- to 10-membered heterocyclic group having one or more heteroatoms selected from the group consisting of oxygen, nitrogen and sulphur;

each $R^{1a}$ and $R^{1b}$ are independently selected from H, —OH, and $C_1$-$C_8$-alkyl optionally substituted by —OH and halogen;

$R^{1c}$ and $R^{1d}$ are independently selected from H;

$C_6$-$C_{15}$-aromatic carbocyclic group, $C_7$-$C_{15}$-aralkyl, $C_3$-$C_{15}$-carbocyclic group, a 4- to 15-membered heterocyclic group having one or more heteroatoms selected from the group consisting of oxygen, nitrogen and sulphur;

$C_1$-$C_8$-alkoxy optionally substituted by OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$C_2$-$C_8$-alkenyl optionally substituted by —OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$C_2$-$C_8$-alkynyl optionally substituted by —OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur; and $C_1$-$C_8$-alkyl optionally substituted by —OH, —CN, halogen, $NR^4R^5$, $C_1$-$C_8$-alkoxycarbonyl, COOH, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$R^{1e}$ is selected from H and $C_1$-$C_8$-alkyl;

$R^3$ is selected from $C_6$-$C_{15}$-aromatic carbocyclic group optionally substituted by —C($R^{3a}R^{3b}$)$_n$C(O)N$R^{3c}R^{3d}$ or —C($R^{3a}R^{3b}$)$_n$C(O)OH, a $C_7$-$C_{15}$-aralkyl, $C_1$-$C_8$-alkyl substituted by a $C_3$-$C_{15}$-carbocyclic group, a $C_3$-$C_{15}$-carbocyclic group, a 4- to 15-membered heterocyclic group having one or more heteroatoms selected from the group consisting of oxygen, nitrogen and sulphur, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, —C($R^{3a}R^{3b}$)$_n$C(O)N$R^{3c}R^{3d}$ and —C($R^{3a}R^{3b}$)$_n$C(O)OH;

$R^{3a}$ and $R^{3b}$ are independently selected from H, —OH, and $C_1$-$C_8$-alkyl optionally substituted by —OH and halogen;

$R^{3c}$ and $R^{3d}$ are independently selected from H, $C_6$-$C_{15}$-aromatic carbocyclic group, $C_3$-$C_{15}$-carbocyclic group, or $R^{3c}$ and $R^{3d}$, together with the N that they are attached, form a 4- to 15-membered heterocyclic group having one or more heteroatoms selected from the group consisting of oxygen, nitrogen and sulphur, a 4- to 15-membered heterocyclic group having one or more heteroatoms selected from the group consisting of oxygen, nitrogen and sulphur, $C_1$-$C_8$-alkoxy optionally substituted by a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur, a $C_1$-$C_8$-alkoxycarbonyl optionally substituted by a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur; and $C_1$-$C_8$-alkyl optionally substituted by —OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$R^4$ and $R^5$ are independently selected from H and $C_1$-$C_8$-alkyl;

m and n are independently selected from an integer of 0, 1, 2 and 3; and t is integer selected from 1, 2 and 3;

wherein said $C_6$-$C_{15}$-aromatic carbocyclic group, $C_7$-$C_{15}$-aralkyl, $C_3$-$C_{15}$-carbocyclic group and 4- to 15-membered heterocyclic group having one or more heteroatoms selected from the group consisting of oxygen, nitrogen and sulphur, unless otherwise stated, are each optionally substituted by $C_7$-$C_{15}$-aralkyl, $C_1$-$C_8$-alkyl CN, $C_1$-$C_8$-alkylsulfonyl, $C_1$-$C_8$-haloalkylsulfonyl, halogen, $C_1$-$C_8$-alkoxy, OH, $C_1$-$C_8$-alkylcarbonyl, —C(O)—$C_6$-$C_{15}$-aromatic carbocyclic group, —C(O)—$C_3$-$C_{15}$-carbocyclic group, —C(O)-4- to 15-membered heterocyclic group having one or more heteroatoms selected from the group consisting of oxygen, nitrogen and sulphur, $C_1$-$C_8$-cyanoalkyl, $C_1$-$C_8$-cyanoalkoxy, $C_1$-$C_8$-haloalkyl, $C_1$-$C_8$-haloalkoxy, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, COOH, $C_1$-$C_8$-alkoxycarbonyl, 4- to 15-membered heterocyclic group having one or more heteroatoms selected from the group consisting of oxygen, nitrogen and sulphur optionally substituted by $C_7$-$C_{15}$-arakyl, $C_1$-$C_8$-alkyl, CN, $C_1$-$C_8$-alkylsulfonyl, $C_1$-$C_8$-haloalkylsulfonyl, halogen, $C_1$-$C_8$-alkoxy, OH, $C_1$-$C_8$-alkylcarbonyl, $C_1$-$C_8$-Cyanoalkyl, $C_1$-$C_8$-Cyanoalkoxy, $C_1$-$C_8$-haloalkyl, $C_1$-$C_8$-haloalkoxy, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino COOH, or $C_1$-$C_8$-alkoxycarbony, a $C_6$-$C_{15}$-aromatic carbocyclic group optionally substituted by $C_7$-$C_{15}$-arakyl, $C_1$-$C_8$-alkyl, CN, halogen, $C_1$-$C_8$-alkoxy, OH, $C_1$-$C_8$-alkylcarbonyl, $C_1$-$C_8$-Alkylaminocarbonyl, di($C_1$-$C_8$-alkyl)aminocarbonyl, $C_1$-$C_8$-alkylamino, di($C_1$-$C_8$-alkyl)amino, COOH, $CF_3$, or $C_1$-$C_8$-alkoxycarbonyl or a $C_3$-$C_{15}$-carbocyclic group optionally substituted by $C_7$-$C_{15}$-arakyl, $C_1$-$C_8$-alkyl, CN, halogen, $C_1$-$C_8$-alkoxy, OH, $C_1$-$C_8$-alkylcarbonyl, $C_1$-$C_8$-Alkylaminocarbonyl, di($C_1$-$C_8$-alkyl)aminocarbonyl, $C_1$-$C_8$-alkylamino, di($C_1$-$C_8$-alkyl)amino, COOH, $CF_3$, or $C_1$-$C_8$-alkoxycarbony, with the proviso that said compound of formula (I) is not 3-{1-[(5-chloro-2-methoxy-phenylcarbamoyl)-methyl]-2,4-dioxo-1,4-dihydro-2H-quinazolin-3-yl}-N-cyclopentyl-propionamide, N-(5-chloro-2,4-dimethoxy-phenyl)-2-[2,4-dioxo-3{[(tetrahydro-furan-2-ylmethyl)-carbamoyl]-methyl}-phenyl)-3,4-dihydro-2H-quinazolin-1-yl]-acetamide, 4-{6-chloro-1-[2-(3-chloro-4-ethoxy-phenyl)-2-oxoethyl]-2,4-dioxo-1,4-dihydro-2H-quinazolin-3-yl}-N-cyclopentyl-butyramide, 2-{1-[(5-chloro-2,4-dimethoxy-phenylcarbamoyl)-methyl]-2,4-dioxo-1,4-dihydro-2H-quinazolin-3-yl}-N-furan-2-ylmethyl-acetamide, 4-(2-{2,4-dioxo-3-[4-(phenethylcarbamoyl-methyl)-phenyl]-3,4-dihydro-2H-quinazolin-1-yl}-acetylamino)-benzoic acid ethyl ester, N-(3,5-dichloro-phenyl)-2-{2,4-dioxo-3-[4-(phenethylcarbamoyl-methyl)-phenyl]-3,4-dihydro-2H-quinazolin-1-yl}-acetamide, 2-{1-[(4-chloro-2-methoxy-5-methyl-phenylcarbamoyl)-methyl]-2,4-dioxo-1,4-dihydro-2H-quinazolin-3-yl}-N-cyclopentyl-acetamide, 2-{1-[(5-chloro-2,4-dimethoxy-phenylcarbamoyl)-methyl]-2,4-dioxo-1,4-dihydro-2H-quinazolin-3-yl}-N-phenethyl-acetamide and 1-[(5-chloro-2,4-dimethoxy-phenylcarbamoyl)-methyl]-2,4-dioxo-3-phenyl-1,3,4,5,6,8-hexahydro-2H-pyrido[4',3':4,5]thieno[2,d]pyrimidine-7-carboxylic acid ethyl ester.

Definitions

Terms used in the specification have the following meanings:

"Optionally substituted", as used herein, means the group referred to can be substituted at one or more positions by any one or any combination of the radicals listed thereafter.

"Halogen" or "halo" may be fluorine, chlorine, bromine or iodine; preferably it is bromine or chlorine or fluorine.

"$C_1$-$C_8$-Alkyl" denotes straight-chain or branched $C_1$-$C_8$-alkyl, which may be, e.g., methyl, ethyl, n-propyl, isopropyl, n-butyl, isobutyl, sec-butyl, tert-butyl, straight- or branched-pentyl, straight- or branched-hexyl, straight- or branched-heptyl or straight- or branched-octyl.

"$C_3$-$C_{15}$-Carbocyclic group" or "$C_5$-$C_{15}$-carbocyclic group", as used herein, denotes a carbocyclic group having 3- to 15-ring carbon atoms, e.g., a monocyclic group, either cycloaliphatic, such as a $C_3$-$C_8$-cycloalkyl and $C_5$-$C_{10}$-cycloalkyl, e.g., cyclopropyl, cyclobutyl, cyclopentyl, cyclohexyl, cycloheptyl or cyclooctyl; or a bicyclic group, such as bicyclooctyl, bicyclononyl, and bicyclodecyl including naphthyl.

"$C_6$-$C_{15}$-Aromatic carbocyclic group", as used herein, denotes an aromatic group having 6- to 15-ring carbon atoms, e.g., phenyl, phenylene, benzenetriyl, naphthyl, naphthylene or naphthalenetriyl.

"$C_1$-$C_8$-Alkoxy" denotes straight-chain or branched $C_1$-$C_8$-alkoxy which may be, e.g., methoxy, ethoxy, n-propoxy, isopropoxy, n-butoxy, isobutoxy, sec-butoxy, tert-butoxy, straight- or branched-pentoxy, straight- or branched-hexyloxy, straight- or branched-heptyloxy or straight- or branched-octyloxy. Preferably, $C_1$-$C_8$-alkoxy is $C_1$-$C_4$-alkoxy.

"$C_1$-$C_8$-Haloalkyl" and "$C_1$-$C_8$-haloalkoxy" denote $C_1$-$C_8$-alkyl and $C_1$-$C_8$-alkoxy, as hereinbefore defined, substituted by one or more halogen atoms, preferably one, two or three halogen atoms, preferably fluorine, bromine or chlorine atoms. Preferably, $C_1$-$C_8$-haloalkyl is $C_1$-$C_4$-alkyl substituted by one, two or three fluorine, bromine or chlorine atoms. Preferably, $C_1$-$C_8$-haloalkoxy is $C_1$-$C_4$-alkoxy substituted by one, two or three fluorine, bromine or chlorine atoms. "$C_1$-$C_8$-Hydroxyallyl" denotes $C_1$-$C_8$-alkyl as hereinbefore defined, substituted by at least one hydroxy group.

"$C_1$-$C_8$-Cyanoalkyl" denotes $C_1$-$C_8$-alkyl, as hereinbefore defined, substituted by at least one cyano group.

"$C_1$-$C_8$-Cyanoalkoxy" denotes $C_1$-$C_8$-alkoxy, as hereinbefore defined, substituted by at least one cyano group.

"$C_1$-$C_8$-Alkylsulfonyl", as used herein, denotes $C_1$-$C_8$-alkyl, as hereinbefore defined, linked to —$SO_2$—. Preferably, $C_1$-$C_8$-alkylsulfonyl is $C_1$-$C_4$-alkylsulfonyl.

"$C_1$-$C_8$-Haloalkylsulfonyl", as used herein, denotes $C_1$-$C_8$-haloalkyl, as hereinbefore defined, linked to —$SO_2$—. Preferably, $C_1$-$C_8$-haloalkylsulfonyl is $C_1$-$C_4$-haloalkylsulfonyl, especially trifluoromethylsulfonyl.

"Amino-$C_1$-$C_8$-alkyl" and "amino-$C_1$-$C_8$-alkoxy" denote amino attached by a nitrogen atom to $C_1$-$C_8$-alkyl, e.g., $NH_2$—($C_1$-$C_8$)—, or to $C_1$-$C_8$-alkoxy, e.g., $NH_2$—($C_1$-$C_8$)—O—, respectively, as hereinbefore defined. Preferably, amino-$C_1$-$C_8$-alkyl and amino-$C_1$-$C_8$-alkoxy are, respectively, amino-$C_1$-$C_4$-alkyl and amino-$C_1$-$C_4$-alkoxy.

"$C_1$-$C_8$-Alkylamino" and "di($C_1$-$C_8$-alkyl)amino" denote amino substituted respectively by one or two $C_1$-$C_8$-alkyl groups, as hereinbefore defined, which may be the same or different. Preferably, $C_1$-$C_8$-alkylamino and di($C_1$-$C_8$-alkyl) amino are respectively $C_1$-$C_4$-alkylamino and di($C_1$-$C_4$-alkyl)amino.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl. Preferably, amino-(hydroxy)-$C_1$-$C_8$-alkyl is amino-(hydroxy)-$C_2$-$C_4$-alkyl.

"Carboxy-$C_1$-$C_8$-alkyl" and "carboxy-$C_1$-$C_8$-alkoxy" denote carboxy attached by a carbon atom to $C_1$-$C_8$-alkyl or $C_1$-$C_8$-alkoxy, respectively, as hereinbefore defined. Preferably, carboxy-$C_1$-$C_8$-alkyl and carboxy-$C_1$-$C_8$-alkoxy are, respectively, carboxy-$C_1$-$C_4$-alkyl and carboxy-$C_1$-$C_4$-alkoxy.

"$C_1$-$C_8$-Alkylcarbonyl", "$C_1$-$C_8$-alkoxycarbonyl" and "$C_1$-$C_8$-haloalkylcarbonyl" denote $C_1$-$C_8$-alkyl, $C_1$-$C_8$-alkoxy or $C_1$-$C_8$-haloalkyl, respectively, as hereinbefore defined, attached by a carbon atom to a carbonyl group. "$C_1$-$C_8$-Alkoxycarbonyl" denotes $C_1$-$C_8$-alkoxy, as hereinbefore defined, wherein the oxygen of the alkoxy group is attached to the carbonyl carbon. Preferably, $C_1$-$C_8$-alkylcarbonyl, $C_1$-$C_8$-alkoxycarbonyl and $C_1$-$C_8$-haloalkylcarbonyl are, respectively, $C_1$-$C_4$-alkylcarbonyl, $C_1$-$C_4$-alkoxycarbonyl and $C_1$-$C_4$-haloalkylcarbonyl.

"$C_1$-$C_8$-Alkylamino" and "di($C_1$-$C_8$-alkyl)amino" denote $C_1$-$C_8$-alkyl, as hereinbefore defined, attached by a carbon atom to an amino group. The $C_1$-$C_8$-alkyl groups in di($C_1$-$C_8$-alkyl)amino may be the same or different. Preferably, $C_1$-$C_8$-alkylamino and di($C_1$-$C_8$-alkyl)amino are, respectively, $C_1$-$C_4$-alkylamino and di($C_1$-$C_4$-alkyl)amino.

"$C_1$-$C_8$-Alkylaminocarbonyl" and "di($C_1$-$C_8$-alkyl)aminocarbonyl" denote $C_1$-$C_8$-alkylamino and di($C_1$-$C_8$-alkyl) amino, respectively, as hereinbefore defined, attached by a nitrogen atom to the carbon atom of a carbonyl group. Preferably, $C_1$-$C_8$-alkylaminocarbonyl and di($C_1$-$C_8$-alkyl)-aminocarbonyl are, respectively, $C_1$-$C_4$-allylaminocarbonyl and di($C_1$-$C_4$-alkyl)-aminocarbonyl.

"Four (4)- to 15-membered heterocyclic group containing at least one ring heteroatom selected from the group consisting of nitrogen, oxygen and sulphur", as used herein, may be monocyclic or bicyclic, e.g., furan, tetrahydrofuran, pyrrole, pyrrolidine, pyrazole, imidazole, triazole, isotriazole, tetrazole, thiadiazole, isothiazole, oxadiazole, pyridine, oxazole, isoxazole, pyrazine, pyridazine, pyrimidine, piperidine, piperazine, morpholine, triazine, oxazine, thiazole, quinoline, isoquinoline, benzothiophene, benzoxazole, benzisoxazole, benzothiazole, benzisothiazole, benzofuran, indole, indazole benzodioxole or benzimidazole. Preferred heterocyclic groups include piperazine, morpholine, imidazole, isotriazole, pyrazole, pyridine, furan, oxazole, oxadiazole, isoxazole, thiazole, tetrazole benzothiophene, benzoxazole, benzothiazole, benzodioxole and benzofuran.

is a $C_6$-$C_{15}$-aromatic carbocyclic group, $C_5$-$C_{15}$-carbocyclic group, or a 4- to 15-membered heterocyclic group having one or more heteroatoms selected from the group consisting of oxygen, nitrogen and sulphur when fused with the pyrimidine dione derivative. For instance,

is $C_6$-$C_{15}$-aromatic carbocyclic group, such as a phenyl group, when fused with pyrimidine-2,4-dione derivative as depicted below:

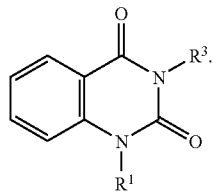

Another aspect of the invention provides compounds according to formula (I):

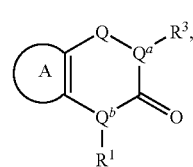

(I)

in free or salt form, wherein
Q is selected from $CH_2$, and $C(O)$;
$Q^a$ and $Q^b$ are independently selected from N and CH;

is selected from $C_6$-$C_{15}$-aromatic carbocyclic group, a $C_5$-$C_{15}$-carbocyclic group, and a 4- to 15-membered heterocyclic group having one or more heteroatoms selected from the group consisting of oxygen, nitrogen and sulphur;

$R^1$ is $-C(R^{1a}R^{1b})_mC(O)NR^{1c}R^{1d}$, $-C(R^{1a}R^{1b})_mC(O)CR^{1c}R^{1d}R^{1e}$, $-C(R^{1a}R^{1b})_mNR^{1c}R^{1d}$, $C(R^{1a}R^{1b})_mCR^{1c}R^{1d}R^{1e}$, $C(R^{1a}R^{1b})_mSO_2R^{1f}$;

$R^{1a}$ and $R^{1b}$ are independently selected from H, $-OH$, and $C_1$-$C_8$-alkyl optionally substituted by $-OH$ and halogen;

$R^{1c}$ is selected from H;
$C_6$-$C_{15}$-aromatic carbocyclic group, $C_7$-$C_{15}$-aralkyl, $C_3$-$C_{15}$-carbocyclic group, a 4- to 15-membered heterocyclic group having one or more heteroatoms selected from the group consisting of oxygen, nitrogen and sulphur;

$C_1$-$C_8$-alkoxy optionally substituted by OH, $-CN$, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$C_2$-$C_8$-alkenyl optionally substituted by $-OH$, $-CN$, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$C_2$-$C_8$-alkynyl optionally substituted by $-OH$, $-CN$, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur; and $C_1$-$C_8$-alkyl optionally substituted by $-OH$, $-CN$, halogen, $NR^4R^5$, $C_1$-$C_8$-alkoxycarbonyl, COOH, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$R^{1d}$ and $R^{1e}$ are H;
$R^{1f}$ is $C_6$-$C_{15}$-aromatic carbocyclic group, a $C_3$-$C_{15}$-carbocyclic group, $C_1$-$C_8$-haloalkyl and a 4- to 10-membered heterocyclic group having one or more heteroatoms selected from the group consisting of oxygen, nitrogen and sulphur;

$R^3$ is selected from $C_6$-$C_{15}$-aromatic carbocyclic group, $C_3$-$C_{15}$-carbocyclic group, alkylamino carbonyl, and —C($R^{3a}R^{3b})_n$C(O)N$R^{3c}R^{3d}$;

$R^{3a}$ and $R^{3b}$ are independently selected from H, —OH, and $C_1$-$C_8$-alkyl optionally substituted by —OH, halogen;

$R^{3c}$ and $R^{3d}$ are independently selected from H;

$C_6$-$C_{15}$-aromatic carbocyclic group, $C_3$-$C_{15}$-carbocyclic group;

a 4- to 15-membered heterocyclic group having one or more heteroatoms selected from the group consisting of oxygen, nitrogen and sulphur, and $C_1$-$C_8$-alkyl optionally substituted by —OH, —CN, halogen, N$R^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur, m and n are independently selected from an integer of 0, 1 and 2; and t is an integer selected from 1 and 2;

wherein said $C_6$-$C_{15}$-aromatic carbocyclic group, $C_7$-$C_{15}$-aralkyl, $C_3$-$C_{15}$-carbocyclic group and 4- to 15-membered heterocyclic group having one or more heteroatoms selected from the group consisting of oxygen, nitrogen and sulphur, unless otherwise stated, are each optionally substituted by $C_7$-$C_{15}$-arakyl, $C_1$-$C_8$-alkyl CN, $C_1$-$C_8$-allylsulfonyl, $C_1$-$C_8$-haloalkylsulfonyl, halogen, $C_1$-$C_8$-alkoxy, OH, $C_1$-$C_8$-alkylcarbonyl, —C(O)—$C_6$-$C_{15}$-aromatic carbocyclic group, —C(O)—$C_3$-$C_{15}$-carbocyclic group, —C(O)-4- to 15-membered heterocyclic group having one or more heteroatoms selected from the group consisting of oxygen, nitrogen and sulphur, $C_1$-$C_8$-cyanoalkyl, $C_1$-$C_8$-cyanoalkoxy, $C_1$-$C_8$-haloalkyl, $C_1$-$C_8$-haloalkoxy, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, COOH, $C_1$-$C_8$-alkoxycarbonyl, 4- to 15-membered heterocyclic group having one or more heteroatoms selected from the group consisting of oxygen, nitrogen and sulphur optionally substituted by $C_7$-$C_{15}$-arakyl, $C_1$-$C_8$-alkyl, CN, $C_1$-$C_8$-alkylsulfonyl, $C_1$-$C_8$-haloalkylsulfonyl, halogen, $C_1$-$C_8$-alkoxy, OH, $C_1$-$C_8$-alkylcarbonyl, $C_1$-$C_8$-Cyanoalkyl, $C_1$-$C_8$-Cyanoalkoxy, $C_1$-$C_8$-haloalkyl, $C_1$-$C_8$-haloalkoxy, $C_1$-$C_8$-alkylaminocarbonyl, di($C_1$-$C_8$-alkyl)aminocarbonyl, $C_1$-$C_8$-alkylamino, di($C_1$-$C_8$-alkyl) amino COOH, or $C_1$-$C_8$-alkoxycarbony, a $C_6$-$C_{15}$-aromatic carbocyclic group optionally substituted by $C_7$-$C_{15}$-arakyl, $C_1$-$C_8$-alkyl, CN, halogen, $C_1$-$C_8$-alkoxy, OH, $C_1$-$C_8$-alkylcarbonyl, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, COOH, $CF_3$, or $C_1$-$C_8$-alkoxycarbonyl or a $C_3$-$C_{15}$-carbocyclic group optionally substituted by $C_7$-$C_{15}$-arakyl, $C_1$-$C_8$-alkyl, CN, halogen, $C_1$-$C_8$-alkoxy, OH, $C_1$-$C_8$-alkylcarbonyl, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, COOH, $CF_3$, or $C_1$-$C_8$-alkoxycarbonyl.

Another aspect of the invention provides compounds according to claim 1 where said compound is of formula (Ia):

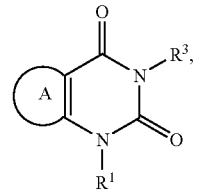

(Ia)

in free or salt form, wherein $R^1$ is selected from —C($R^{1a}R^{1b})_m$C(O)N$R^{1c}R^{1d}$, —C($R^{1a}R^{1b})_t$N$R^{1c}R^{1d}$ and —C($R^{1a}R^{1b})_m$C(O)N$R^{1c}R^{1d}$;

$R^{1a}R^{1b}$ and $R^{1c}$ are independently selected from H and OH;

$R^{1d}$ is a $C_6$-$C_{15}$-aromatic carbocyclic group or a 4- to 15-membered heterocyclic group having one or more heteroatoms selected from the group consisting of oxygen, nitrogen and sulphur, or a $C_1$-$C_8$-alkyl substituted by a $C_6$-$C_{15}$-aromatic carbocyclic group;

m is an integer selected from 0, 1 and 2;

$R^3$ is a $C_6$-$C_{15}$-aromatic carbocyclic group substituted by —C($R^{3a}R^{3b})_n$C(O)N$R^{3c}R^{3d}$, a C($R^{3a}R^{3b})_n$C(O)N$R^{3c}R^{3d}$, a 4- to 15-membered heterocyclic group having one or more heteroatoms selected from the group consisting of oxygen, nitrogen and sulphur;

$R^{3a}$, $R^{3b}$ and $R^{3c}$ are H;

$R^{3d}$ is a $C_3$-$C_{15}$-carbocyclic group, a $C_6$-$C_{15}$-aromatic group, or a 4- to 15-membered heterocyclic group having one or more heteroatoms selected from the group consisting of oxygen, nitrogen and sulphur; or $C_1$-$C_8$-alkyl optionally substituted by OH, a $C_3$-$C_{15}$-carbocyclic group, $C_6$-$C_{15}$-aromatic group or a 4- to 15-membered heterocyclic group having one or more heteroatoms selected from the group consisting of oxygen, nitrogen and sulphur;

n is 0, 1 or 2, t is 1, or $R^{3c}$ and $R^{3d}$, together with the N atom they are attached, form a 4- to 15-membered heterocyclic group having one or more heteroatoms selected from the group consisting of oxygen, nitrogen and sulphur; and

is selected from:

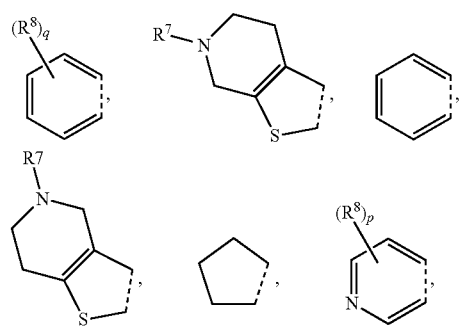

-continued

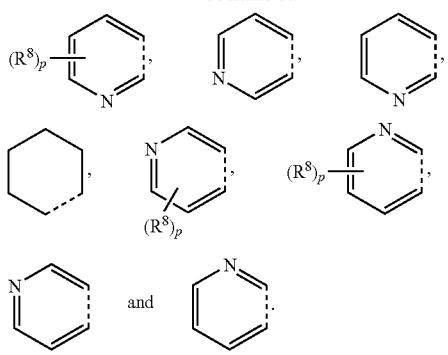

where

R[7] is selected from H and $C_1$-$C_8$-alkoxycarbonyl;

each R[8] is selected from H, halo, CN, $CO_2H$, $CH_2NH_2$ and $C_1$-$C_8$-alkyl;

p is an integer selected of 1 to 3; and q is an integer selected of 1 to 4.

Another aspect of the invention provides compounds according to formula (I), where R[1] is suitably —$C(R^{1a}R^{1b})_m$ $C(O)NR^{1c}R^{1d}$, where $R^{1a}R^{1b}$ and $R^{1c}$ are suitably H, $R^{1d}$ is suitably a $C_6$-$C_{15}$-aromatic carbocyclic group or a 4- to 15-membered heterocyclic group having one or more heteroatoms selected from the group consisting of oxygen, nitrogen and sulphur. Preferably, the $C_6$-$C_{15}$-aromatic carbocyclic group is phenyl and substituted by halogen (e.g., Cl), $C_1$-$C_8$-alkyl (e.g., methyl) optionally substituted by 4- to 15-membered heterocyclic group having one or more heteroatoms selected from the group consisting of oxygen, nitrogen and sulphur, $C_1$-$C_8$-alkoxy (e.g., methoxy), CN, $C_1$-$C_8$-allylaminocarbonyl (e.g., 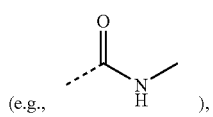 ), $C_1$-$C_8$-cyanoalkoxy, $CF_3$, $C_1$-$C_8$-alkoxycarbonyl a heterocyclic group, such as and/or di($C_1$-$C_8$-alkyl)aminocarbonyl.

Also, when $R^{1d}$ is suitably a 4- to 15-membered heterocyclic group having one or more heteroatoms selected from the group consisting of oxygen, nitrogen and sulphur, such as pyridine, pyrazine, piperidine and benzothiazole. This heterocyclic group is suitably substituted by $C_1$-$C_8$-alkyl (e.g., methyl), OH and halogen (e.g., Cl).

Also, R[1] is suitably —$C(R^{1a}R^{1b})_m NR^{1c}R^{1d}$, where $R^{1a}$ and $R^{1c}$ are suitably H, $R^{1b}$ is suitably H or OH and m is suitably 1. $R^{1d}$ is suitably a $C_6$-$C_{15}$-aromatic carbocyclic group or a 4- to 15-membered heterocyclic group having one or more heteroatoms selected from the group consisting of oxygen, nitrogen and sulphur. Preferably, the $C_6$-$C_{15}$-aromatic carbocyclic group is phenyl and substituted by halogen (e.g., Cl), $C_1$-$C_8$-alkyl (e.g., methyl) optionally substituted by 4- to 15-membered heterocyclic group having one or more heteroatoms selected from the group consisting of oxygen, nitrogen and sulphur, $C_1$-$C_8$ (e.g., 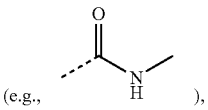 ), alkoxy (e.g., methoxy), CN, $C_1$-$C_8$-alkylaminocarbonyl $C_1$-$C_8$-cyanoalkoxy, $CF_3$, $C_1$-$C_8$-alkoxycarbonyl a heterocyclic group, such as and/or di($C_1$-$C_8$-alkyl)aminocarbonyl. For instance, a suitable example of R[1] is

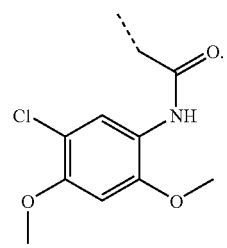

Also, $R^{1d}$ is suitably a 4- to 15-membered heterocyclic group having one or more heteroatoms selected from the group consisting of oxygen, nitrogen and sulphur, such as pyridine, pyrazine, piperidine and benzothiazole. This heterocyclic group is suitably substituted by $C_1$-$C_8$-alkyl (e.g., methyl), OH and halogen (e.g., Cl).

R[1] is also suitably $C(R^{1a}R^{1b})_m C(O)NR^{1c}R^{1d}$, where $R^{1a}R^{1b}$ and $R^{1c}$ are suitably H, $R^{1d}$ is a $C_1$-$C_8$-alkyl substituted by a $C_6$-$C_{15}$-aromatic carbocyclic group. For instance, R[1] is suitably

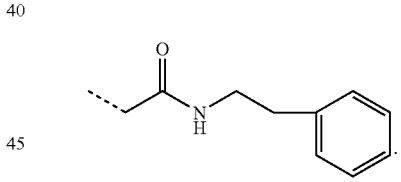

R[3] is suitably a $C_6$-$C_{15}$-aromatic carbocyclic group substituted by —$C(R^{3a}R^{3b})_n C(O)NR^{3c}R^{3d}$. Preferably, the $C_6$-$C_{15}$-aromatic group is phenyl. Preferably, $R^{3a}$ and $R^{3b}$ are H, n is 1 $R^{3c}$ is H and $R^{3d}$ is a C1-$C_8$-alkyl substituted by phenyl. For example, R[3] is suitably

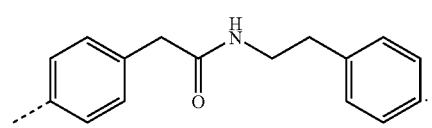

R[3] is also suitably $C(R^{3a}R^{3b})_n C(O)NR^{3c}R^{3d}$. Preferably, $R^{3a}$ and $R^{3b}$ are H, n is 0, 1 or 2, $R^{3c}$ is H and $R^{3d}$ is suitably a $C_3$-$C_{15}$-carbocyclic group or $C_1$-$C_8$-alkyl substituted by phenyl. For example, R[3] is suitably

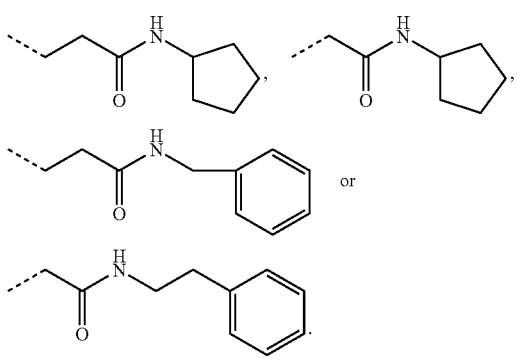

Also, $R^{3d}$ is suitably $C_3$-$C_{15}$-carbocyclic group, such as cyclopentyl, cyclohexyl, and cyclopropyl, a $C_6$-$C_{15}$-aromatic group, such as phenyl, or a 4- to 15-membered heterocyclic group having one or more heteroatoms selected from the group consisting of oxygen, nitrogen and sulphur, such as pyridine, piperidine, isoxazole and morpholine. $R^{3d}$ is also suitably $C_1$-$C_8$-alkyl substituted by a $C_3$-$C_{15}$-carbocyclic group, $C_6$-$C_{15}$-aromatic group and a 4- to 15-membered heterocyclic group having one or more heteroatoms selected from the group consisting of oxygen, nitrogen and sulphur and OH. For instance, $R^3$ is suitably

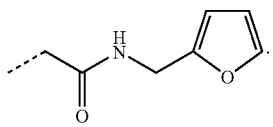

$R^3$ is also suitably a 4- to 15-membered heterocyclic group having one or more heteroatoms selected from the group consisting of oxygen, nitrogen and sulphur, such as pyrrolidine. This 4- to 15-membered heterocyclic group is preferably substituted by C(O)—$C_3$-$C_{15}$-carbocyclic group, such as cyclopentyl. For example, $R^3$ is suitably

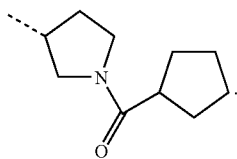

$R^{3d}$ is also suitably $C_1$-$C_8$-alkoxy, $C_1$-$C_8$-alkyl $C_1$-$C_8$-alkylamino, and di($C_1$-$C_8$-alkyl)amino.

Also, $R^{3d}$ and $R^{3c}$, together with the N atom they are attached, form a 4- to 15-membered heterocyclic group having one or more heteroatoms selected from the group consisting of oxygen, nitrogen and sulphur, such as morpholine or piperazine. This heterocyclic group, when piperazine, is suitably substituted by methyl.

is suitably selected from selected from $C_6$-$C_{15}$-aromatic carbocyclic group. Preferably,

is suitably a $C_6$ aromatic carbocyclic group, such as phenyl that can suitably be substituted by at least one group selected from halogen (e.g., Cl) and $C_1$-$C_8$-alkyl (e.g., methyl or ethyl).

is also suitably a $C_5$-$C_{15}$-carbocyclic group or a 4- to 15-membered heterocyclic group having one or more heteroatoms selected from the group consisting of oxygen, nitrogen and sulphur.

Preferably,

is suitably selected from:

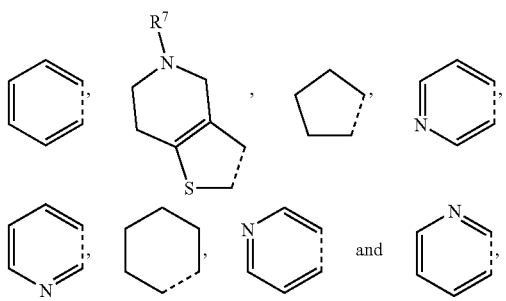

where $R^7$ is suitably H, halogen (e.g., Cl), COOH or $C_1$-$C_8$-alkoxycarbonyl (e.g., COOCH$_2$CH$_3$).

Another aspect of the invention provides for the use of the following compounds of formula (I), that are subject to a proviso. These compounds are 3-{1-[(5-chloro-2-methoxyphenylcarbamoyl)-methyl]-2,4-dioxo-1,4-dihydro-2H-quinazolin-3-yl}-N-cyclopentyl-propionamide, N-(5-chloro-2,4-dimethoxy-phenyl)-2-[2,4-dioxo-3{[(tetrahydrofuran-2-ylmethyl)-carbamoyl]-methyl}-phenyl)-3,4-dihydro-2H-quinazolin-1-yl]-acetamide, 4-{6-chloro-1-[2-(3-chloro-4-ethoxy-phenyl)-2-oxoethyl]-2,4-dioxo-1,4-dihydro-2H-quinazolin-3-yl}-N-cyclopentyl-butyramide, 2-{1-[(5-chloro-2,4-dimethoxy-phenylcarbamoyl)-methyl]-2,4-dioxo-1,4-dihydro-2H-quinazolin-3-yl}-N-furan-2-ylmethyl-acetamide, 4-(2-{2,4-dioxo-3-[4-(phenethylcarbamoyl-methyl)-phenyl]-3,4-dihydro-2H-quinazolin-1-yl}-acetylamino)-benzoic acid ethyl ester, N-(3,5-dichlorophenyl)-2-{2,4-dioxo-3-[4-(phenethylcarbamoyl-methyl)-phenyl]-3,4-dihydro-2H-quinazolin-1-yl}-acetamide, 2-{1-[(4-chloro-2-methoxy-5-methyl-phenylcarbamoyl)-methyl]-2,4-dioxo-1,4-dihydro-2H-quinazolin-3-yl}-N-cyclopentyl-acetamide, 2-{1-[(5-chloro-2,4-dimethoxyphenylcarbamoyl)-methyl]-2,4-dioxo-1,4-dihydro-2H-quinazolin-3-yl}-N-phenethyl-acetamide and 1-[(5-chloro-2,4-dimethoxy-phenylcarbamoyl)-methyl]-2,4-dioxo-3-phenyl-1,3,4,5,6,8-hexahydro-2H-pyrido[4',3':4,5]thieno[2,d]pyrimidine-7-carboxylic acid ethyl ester, in free or salt form, for the manufacture for the treatment of an inflammatory or allergic condition, particularly an inflammatory or obstructive airways disease.

Further, an aspect of the present invention provides for any uses for these compounds as are described for compounds of formula (I) herein.

In a yet a further aspect, the present invention provides for the use of a compound of formula (I) in any of the aforementioned embodiments, in free or salt form, for the manufacture of a medicament for the treatment of an inflammatory or allergic condition, particularly an inflammatory or obstructive airways disease.

A preferred embodiment of the present invention provides for the use of a compound of formula (I) in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis sire.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. It is understood by those skilled in the art that combinations of substituents where not possible are not an aspect of the present invention.

Salts and Isomers

Many of the compounds represented by formula (I) are capable of forming acid addition salts, particularly pharmaceutically acceptable acid addition salts. Pharmaceutically acceptable acid addition salts of the compound of formula (I) include those of inorganic acids, e.g., hydrohalic acids, such as hydrochloric acid or hydrobromic acid; nitric acid; sulphuric acid; phosphoric acid; and organic acids, e.g., aliphatic monocarboxylic acids, such as formic acid, acetic acid, diphenylacetic acid, triphenylacetic acid, caprylic acid, dichloroacetic acid, trifluoroacetic acid, hippuric acid, propionic acid and butyric acid; aliphatic hydroxy acids, such as lactic acid, citric acid, gluconic acid, mandelic acid, tartaric acid or malic acid; dicarboxylic acids, such as adipic acid, aspartic acid, fumaric acid, glutamic acid, maleic acid, malonic acid, sebacic acid or succinic acid; aromatic carboxylic acids, such as benzoic acid, p-chlorobenzoic acid, or nicotinic acid; aromatic hydroxy acids, such as o-hydroxybenzoic acid, p-hydroxybenzoic acid, 1-hydroxy-naphthalene-2-carboxylic acid or 3-hydroxynaphthalene-2-carboxylic acid; and sulfonic acids, such as ethanesulfonic acid, ethane-1,2-disulfonic acid, 2-hydroxyethane-sulfonic acid, methanesulfonic acid, (+)-camphor-10-sulfonic acid, benzenesulfonic acid, naphthalene-2-sulfonic acid, naphthalene-1,5-disulfonic acid or p-toluenesulfonic acid. These salts may be prepared from compounds of formula (I) by known salt-forming procedures.

Compounds of formula (I) which contain acidic, e.g., carboxyl, groups, are also capable of forming salts with bases, in particular, pharmaceutically acceptable bases, such as those well-known in the art; suitable such salts include metal salts, particularly, alkali metal or alkaline earth metal salts, such as sodium, potassium, magnesium, calcium or zinc salts; or salts with ammonia or pharmaceutically acceptable organic amines or heterocyclic bases, such as benethamine, arginine, benzathine, diethanolamine, ethanolamine, 4(2-hydroxyethyl)morpholine, 1-(2-hydroxyethyl)pyrrolidine, N-methyl glucamine, piperazine, triethanol-amine or tromethamine. These salts may be prepared from compounds of formula (I) by known salt-forming procedures.

In those compounds where there is an asymmetric carbon atom or an axis of chirality the compounds exist in individual optically active isomeric forms or as mixtures thereof, e.g., as racemic or diastereomeric mixtures. The present invention embraces both individual optically active R and S isomers, as well as mixtures, e.g., racemic or diastereomeric mixtures, thereof.

Tautomers of a compound of formula (I), where possible, are an aspect of the invention. Such tautomers include but are not limited to keto/enol tautomers as understood by one skilled in the art.

Specific preferred compounds of formula (I) are described hereinafter in the Examples.

Another embodiment of the present invention provides a process for the preparation of compounds of formula (I), in free or pharmaceutically acceptable salt form, which comprises the steps of:

(i) reacting a compound of formula (II):

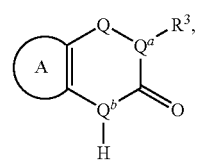

wherein

$R^3$, $Q^b$ is N and Q are as defined in Claim 1, with a compound of formula (III):

X—R'  (III)

wherein X is a leaving group and R' is selected from $C_1$-$C_8$-alkyl or $C_1$-$C_8$-alkoxycarbonyl to provide a compound of formula (IV):

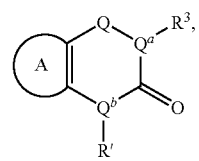

wherein when R' is $C_1$-$C_8$-alkoxycarbonyl, the alkoxycarbonyl is hydrolysed to the respective acid and the resultant compound is reacted with an amine to generate the amide derivative, and (ii) removing any protecting groups and recovering the resultant compound of formula (I) in free or pharmaceutically acceptable salt form.

The compounds of formula (I) can be prepared, for example, using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5$^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is T. W. Greene and P. G. M. Wuts, *Protective Groups In Organic Synthesis*, Wiley and Sons (1999).

Generally, compounds described in the scope of this patent application can be synthesized by the routes described in Schemes 1 and 2 and the Examples. The following schemes are illustrative and should not be construed as limiting the present invention.

For example, in Scheme 1, compound 1 is reacted with an amine and subsequently cyclised by phosgene or its equivalents such as triphosgene to provide compound 2. Compound 2 is hydrolysed to the carboxylic acid and coupled with an amine such as benzylamine or cyclopentylamine to give compound 3. Compound 3 is alkylated with a acetic acid derivative, such as bromo-acetic acid methyl ester, to provide compound 4. Compound 4 is hydrolysed and the resulting carboxylic acid coupled with an amine, e.g., aryl amine, to provide compound 5.

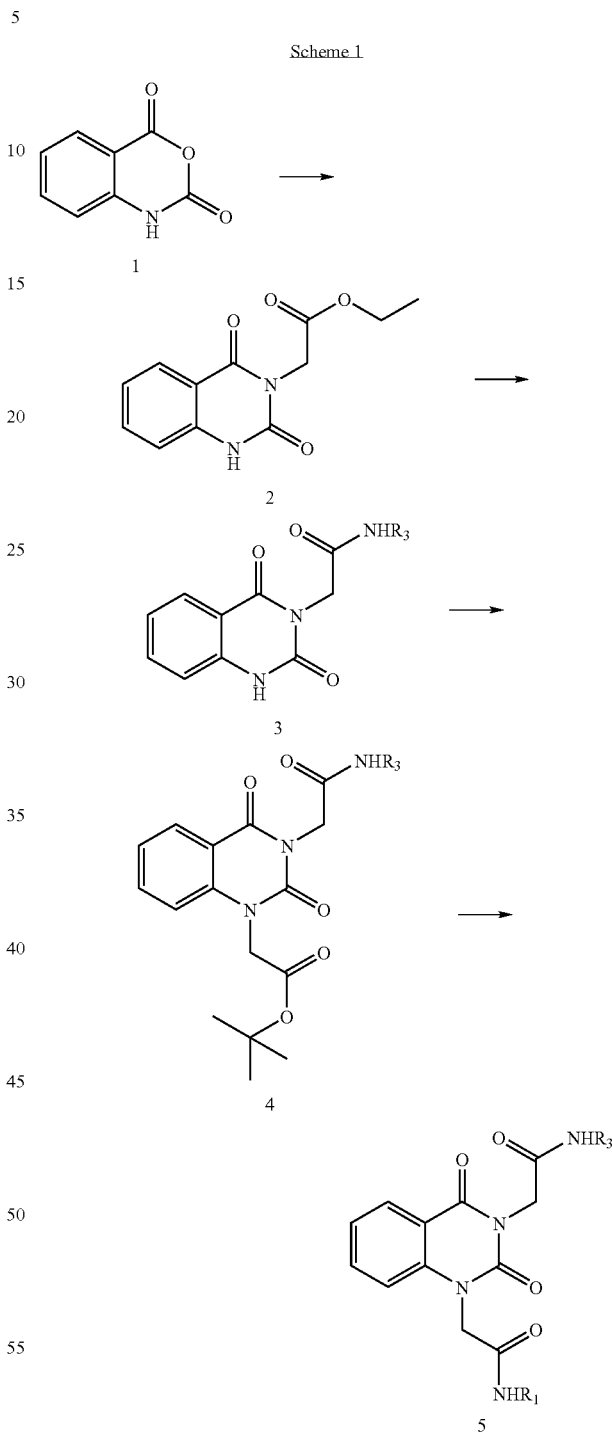

Scheme 1

Scheme 2 highlights a route to pyrido-fused pyrimidine-2, 4-diones. For example, compound 6 is reacted with a urea derivative, such as ureido-acetic acid ethyl ester in a one pot reaction catalysed by Palladium (0) to provide compound 7. Compound 7 can be further derivatized by processes described in Scheme 1 to provide compound 8.

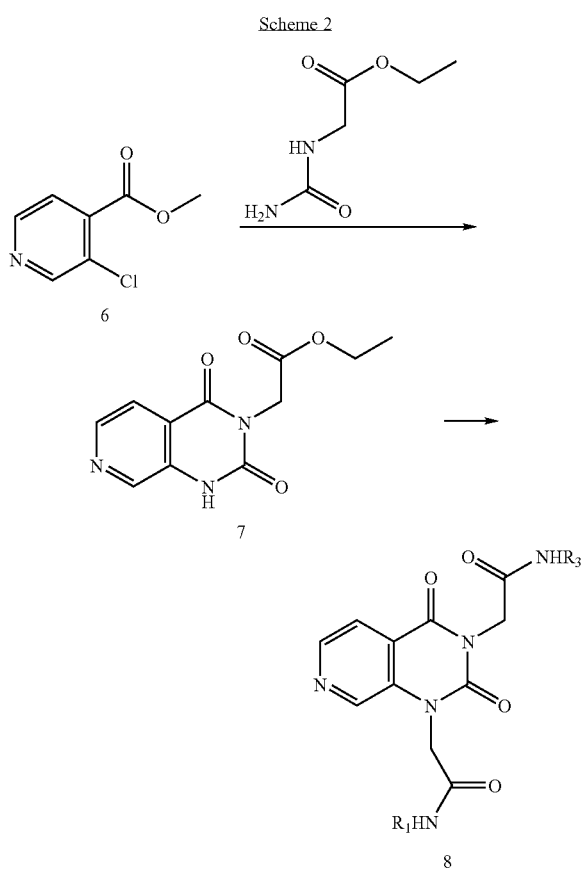

Scheme 2

Pharmaceutical Uses

Lysophospholipids (LPLs), like sphingosine-1-phosphate (S1P) are lipid signaling molecules that are derived from cell membrane associated precursors (Stunff et al., *J Cell Biochem*, 92: 882-899 (2004)). S1P is a metabolic product of sphingolipids, which are ubiquitous phospholipids found in all eukaryotic cell types. S1P is produced intracellular and released upon appropriate stimulation. The predominant cellular sources of S1P include platelets and tissue mast cells. S1P synthesis begins with the conversion of endogenous membrane-derived sphingomyelin to ceramide (CER) by sphinogmyelinase, then to sphingosine by ceremidase. Sphingosine is then converted to S1P via phosphorylation by one of two sphingosine kinases (SphK1 or SphK2) (Spiegel and Milstien, *Nat Rev Mol Cell Biol*, 4: 397-407 (2003)). Whereas ceramide and sphingosine have been associated with cell growth arrest and apoptosis, S1P has been shown to be important in cell growth and survival. S1P is an unusual lipid in that it can act both intracellular and extracellular. Intracellular S1P binds to putative endoplasmic reticulum-associated receptors to facilitate the release of intracellular stores of calcium during cell activation. Most of these phospholipids compounds fail to effectively discriminate between different S1P receptors and have poor physicochemical properties, which limits their potential use as pharmaceutical agents. Thus, there exists a need for compounds, which are not phospholipids that bind or otherwise regulate S1P receptors and can also selectively bind to a specific S1P receptor.

Extracellular S1P acts as a potent ligand for a family of G-protein coupled receptors (GPCRs). The best characterized actions of S1P are mediated by its binding to a class of GPCRs known as the endothelial differentiation gene-1 (EDG-1) family. To date, a total of five EDG receptors, EDG-1, EDG-5, EDG-3, EDG-6 and EDG-8 have been shown to bind S1P with high affinity and specificity. These receptors are also designated S1P1, S1P2, S1P3, S1P4 and S1P5, respectively (Sanchez and Hla, *J Cell Biochem*, 92: 913-922 (2004)). The existence of multiple receptors for S1P implies that its functions may be considerably diverse. S1P receptors have a widespread cellular and tissue distribution and are well-conserved in human and rodent species (Spiegel and Milstien, *Biochim Biophys Acta*, 484:107-116 (2000); and Hla, *Prostaglandins Other Lipid Mediat*, 64: 135-142 (2001)). S1P receptors can couple to different G-proteins to elicit a wide variety of cellular responses (Goetzl and Rosen, *J Clin Invest*, 114:1531-1537 (2004); and Spiegel and Milstien, *Nat Rev Mol Cell Biol*, 4: 397-407 (2003)). Studies with transfected cells have shown that S1P1 receptors signals exclusively through $G_i$ proteins to inhibit adenylate cyclase and stimulate mitogen activated protein kinase (MAPK) in addition to PTX sensitive activation of phospholipase C (PLC). S1P2 and S1P3 receptors can signal through multiple $G_□$ subtypes including $G_1$, $G_q$ and $G_{12/13}$. S1P2 activates Ras/MAPK via Gi but unlike S1P1 stimulates PLC via a PTX insensitive $G_q$ and activates Rho. S1P4 primarily Gi and the MAPK pathway and S1P5 is coupled to Gi and G12 to inhibit adenylate cyclase but does not stimulate MAPK.

Several studies have indicated that many cell types express more than one subtype of S1P receptor and that multiple S1P receptors may cooperate to lead to particular biological responses to S1P. As a result, S1P is implicated in a large variety of physiological functions. The receptors for S1P are broadly expressed on cell types of the immune system including monocytes, B and T lymphocytes, dendritic cells, mast cells, natural killer cells, and eosinophils (Lin and Broyce, *Adv Immunol*, 89: 141-167 (2006)). One of the most studied effects of S1P is its role in lymphocyte migration. The binding of S1P to several types of S1P receptors can modulate the migration of immune cells in vitro, but the in vivo effects of S1P on lymphocyte migration, tissue homing and recirculation are mediated exclusively by S1P1 (Brinkmann and Baumruker, *Curr Opin Pharmacol*, 6: 1-7 (2006)). The predominant outcome of pharmalogical agonists of S1P receptors in vivo is the sequestering of lymphocytes in secondary lymph nodes. In mast cells, FcepsilonRI triggering leads to release of S1P which in turn activates its S1P1 and S1P2 receptors expressed on mast cells (Jolly et al., *J Exp Med*, 199: 959-970 (2004); and Jolly et al., *Mol Immunol*, 38:1239-1245 (2001)). Activation of S1P1 and S1P2 are required for normal mast cell degranulation and chemotaxis. A rapidly growing literature suggests that S1P mediates several aspects of cardiovascular function (Brinkmann and Baumruker, *Curr Opin Pharmacol*, 6: 1-7 (2006)). In vitro studies indicate that S1P administration can contract a variety of cultured and freshly isolated smooth muscle cell types (Watterson et al., *Cell Signal*, 17: 289-298 (2005)). Cardiovascular effects have been measured for S1P in rat and dog hearts (Sugiyama et al., *Jpn J Pharmacol*, 82: 338-42 (2000); Sugiyama et al., *Cardiovasc Res*, 46: 199-25 (2000); Yatomi et al., *J Biochem*, 121: 969-73 (1997); and Forrest et al., *J Pharm Exp Therap*, 309: 758-768 (2004)). S1P3 has been found to mediate vasoconstriction of cerebral arteries and induce bradycardia and hypertension in rodents (Salomone et al., *Eur J Pharmacol*, 469: 125-34 (2003)). In vascular endothelial cells, S1P stimulates cell proliferation and migration in vitro and angiogenesis in vivo (Lee et al., *Cell*, 99: 301-21 (1999)). These S1P actions were mediated via S1P1 and S1P3 receptors. S1P1 has also been implicated in tumor angiogenesis and tumor growth. In contrast, S1P2 exerts inhibitory effects on endothelial migration, morphogenesis and angiogenesis in vivo. In addition, lung endothelial barrier function is enhanced by S1P activation of S1P1 and endothelial permeability is increased by activation of S1P2. In epithelial cells, S1P3 receptor have been shown to induced reorganization of tight junctions and consequently compromises lung barrier integrity. While functions of S1P4 and S1P5 are less well-understood, the S1P4 receptor has been shown to be localized in hematopoeitic cells and tissue (Graeler et al., *Curr Top Microbiol Immunol,* 246: 131-6 (1999)) and the S1P5 receptor has been shown to be primarily a neuronal receptor with some expression in lymphoid tissue in rodents but with a broader expression pattern in human tissue (Im et al., *J Biol Chem,* 275(19): 14281-6 (2000); Neidernberg et al., *Biochem Pharmacol,* 64: 1243-50 (2002)).

S1P2 is a seven transmembrane G protein coupled receptor (GPCR) [Okamoto H et al. (2000), Mazurais D et al. (2002), An S et al., (2000), Ancellin N, Hla T. (1999), U.S. Pat. No. 5,585,476, WO 200056135 and WO 9954351]. Many medically significant biological processes are mediated by signal transduction pathways that involve G-proteins [Lefkowitz (1991)]. The family of GPCRs includes receptors for hormones, neurotransmitters, growth factors, and viruses. Specific examples of GPCRs include receptors for such diverse agents as dopamine, calcitonine, adrenergic hormones, endotheline, cAMP, adenosine, acetylcholine, serotonine, histamine, thrombin, kinine, follicle stimulating hormone, opsins, endothelial differentiation gene-1, rhodopsins; odorants, cytomegalovirus, G-proteins themselves, effector proteins, such as phospholipase C, adenyl cyclase, and phosphodiesterase, and actuator proteins, such as protein kinase A and protein kinase C.

The invention provides compounds that are modulators of either human S1P2 and S1P4 or both s1P2 and S1P4 which is associated with the cardiovascular diseases, disorders of the gastroenterology system, reproduction diseases, disorders of the peripheral and central nervous system and respiratory diseases. The invention also provides assays for the identification of compounds useful in the treatment or prevention of cardio-vascular diseases, disorders of the gastroenterology system, reproduction diseases, disorders of the peripheral and central nervous system and respiratory diseases. The invention also features compounds which bind to and/or activate or inhibit the activity of S1P2 and S1P4, as well as pharmaceutical compositions comprising such compounds.

S1P2:

S1P2 expression has been demonstrated on a wide variety of cell types, It has been shown to be involved in angiogenesis and vascular permeability. It further has been shown to be involved in wound healing via activation to fibroblasts. The invention features compounds which bind to and/or activate or inhibit the activity of S1P2, as well as pharmaceutical compositions comprising such compounds. The compounds of the invention are therefore useful in the treatment and/or prevention of:

Cardiovascular Diseases diseases caused by vascular contraction, such as cerebrovascular spasmodic disease following subarachroid hemorrhage or cerebral infarction, cardiovascular spasmodic disease, hypertension, kidney diseases, cardiac infarction, angina, arrhythmia, portal hypertension in association with cirrhosis and varicosity in association with cirrhosis.

diseases caused by vascular dilation, such as chronic headache, e.g., hemicrania, tension headache, headache of the mixed type, cluster headaches, hemorrhoid and cardiac diseases.

Disorders of the Gastroenterology System

Gastrointestinal diseases comprise primary or secondary, acute or chronic diseases of the organs of the gastrointestinal tract which may be acquired or inherited, benign or malignant or metaplastic, and which may affect the organs of the gastrointestinal tract or the body as a whole. They comprise, but are not limited to, 1) disorders of the esophagus like achalasia, vigorous achalasia, dysphagia, cricopharyngeal incoordination, pre-esophageal dysphagia, diffuse esophageal spasm, globus sensation, Barrett's metaplasia, gastroesophageal reflux, 2) disorders of the stomach and duodenum like functional dyspepsia, inflammation of the gastric mucosa, gastritis, stress gastritis, gastric ulcers, duodenal ulcers, neoplasms of the stomach, 3) disorders of the pancreas like acute or chronic pancreatitis, insufficiency of the exocrinic or endocrinic tissues of the pancreas like steatorrhea, diabetes, neoplasms of the exocrine or endocrine pancreas like 3.1) multiple endocrine neoplasia syndrome, ductal adenocarcinoma, cystadenocarcinoma, islet cell tumors, insulinoma, gastrinoma, carcinoid tumors, glucogonoma, Zollinger-Ellison syndrome, Vipoma syndrome, malabsorption syndrome, 4) disorders of the bowel like chronic inflammatory diseases of the bowel, Crohn's disease, ileus, diarrhea and constipation, colonic inertia, megacolon, malabsorption syndrome, ulcerative colitis, 4.1) functional bowel disorders like irritable bowel syndrome, 4.2) neoplasms of the bowel like familial polyposis, adenocarcinoma, primary malignant lymphoma, carcinoid tumors, Kaposi's sarcoma, polyps, cancer of the colon and rectum. Medical conditions also include irritable bowel syndrome, chronic constipation, functional dyspepsia, delayed gastric emptying, gastroesophageal reflux disease, gastroparesis, post-operative ileus, intestinal pseudo-obstruction and drug-induced delayed transit.

Ocular Disorders

Retinopathies including simple or nonproliferative retinopathies and proliferative retinopathies such as Sickle-cell anemia, hypertensive retinopathy, diabetic retinopathy, diabetic macular oedema, proliferative diabetic retinopathy, cystold macular oedema, retinal vein and artery occlusion, all forms of optic neuritis, age-related macular degeneration, retinal detachment, retinitis pigmentosa, Stargardt's disease, Best's viteliform retinal degreneration, Leber's congenital amaurosis, and other hereditary retinal degenerations, pathologic myopia, retinophay of permaturity, and Leber's hereditary optic neurophathy, the after effects of corneal transplantation or of refractive corneal surgery, keratoconjunctivitis sicca, or dry eye and herpes keratitis.

Wound Healing

As an angiogenic agent for the promotion of wound healing either independently or in conjunction with sphingosine phosphate or a modulator of S1P function, especially for the treatment of diabetic wounds.

Respiratory Diseases.

Agents of the invention, particularly those which have S1P2 and/or S1P4 activity, are particularly useful in the treatment of inflammatory or obstructive airways diseases, resulting, for example, in reduction of tissue damage, airways inflammation, bronchial hyper reactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

S1P4:

The presence of the S1P4 receptor primarily on immune system cells offers a unique opportunity to target this growth factor receptor. S1P4 expression is primarily found in spleen and peripheral blood cells. S1P4 is claimed to be involved in cytokine production from human lymphocytes (Wang et al, FASEB 19: 1731-1733 (2005). Due to its specific expression in lymphatic tissue, it has therapeutic potential in transplantation as well as in inflammatory and immune disorders.

The compounds of the invention are therefore useful in the treatment and/or prevention of diseases of disorders mediated by lymphocyte interactions e.g. transplantation, such as acute or chronic rejection of cell, tissue or organ allo- or xenografts or delayed graft function, graft versus host disease, autoimmune diseases, e.g. rheumatoid arthritis systemic lupus erythematosus, hashimoto's thyroids, multiple sclerosis, myasthenia gravis, diabetes type I or II and the disorder associated therewith, vasculitis, pernicious anemia, Sjoegren syndrome, uveitis, psoriasis, Graves ophthalmology, alopecia areata and others, allergic diseases, e.g. allergic asthma, atopic dermatitis, allergic rhinitis, allergic conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory level injury, inflammatory glomerular injury, atherosclerosis, osteoarthritis, irritant contact dermatitis and further eczematous dermatitises, seborrhoeic dermatitis, cutaneous manifestations of immunologically mediated disorders, inflammatory eye diseases keratoconjunctivitis, myocarditis or hepatitis, ischemia/reperfusion injury, e.g. myocardial infarction, stroke, gut ischemia, real failure or hemorrhagic shock, traumatic shock, others, cancers e.g. T cell lymphomas or T cell leukemias, infectious diseases e.g. toxic shock (e.g. superantigen induced), septic shock, adult respiratory distress syndrome or viral infections e.g. AIDS, viral hepatitis or chronic bacterial infections. Examples of cell, tissue or solid organ transplants include pancreatic islets, stem cells, bone marrow, corneal tussue, neuronal tissue, heart, lung, combined heart-lung, kidney, liver, bowel, pancreas, trachea or oesophagus.

Remedies and/or preventives for diseases caused by vascular contraction or dilation which comprise S1P2 regulators. S1P2 regulators specifically bind to S1P2 and show antagonism or agonism. Thus, an S1P2 antagonist is useful in treating and/or preventing diseases caused by vascular contraction, such as cerebrovascular spasmodic disease following subarachroid hemorrhage or cerebral infarction, cardiovascular spasmodic disease, hypertension, kidney diseases, cardiac infarction, angina, arrhythmia, portal hypertension in association with cirrhosis and varicosity in association with cirrhosis. On the other hand, an S1P2 agonist is useful in treating and/or preventing diseases caused by vascular dilation, such as chronic headache, e.g., hemicrania, tension headache, headache of the mixed type, cluster headaches, hemorrhoid and cardiac diseases.

The invention includes pharmaceutical compositions comprising a regulator of S1P2 expression or activity (and/or a regulator of the activity or expression of a protein in the S1P2 signaling pathway), as well as methods for preparing such compositions by combining one or more such regulators and a pharmaceutically acceptable carrier. Also within the invention are pharmaceutical compositions comprising a regulator identified using the screening assays of the invention packaged with instructions for use. For regulators that are antagonists of S1P2 activity or which reduced S1P2 expression, the instructions would specify use of the pharmaceutical composition for treatment of hematological and cardiovascular diseases, disorders of the peripheral and central nervous system, COPD, asthma, genito-urological disorders and inflammation diseases. For regulators that are agonists of S1P2 activity or increase S1P2 expression, the instructions would specify use of the pharmaceutical composition for treatment of hematological and cardiovascular diseases, disorders of the peripheral and central nervous system, COPD, asthma, genito-urological disorders and inflammation diseases.

Gastrointestinal diseases comprise primary or secondary, acute or chronic diseases of the organs of the gastrointestinal tract which may be acquired or inherited, benign or malignant or metaplastic, and which may affect the organs of the gastrointestinal tract or the body as a whole. They comprise, but are not limited to: (1) disorders of the esophagus like achalasia, vigorous achalasia, dysphagia, cricopharyngeal incoordination, pre-esophageal dysphagia, diffuse esophageal spasm, globus sensation, Barrett's metaplasia and gastroesophageal reflux; (2) disorders of the stomach and duodenum like functional dyspepsia, inflammation of the gastric mucosa, gastritis, stress gastritis, gastric ulcers, duodenal ulcers and neoplasms of the stomach; (3) disorders of the pancreas like acute or chronic pancreatitis, insufficiency of the exocrinic or endocrinic tissues of the pancreas like steatorrhea, diabetes and neoplasms of the exocrine or endocrine pancreas like: (3.1) multiple endocrine neoplasia syndrome, ductal adenocarcinoma, cystadenocarcinoma, islet cell tumors, insulinoma, gastrinoma, carcinoid tumors, glucogonoma, Zollinger-Ellison syndrome, Vipoma syndrome and malabsorption syndrome; (4) disorders of the bowel like chronic inflammatory diseases of the bowel, Crohn's disease, ileus, diarrhea and constipation, colonic inertia, megacolon, malabsorption syndrome, ulcerative colitis; (4.1) functional bowel disorders like irritable bowel syndrome; (4.2) neoplasms of the bowel like familial polyposis, adenocarcinoma, primary malignant lymphoma, carcinoid tumors, Kaposi's sarcoma, polyps and cancer of the colon or rectum.

Medical conditions also include irritable bowel syndrome, chronic constipation, functional dyspepsia, delayed gastric emptying, gastroesophageal reflux disease, gastroparesis, post-operative ileus, intestinal pseudo-obstruction and drug-induced delayed transit.

These compounds may have more specific pharmacological modes of action than currently known S1P receptor ligands. The present invention provides methods for inhibiting S1P3 receptor mediated biological activity. The present invention also provides methods for using S1P3 modulators (agonists and antagonists) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostate cancer; acute lung diseases, adult respiratory distress syndrome (ARDS), acute inflammatory exacerbation of chronic lung diseases, such as asthma, surface epithelial cell injury (e.g., transcomeal freezing or cutaneous burns) and cardiovascular diseases (e.g., ischemia) in a subject in need of such treatment or prevention. Further, the present invention provides compounds and compositions that can, e.g., be used in modulating S1P3 receptor mediated biological activity or treating or preventing diseases such as those mentioned above.

The biological activity mediated by the S1P3 receptor may include, e.g., calcium mobilization, VEGF synthesis, IL-8 synthesis, platelet activation, cell migration, phosphoinositide hydrolysis, inhibition of cAMP formation or actin polymerization. Preferably, the biological activity mediated by the S1P3 receptor includes, but is not limited to, apoptosis, angiogenesis, inhibition of wound healing, inflammation, cancer invasiveness or atherogenesis. Most preferably, the biological activity mediated by the S1P3 receptor is cell proliferation, which may lead to ovarian cancer, peritoneal cancer, endometrial cancer, cervical cancer, breast cancer, colon cancer or prostate cancer. In one embodiment, cell proliferation is stimulated by LPA.

In another embodiment, the biological activity mediated by the S1P3 receptor may include increasing fatty acids levels (e.g., free fatty acids and lyso-phosphatidylcholine) which may lead to acute lung diseases, such as ARDS and acute inflammatory exacerbation of chronic lung diseases like asthma.

In yet another embodiment, compounds that block S1P3 can be potentially effective immunosuppressive agents because activated T cells have S1P3 receptors. S1P3 antagonists may be useful in a variety of autoimmune and related immune disorders, including, but not limited to, systemic lupus erythematosus (SLE), rheumatoid arthritis, non-glomerular nephrosis, psoriasis, chronic active hepatitis, ulcerative colitis, Crohn's disease, Behcet's disease, chronic glomerulonephritis, chronic thrombocytopenic purpura, and autoimmune hemolytic anemia. Additionally, S1P3 antagonists can be used in organ transplantation.

The present invention provides methods for inhibiting S1P3 receptor mediated biological activity. The present invention also provides methods for using S1P3 modulators (agonists and antagonists) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostrate cancer; acute lung diseases, ARDS, acute inflammatory exacerbation of chronic lung diseases, such as asthma, surface epithelial cell injury (e.g., transcomeal freezing or cutaneous burns) and cardiovascular diseases (e.g., ischemia).

Asthma is thought to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to tissue destruction related to the disorder. Other resident cells, such as smooth muscle cells, lung epithelial cells, mucus-producing cells, and nerve cells may also be abnormal in individuals with asthma and may contribute to its pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually make asthma a chronic and disabling disorder requiring long-term management.

Chronic obstructive pulmonary (or airways) disease (COPD) is a condition defined physiologically as airflow obstruction that generally results from a mixture of emphysema and peripheral airway obstruction due to chronic bronchitis [Botstein (1980)]. Emphysema is characterized by destruction of alveolar wails leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does also occur in non-smokers.

The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include bronchiectasis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Other inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics.

(For convenience this particular asthmatic condition is referred to as "wheezy-infant syndrome".) Pulmonary fibrosis and related diseases, such as cystic fibrosis are also applicable to the present invention.

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g., between the hours of about 4 to 6 am, i.e., at a time normally substantially distant from any previously administered symptomatic asthma therapy.

Having regard to their anti-inflammatory activity, in particular, in relation to inhibition of eosinophil activation, agents of the invention are also useful in the treatment of eosinophil-related disorders, e.g., eosinophilia, in particular eosinophil related disorders of the airways (e.g., involving morbid eosinophilic infiltration of pulmonary tissues) including hyper-eosinophilia as it effects the airways and/or lungs, as well as, e.g., eosinophil-related disorders of the airways consequential or concomitant to Löffler's syndrome, eosinophilic pneumonia, parasitic (in particular, metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug reaction.

S1P2 is highly-expressed in various respiratory tissues, such as fetal lung fibroblast IMR-90 cells and lung. The expression in the above-mentioned tissues suggests an association of S1P2 with respiratory diseases. S1P2 can be used to treat or to diagnose diseases of the respiratory system.

The effectiveness of an agent of the invention in inhibiting inflammatory conditions, e.g., in inflammatory airways diseases, may be demonstrated in an animal model, e.g., a mouse or rat model, of airways inflammation or other inflammatory conditions, e.g., as described by Szarka et al, *J Immunol Methods*, 202: 49-57 (1997); Renzi et al, *Am Rev Respir Dis*, 148: 932-939 (1993); Tsuyuki et al., *J Clin Invest*, 96: 2924-2931 (1995); Cernadas et al., *Am J Respir Cell Mol Biol*, 20:1-8 (1999); and Fozard et al., *Eur J Pharmacol*, 438: 183-188 (2002).

Diseases including glomerulo-nephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, ARDS, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis.

The agents of the invention are also useful as co-therapeutic agents for use in combination with other drug substances, such as anti-inflammatory, bronchodilatory, antihistamine or anti-tussive drug substances, particularly in the treatment of obstructive or inflammatory airways diseases, such as those mentioned hereinbefore, e.g., as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance.

Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists, such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists, such as montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine $A_{2B}$ receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds, in free or salt or solvate form, of formula (I) of WO 0075114, which document is incorporated herein by reference, preferably compounds of the Examples thereof, especially a compound of formula

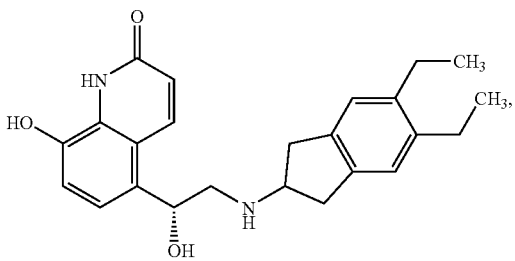

and pharmaceutically acceptable salts thereof, as well as compounds, in free or salt or solvate form, of formula (I) of WO 04/16601, and also compounds of EP 1440966, JP 05025045, WO 93/18007, WO 99/64035, US 2002/0055651, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204, WO 03/93219, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103, WO 05/044787, WO 05/058867, WO 05/065650, WO 05/066140, WO 05/07908, US 2005/5159448, US 2005/171147, WO 05/077361, WO 05/084640, WO 05/089760, WO 05/090287, WO 05/090288, WO 05/092860, WO 05/092887, US 2005/182091, US 2005/209227, US 2005/215542, US 2005/215590, EP 1574501, U.S. Ser. No. 05/256,115, WO 05/102350 and U.S. Ser. No. 05/277,632.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/018422, WO 04/05285 and WO 05/077361.

Suitable dual anti-inflammatory and bronchodilatory drugs include dual beta-2 adrenoceptor agonist/muscarinic antagonists such as those disclosed in US 2004/0167167, US 2004/0242622, US 2005/182092, WO 04/74246 WO 04/74812, WO 04/089892 and U.S. Ser. No. 05/256,114.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D, Takeda antagonists, such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly Claims 18 and 19), WO 00/66558 (particularly Claim 8), WO 00/66559 (particularly Claim 9), WO 04/018425 and WO 04/026873.

In accordance with the foregoing, the invention also provides a method for the treatment of a condition mediated by responsive to activation of the S1P receptor, e.g., an inflammatory or allergic condition, particularly an inflammatory or obstructive airways disease, which comprises administering to a subject, particularly a human subject, in need thereof a compound of formula (I), in free form or in the form of a pharmaceutically acceptable salt. In another aspect the invention provides a compound of formula (II), in free form or in the form of a pharmaceutically acceptable salt, for use in the manufacture of a medicament for the treatment of a condition mediated by responsive to activation of the S1P receptor, particularly an inflammatory or obstructive airways disease.

Formulation and Administration

The agents of the invention may be administered by any appropriate route, e.g., orally, e.g., in the form of a tablet or capsule; parenterally, e.g., intravenously; by inhalation, e.g., in the treatment of inflammatory or obstructive airways disease; intranasally, e.g., in the treatment of allergic rhinitis; topically to the skin, e.g., in the treatment of atopic dermatitis; or rectally, e.g., in the treatment of inflammatory bowel disease.

In a further aspect, the invention also provides a pharmaceutical composition comprising a compound of formula (I), in free form or in the form of a pharmaceutically acceptable salt, optionally together with a pharmaceutically acceptable diluent or carrier therefor. The composition may contain a co-therapeutic agent such as an anti-inflammatory, bronchodilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabiliser, which may be a surfactant.

The invention includes:
  (a) a compound of formula (I) in inhalable form, e.g., in an aerosol or other atomisable composition or in inhalable particulate, e.g., micronised, form;
  (b) an inhalable medicament comprising a compound of formula (I) in inhalable form;
  (c) a pharmaceutical product comprising a compound of formula (I) in inhalable form in association with an inhalation device; and (d) an inhalation device containing a compound of formula (I) in inhalable form.

Dosages of compounds of formula (I) employed in practising the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Assay

The ability of compounds to antagonise S1P activity at $S1P_2$ and $S1P_3$ receptors was examined using GTPγS binding assays.

Membranes preparations were generated from CHO cells expressing either the human $S1P_2$ or $S1P_3$ receptors by homogenisation of the cell suspension and centrifugation at 40 000 g for 30 minutes at 4° C. The supernatant was removed, pellet re-suspended in a 10 mM HEPES, 10 mM EDTA buffer and centrifuged as above. The pellet was re-suspended and stored at −80° C. until use.

Scintillation proximity assay (SPA) technology was used for the GTPγS binding assays. Serial dilutions of test compounds were placed in a 96-well optiplate with 5 nM S1P, 1.25 µg membrane, 0.5 mg SPA beads, 0.3 µM GDP and 100 µM sodium orthovanidate, per well. The assay components were incubated for 2 hours to ensure equilibrium was attained. The assay was started by the addition of 300 pM [$^{35}$S]GTPγS per well and incubated for 60 minutes prior to centrifugation at 3000 rpm for 3 minutes and reading of a Packard TopCount.

Data were analysed using Activity Base (IDBS, UK) by fitting a four parameter logistic curve to generate $IC_{50}$ values for each compound.

CHO Gα16 S1P4:

The assay measures intracellular changes of $Ca^{2+}$ mediated by the endogenous agonist S1P in the CHO S1P4/Gα16 cell clone: CHO (Chinese Hamster Ovary) cells stably expressing human S1P4 cDNA (HSEDG4; GenBank™ Accession Number AJ000479) and promiscuous Gα16 are cultured at 37° C., 5% CO2, and 95% relative humidity. The cells are plated in 384 well black plates (10'000 cells per well). After 24 hours the cells are loaded with Fluo4-AM (1.6 µM in HBSS and 2.5 mM probenicid) for 1 hour at 37° C. After washing, the cells are transferred to the FLIPR. The test compounds are added at different concentrations (≤100 µM) in MSS in the presence BSA at the final concentration of 0.1% and changes in fluorescence are recorded (indication of agonism). S1P is added 20-30 minutes afterwards to the wells at a concentration inducing 80% of the maximal activity ($EC_{80}$). After each addition time points are collected as follows: 20 time points (2 seconds) before the addition of the agonist (Fbase) and 60 time points (1 or 2 seconds) after the addition of the agonist. This allows the determination of the maximal fluorescence (Fmax). The ratio (Fmax−Fbase)/Fbase is plotted against the log of the concentration of the test compounds and the $IC_{50}$ (relative antagonism) is determined using the XLfit-4 software. Compounds with an inhibition <20% are considered "inactive". A dose response curve of the agonist is determined on each plate in parallel.

Compounds of the Examples, herein below, generally have S1P2 $K_B$ values in the GTP-γ-S binding assays below 10 µM. For example, the compounds of Examples 1-1, 1-13, 2-1 and 3-4 have S1P2 $K_B$ values of 0.0008, 0.0019, 0.0036 and 0.0048 µM, respectively. Compounds of the Examples, herein below, generally have S1P4 $IC_{50}$ values in the GTP CHO Gα16 S1P4 assay below 10 µM. For example, the compounds of Examples 1-1, 1-35 and 1-37 have S1P4 $IC_{50}$ values of 0.42, 0.015 and 0.88 µM, respectively.

Preferred compounds of the present invention are as shown in Table 1 below.

EXAMPLES 1-1 TO 1-37

TABLE 1

| Ex. | Structure | Name | [M + H]$^+$ |
|---|---|---|---|
| 1-1 | 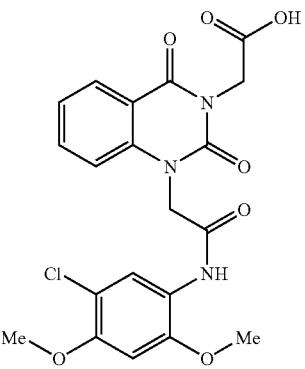 [SMILES: COc1cc(OC)c(NC(=O)Cn2c(=O)n(CC(=O)O)c(=O)c3ccccc32)cc1Cl] | {1-[(5-Chloro-2,4-dimethoxy-phenylcarbamoyl)-methyl]-2,4-dioxo-1,4-dihydro-2H-quinazolin-3-yl}-acetic acid | 448 |

TABLE 1-continued

| Ex. | Structure | Name | [M + H]⁺ |
|---|---|---|---|
| 1-2 | 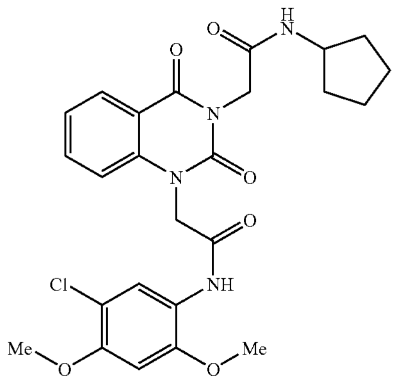 [SMILES: COc1cc(OC)c(NC(=O)Cn2c(=O)n(CC(=O)NC3CCCC3)c(=O)c3ccccc32)cc1Cl] | N-(5-Chloro-2,4-dimethoxy-phenyl)-2-(3-cyclopentylcarbamoylmethyl-2,4-dioxo-3,4-dihydro-2H-quinazolin-1-yl)-acetamide | 515 |
| 1-3 | 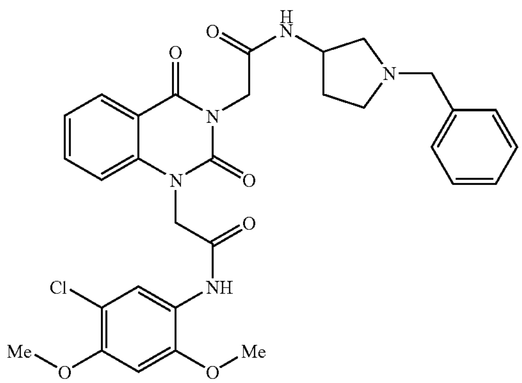 [SMILES: COc1cc(OC)c(NC(=O)Cn2c(=O)n(CC(=O)NC3CCN(Cc4ccccc4)C3)c(=O)c3ccccc32)cc1Cl] | 2-{3-[(1-Benzyl-pyrrolidin-3-ylcarbamoyl)-methyl]-2,4-dioxo-3,4-dihydro-2H-quinazolin-1-yl}-N-(5-chloro-2,4-dimethoxy-phenyl)-acetamide | 607 |
| 1-4 | 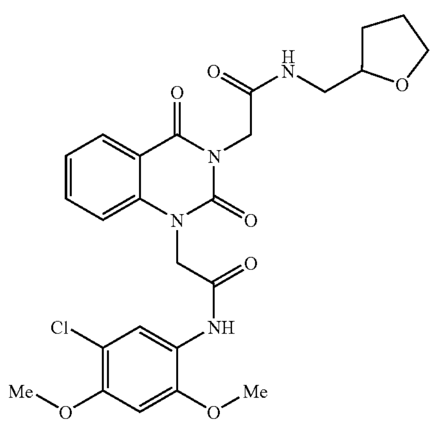 [SMILES: COc1cc(OC)c(NC(=O)Cn2c(=O)n(CC(=O)NCC3CCCO3)c(=O)c3ccccc32)cc1Cl] | N-(5-Chloro-2,4-dimethoxy-phenyl)-2-(2,4-dioxo-3-{[(tetrahydro-furan-2-ylmethyl)-carbamoyl]-methyl}-3,4-dihydro-2H-quinazolin-1-yl)-acetamide | 531 |
| 1-5 | 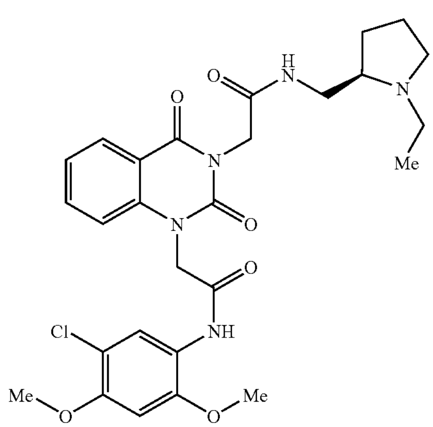 [SMILES: CCN1CCC[C@@H]1CNC(=O)Cn1c(=O)c2ccccc2n(CC(=O)Nc2cc(Cl)c(OC)cc2OC)c1=O] | N-(5-Chloro-2,4-dimethoxy-phenyl)-2-(3-{[((R)-1-ethyl-pyrrolidin-2-ylmethyl)-carbamoyl]-methyl}-2,4-dioxo-3,4-dihydro-2H-quinazolin-1-yl)-acetamide | 558 |

TABLE 1-continued

| Ex. | Structure | Name | [M + H]+ |
|---|---|---|---|
| 1-6 | 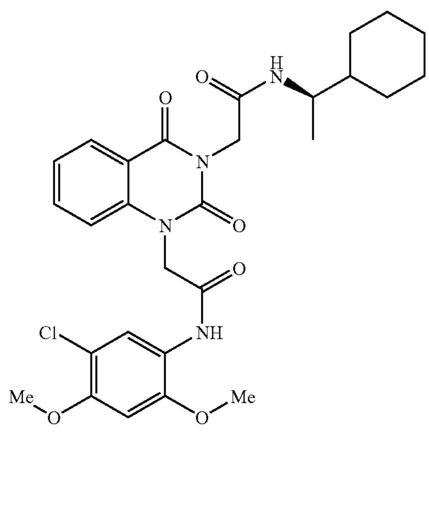 [SMILES: COc1cc(OC)c(NC(=O)Cn2c(=O)n(CC(=O)N[C@H](C)C3CCCCC3)c(=O)c3ccccc32)cc1Cl] | N-(5-Chloro-2,4-dimethoxy-phenyl)-2-{3-[((R)-1-cyclohexyl-ethylcarbamoyl)-methyl]-2,4-dioxo-3,4-dihydro-2H-quinazolin-1-yl}-acetamide | 558 |
| 1-7 | 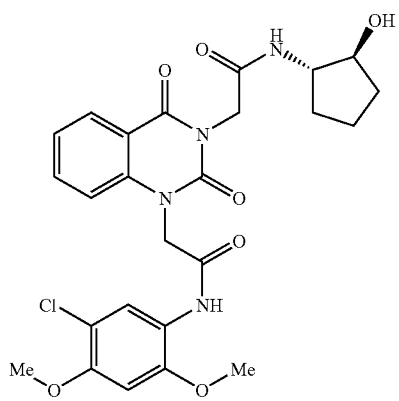 [SMILES: COc1cc(OC)c(NC(=O)Cn2c(=O)n(CC(=O)N[C@H]3CCC[C@@H]3O)c(=O)c3ccccc32)cc1Cl] | N-(5-Chloro-2,4-dimethoxy-phenyl)-2-{3-[((1S,2S)-2-hydroxy-cyclopentylcarbamoyl)-methyl]-2,4-dioxo-3,4-dihydro-2H-quinazolin-1-yl}-acetamide | 531 |
| 1-8 | 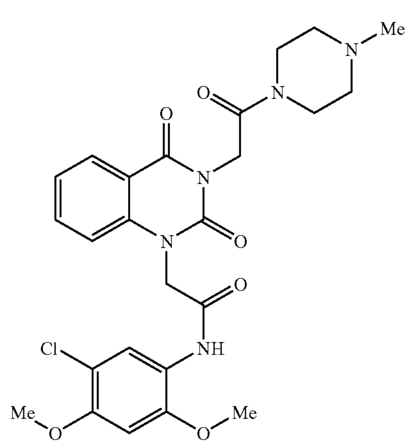 [SMILES: COc1cc(OC)c(NC(=O)Cn2c(=O)n(CC(=O)N3CCN(C)CC3)c(=O)c3ccccc32)cc1Cl] | N-(5-Chloro-2,4-dimethoxy-phenyl)-2-{3-[2-(4-methyl-piperazin-1-yl)-2-oxo-ethyl]-2,4-dioxo-3,4-dihydro-2H-quinazolin-1-yl}-acetamide | 530 |

TABLE 1-continued

| Ex. | Structure | Name | [M + H]⁺ |
|---|---|---|---|
| 1-9 | 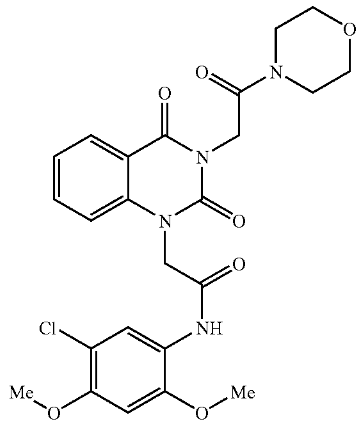 [SMILES: COc1cc(OC)c(NC(=O)Cn2c(=O)n(CC(=O)N3CCOCC3)c(=O)c3ccccc32)cc1Cl] | N-(5-Chloro-2,4-dimethoxy-phenyl)-2-[3-(2-morpholin-4-yl-2-oxo-ethyl)-2,4-dioxo-3,4-dihydro-2H-quinazolin-1-yl]-acetamide | 517 |
| 1-10 | 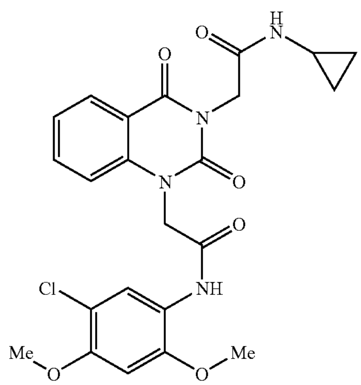 [SMILES: COc1cc(OC)c(NC(=O)Cn2c(=O)n(CC(=O)NC3CC3)c(=O)c3ccccc32)cc1Cl] | N-(5-Chloro-2,4-dimethoxy-phenyl)-2-(3-cyclopropylcarbamoylmethyl-2,4-dioxo-3,4-dihydro-2H-quinazolin-1-yl)-acetamide | 487 |
| 1-11 | 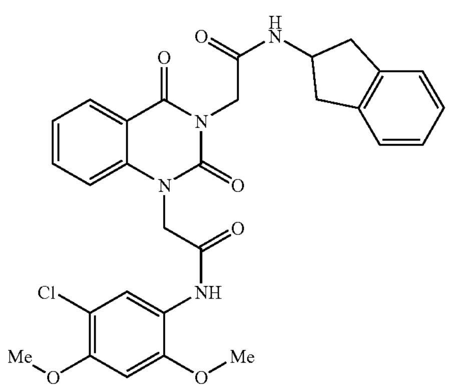 [SMILES: COc1cc(OC)c(NC(=O)Cn2c(=O)n(CC(=O)NC3Cc4ccccc4C3)c(=O)c3ccccc32)cc1Cl] | N-(5-Chloro-2,4-dimethoxy-phenyl)-2-[3-(indan-2-ylcarbamoylmethyl)-2,4-dioxo-3,4-dihydro-2H-quinazolin-1-yl]-acetamide | 563 |
| 1-12 | 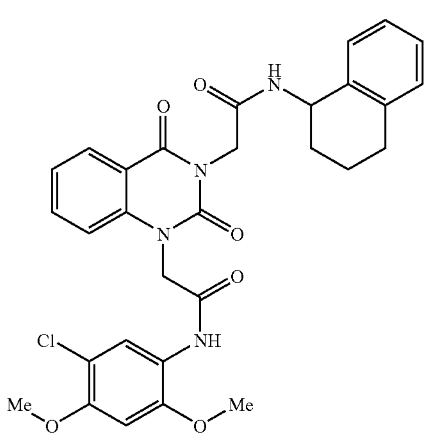 [SMILES: COc1cc(OC)c(NC(=O)Cn2c(=O)n(CC(=O)NC3CCCc4ccccc43)c(=O)c3ccccc32)cc1Cl] | N-(5-Chloro-2,4-dimethoxy-phenyl)-2-{2,4-dioxo-3-[(1,2,3,4-tetrahydro-naphthalen-1-ylcarbamoyl)-methyl]-3,4-dihydro-2H-quinazolin-1-yl}-acetamide | 577 |

TABLE 1-continued

| Ex. | Structure | Name | [M + H]+ |
|---|---|---|---|
| 1-13 | 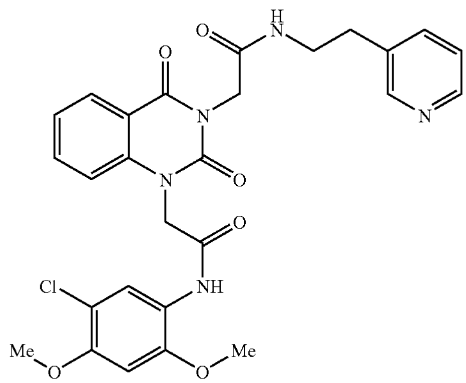 [SMILES: COc1cc(OC)c(NC(=O)Cn2c(=O)n(CC(=O)NCCc3cccnc3)c(=O)c3ccccc32)cc1Cl] | N-(5-Chloro-2,4-dimethoxy-phenyl)-2-{2,4-dioxo-3-[(2-pyridin-3-yl-ethylcarbamoyl)-methyl]-3,4-dihydro-2H-quinazolin-1-yl}-acetamide | 552 |
| 1-14 | 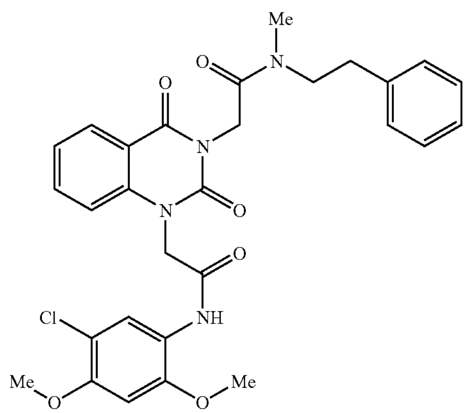 [SMILES: COc1cc(OC)c(NC(=O)Cn2c(=O)n(CC(=O)N(C)CCc3ccccc3)c(=O)c3ccccc32)cc1Cl] | N-(5-Chloro-2,4-dimethoxy-phenyl)-2-{3-[(methyl-phenethyl-carbamoyl)-methyl]-2,4-dioxo-3,4-dihydro-2H-quinazolin-1-yl}-acetamide | 565 |
| 1-15 | 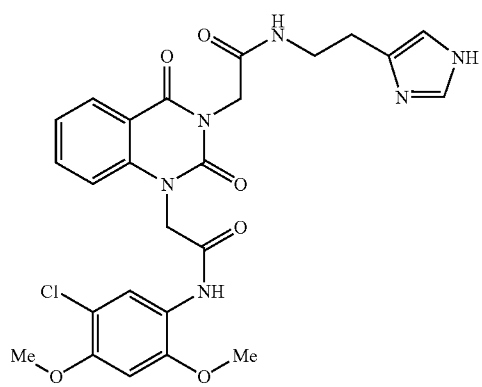 [SMILES: COc1cc(OC)c(NC(=O)Cn2c(=O)n(CC(=O)NCCc3c[nH]cn3)c(=O)c3ccccc32)cc1Cl] | N-(5-Chloro-2,4-dimethoxy-phenyl)-2-(3-{[2-(1H-imidazol-4-yl)-ethylcarbamoyl]-methyl}-2,4-dioxo-3,4-dihydro-2H-quinazolin-1-yl)-acetamide | 541 |
| 1-16 | 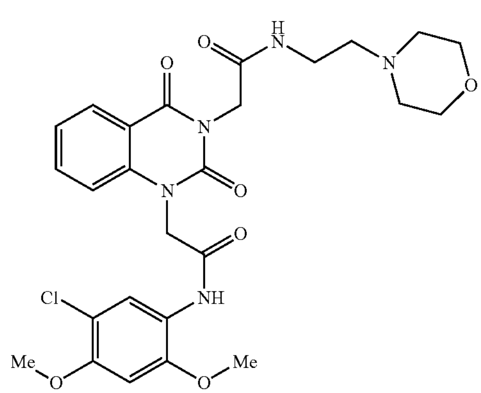 [SMILES: COc1cc(OC)c(NC(=O)Cn2c(=O)n(CC(=O)NCCN3CCOCC3)c(=O)c3ccccc32)cc1Cl] | N-(5-Chloro-2,4-dimethoxy-phenyl)-2-{3-[(2-morpholin-4-yl-ethylcarbamoyl)-methyl]-2,4-dioxo-3,4-dihydro-2H-quinazolin-1-yl}-acetamide | 561 |

TABLE 1-continued

| Ex. | Structure | Name | [M + H]⁺ |
|---|---|---|---|
| 1-17 | 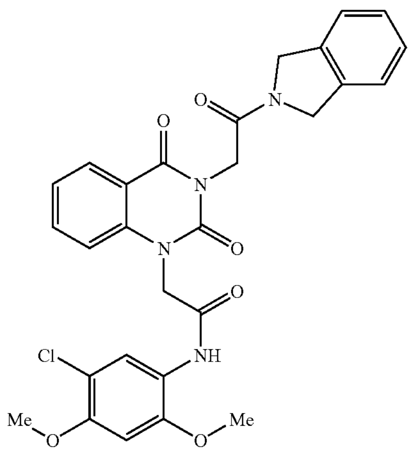 [SMILES: COc1cc(OC)c(NC(=O)Cn2c(=O)n(CC(=O)N3Cc4ccccc4C3)c(=O)c3ccccc32)cc1Cl] | N-(5-Chloro-2,4-dimethoxy-phenyl)-2-{3-[2-(1,3-dihydro-isoindol-2-yl)-2-oxo-ethyl]-2,4-dioxo-3,4-dihydro-2H-quinazolin-1-yl}-acetamide | 549 |
| 1-18 | 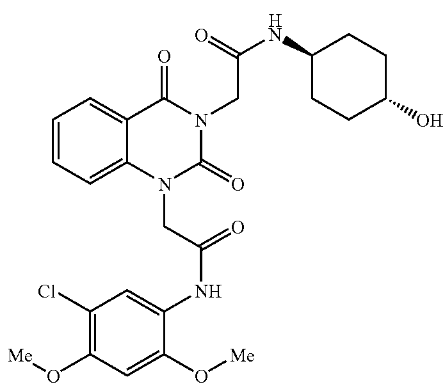 [SMILES: COc1cc(OC)c(NC(=O)Cn2c(=O)n(CC(=O)N[C@H]3CC[C@H](O)CC3)c(=O)c3ccccc32)cc1Cl] | N-(5-Chloro-2,4-dimethoxy-phenyl)-2-{3-[(4-hydroxy-cyclohexylcarbamoyl)-methyl]-2,4-dioxo-3,4-dihydro-2H-quinazolin-1-yl}-acetamide | 545 |
| 1-19 | 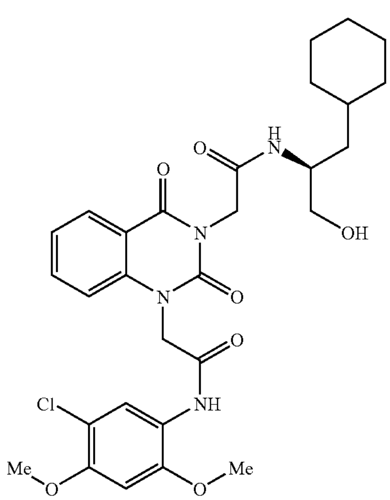 [SMILES: COc1cc(OC)c(NC(=O)Cn2c(=O)n(CC(=O)N[C@H](CO)CC3CCCCC3)c(=O)c3ccccc32)cc1Cl] | N-(5-Chloro-2,4-dimethoxy-phenyl)-2-{3-[((S)-1-cyclohexylmethyl-2-hydroxy-ethylcarbamoyl)-methyl]-2,4-dioxo-3,4-dihydro-2H-quinazolin-1-yl}-acetamide | 587 |

TABLE 1-continued
| Ex. | Structure | Name | [M + H]+ |
|---|---|---|---|
| 1-20 | 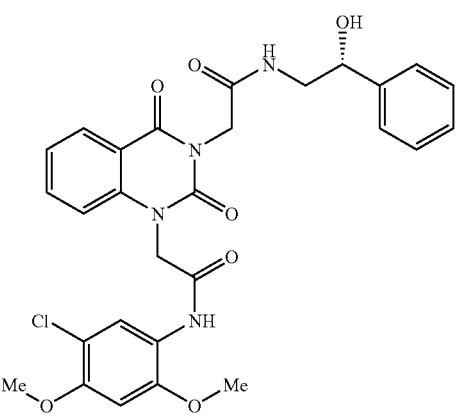 [SMILES: COc1cc(OC)c(NC(=O)Cn2c(=O)n(CC(=O)NC[C@H](O)c3ccccc3)c(=O)c3ccccc32)cc1Cl] | N-(5-Chloro-2,4-dimethoxy-phenyl)-2-{3-[((R)-2-hydroxy-2-phenyl-ethylcarbamoyl)-methyl]-2,4-dioxo-3,4-dihydro-2H-quinazolin-1-yl}-acetamide | 567 |
| 1-21 | 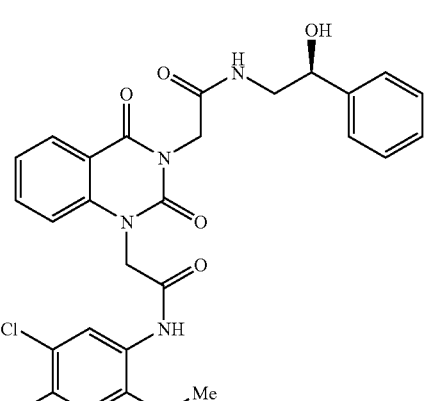 | N-(5-Chloro-2,4-dimethoxy-phenyl)-2-{3-[((S)-2-hydroxy-2-phenyl-ethylcarbamoyl)-methyl]-2,4-dioxo-3,4-dihydro-2H-quinazolin-1-yl}-acetamide | 567 |
| 1-22 | 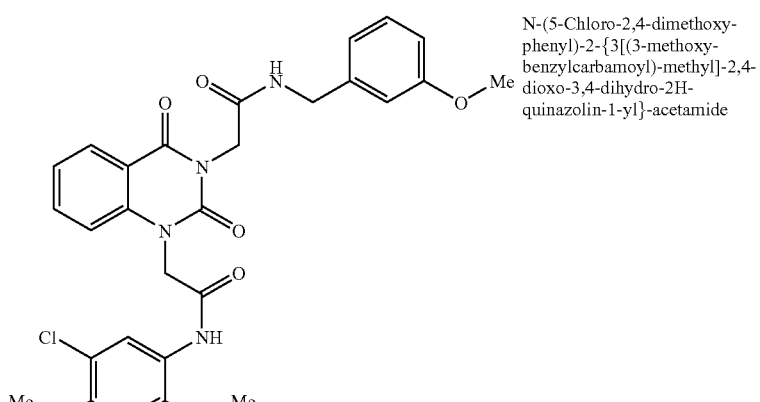 | N-(5-Chloro-2,4-dimethoxy-phenyl)-2-{3[(3-methoxy-benzylcarbamoyl)-methyl]-2,4-dioxo-3,4-dihydro-2H-quinazolin-1-yl}-acetamide | 567 |

TABLE 1-continued

| Ex. | Structure | Name | [M + H]+ |
|---|---|---|---|
| 1-23 | 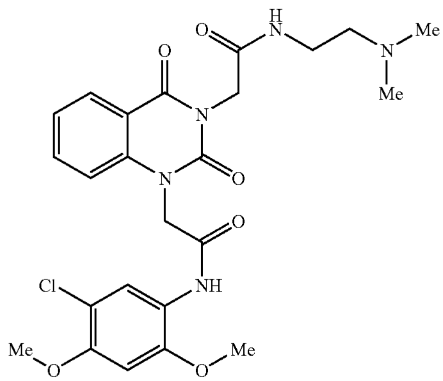 [SMILES: COc1cc(OC)c(NC(=O)Cn2c(=O)n(CC(=O)NCCN(C)C)c(=O)c3ccccc32)cc1Cl] | N-(5-Chloro-2,4-dimethoxy-phenyl)-2-{3-[(2-dimethylamino-ethylcarbamoyl)-methyl]-2,4-dioxo-3,4-dihydro-2H-quinazolin-1-yl}-acetamide | 518 |
| 1-24 | 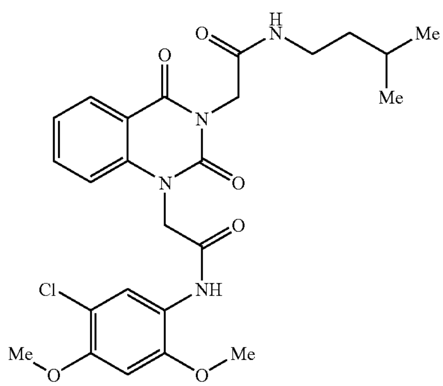 [SMILES: COc1cc(OC)c(NC(=O)Cn2c(=O)n(CC(=O)NCCC(C)C)c(=O)c3ccccc32)cc1Cl] | N-(5-Chloro-2,4-dimethoxy-phenyl)-2-{3-[(3-methyl-butylcarbamoyl)-methyl]-2,4-dioxo-3,4-dihydro-2H-quinazolin-1-yl}-acetamide | 517 |
| 1-25 | 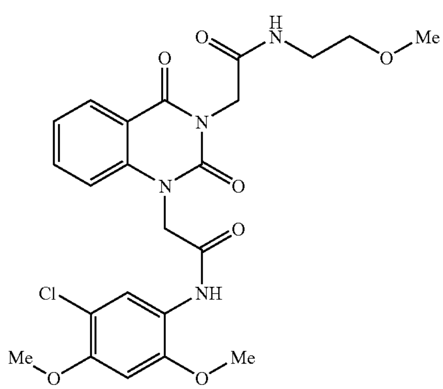 [SMILES: COCCNC(=O)Cn1c(=O)c2ccccc2n(CC(=O)Nc2cc(Cl)c(OC)cc2OC)c1=O] | N-(5-Chloro-2,4-dimethoxy-phenyl)-2-{3-[(2-methoxy-ethylcarbamoyl)-methyl]-2,4-dioxo-3,4-dihydro-2H-quinazolin-1-yl}-acetamide | 505 |
| 1-26 | 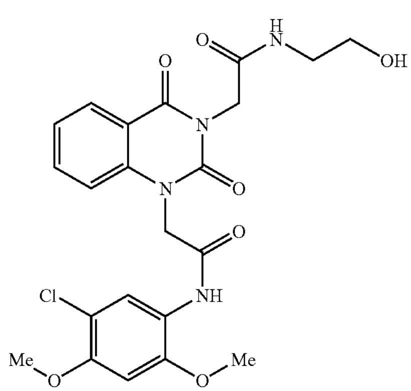 [SMILES: COc1cc(OC)c(NC(=O)Cn2c(=O)n(CC(=O)NCCO)c(=O)c3ccccc32)cc1Cl] | N-(5-Chloro-2,4-dimethoxy-phenyl)-2-{3-[(2-hydroxy-ethylcarbamoyl)-methyl]-2,4-dioxo-3,4-dihydro-2H-quinazolin-1-yl}-acetamide | 491 |

TABLE 1-continued

| Ex. | Structure | Name | [M + H]⁺ |
|---|---|---|---|
| 1-27 | 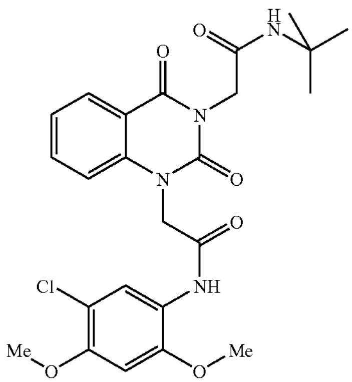 [SMILES: COc1cc(OC)c(NC(=O)Cn2c(=O)n(CC(=O)NC(C)(C)C)c(=O)c3ccccc32)cc1Cl] | 2-[3-(tert-Butylcarbamoyl-methyl)-2,4-dioxo-3,4-dihydro-2H-quinazolin-1-yl]-N-(5-chloro-2,4-dimethoxy-phenyl)-acetamide | 503 |
| 1-28 | 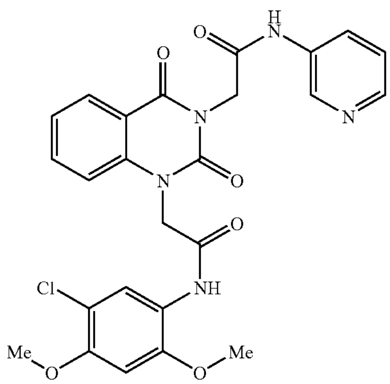 [SMILES: COc1cc(OC)c(NC(=O)Cn2c(=O)n(CC(=O)Nc3cccnc3)c(=O)c3ccccc32)cc1Cl] | N-(5-Chloro-2,4-dimethoxy-phenyl)-2-[2,4-dioxo-3-(pyridin-3-ylcarbamoylmethyl)-3,4-dihydro-2H-quinazolin-1-yl]-acetamide | 524 |
| 1-29 | 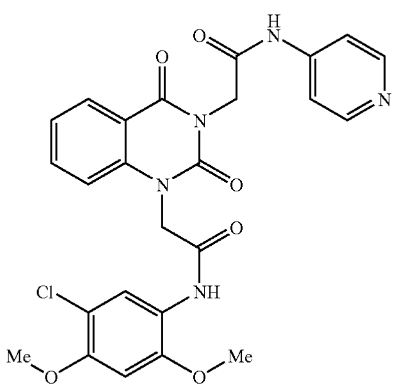 [SMILES: COc1cc(OC)c(NC(=O)Cn2c(=O)n(CC(=O)Nc3ccncc3)c(=O)c3ccccc32)cc1Cl] | N-(5-Chloro-2,4-dimethoxy-phenyl)-2-[2,4-dioxo-3-(pyridine-4-ylcarbamoylmethyl)-3,4-dihydro-2H-quinazolin-1-yl]-acetamide | 524 |
| 1-30 | 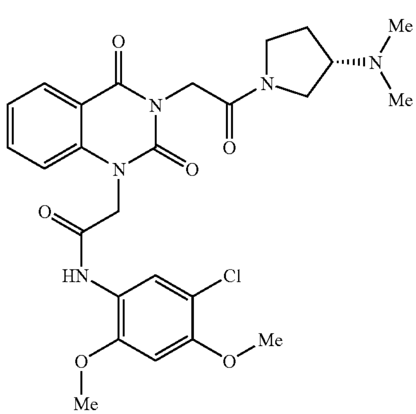 [SMILES: COc1cc(OC)c(NC(=O)Cn2c(=O)n(CC(=O)N3CC[C@H](N(C)C)C3)c(=O)c3ccccc32)cc1Cl] | N-(5-Chloro-2,4-dimethoxy-phenyl)-2-{3-[2-((S)-3-dimethylamino-pyrrolidin-1-yl)-2-oxo-ethyl]-2,4-dioxo-3,4-dihydro-2H-quinazolin-1-yl}-acetamide | 544 |

TABLE 1-continued

| Ex. | Structure | Name | [M + H]+ |
|---|---|---|---|
| 1-31 | 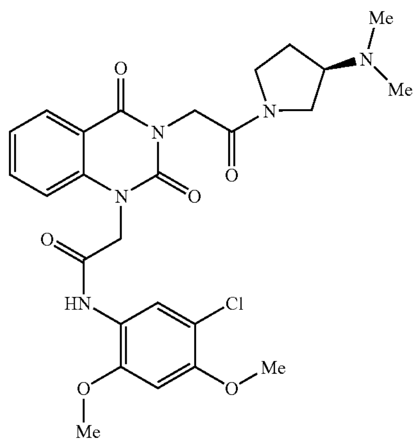 [SMILES: COc1cc(OC)c(NC(=O)Cn2c(=O)n(CC(=O)N3CC[C@@H](N(C)C)C3)c(=O)c3ccccc32)cc1Cl] | N-(5-Chloro-2,4-dimethoxy-phenyl)-2-{3-[2-((R)-3-dimethylamino-pyrrolidin-1-yl)-2-oxo-ethyl]-2,4-dioxo-3,4-dihydro-2H-quinazolin-1-yl}-acetamide | 544 |
| 1-32 | 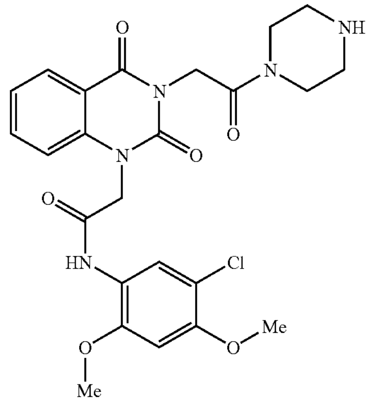 [SMILES: COc1cc(OC)c(NC(=O)Cn2c(=O)n(CC(=O)N3CCNCC3)c(=O)c3ccccc32)cc1Cl] | N-(5-Chloro-2,4-dimethoxy-phenyl)-2-[2,4-dioxo-3-(2-oxo-2-piperazin-1-yl-ethyl)-3,4-dihydro-2H-quinazolin-1-yl]-acetamide | 516 |
| 1-33 | 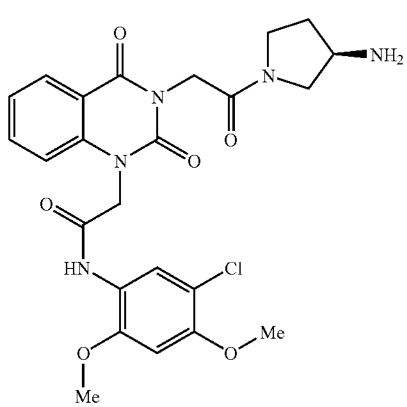 [SMILES: COc1cc(OC)c(NC(=O)Cn2c(=O)n(CC(=O)N3CC[C@@H](N)C3)c(=O)c3ccccc32)cc1Cl] | 2-{3-[2-((R)-3-Amino-pyrrolidin-1-yl)-2-oxo-ethyl]-2,4-dioxo-3,4-dihydro-2H-quinazolin-1-yl}-N-(5-chloro-2,4-dimethoxy-phenyl)-acetamide | 516 |

TABLE 1-continued

| Ex. | Structure | Name | [M + H]+ |
|---|---|---|---|
| 1-34 | 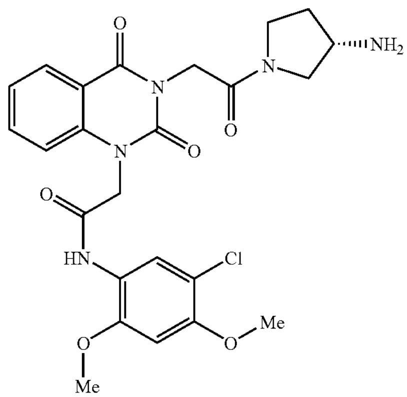 [SMILES: COc1cc(OC)c(NC(=O)Cn2c(=O)n(CC(=O)N3CC[C@H](N)C3)c(=O)c3ccccc32)cc1Cl] | 2-{3-[2-((S)-3-Amino-pyrrolidin-1-yl)-2-oxo-ethyl]-2,4-dioxo-3,4-dihydro-2H-quinazolin-1-yl}-N-(5-chloro-2,4-dimethoxy-phenyl)-acetamide | 516 |
| 1-35 | 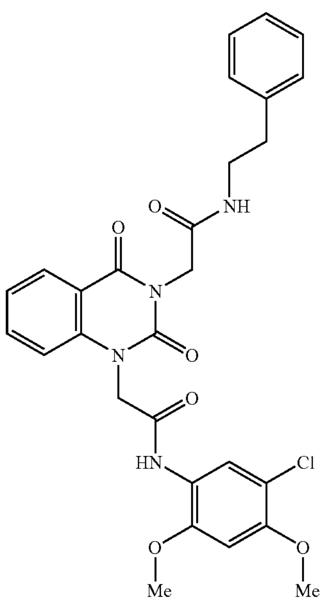 [SMILES: COc1cc(OC)c(NC(=O)Cn2c(=O)n(CC(=O)NCCc3ccccc3)c(=O)c3ccccc32)cc1Cl] | 2-{1-[(5-Chloro-2,4-dimethoxy-phenylcarbamoyl)-methyl]-2,4-dioxo-1,4-dihydro-2H-quinazolin-3-yl}-N-phenethyl-acetamide | 551 |
| 1-36 | 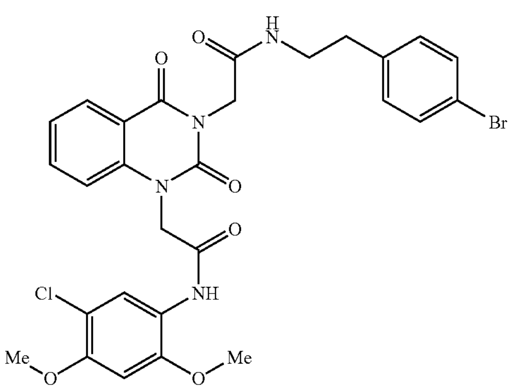 [SMILES: COc1cc(OC)c(NC(=O)Cn2c(=O)n(CC(=O)NCCc3ccc(Br)cc3)c(=O)c3ccccc32)cc1Cl] | 2-(3-{[2-4-Bromo-phenyl)-ethylcarbamoyl]-methyl}-2,4-dioxo-3,4-dihydro-2H-quinazolin-1-yl)-N-(5-chloro-2,4-dimethoxy-phenyl)-acetamide | 631 |

TABLE 1-continued

| Ex. | Structure | Name | [M + H]+ |
|---|---|---|---|
| 1-37 | 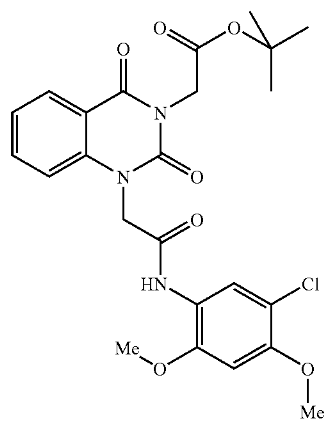 [SMILES: COc1cc(OC)c(NC(=O)Cn2c(=O)n(CC(=O)OC(C)(C)C)c(=O)c3ccccc32)cc1Cl] | {1-[(5-Chloro-2,4-dimethoxy-phenylcarbamoyl)-methyl]-2,4-dioxo-1,4-dihydro-2H-quinazolin-3-yl}-acetic acid tert butyl ester | 504 |

Further preferred compounds of the present invention are as shown in Table 2 below.

EXAMPLES 2-1 TO 2-4

TABLE 2

| Ex. | Structure | Name | [M + H]+ |
|---|---|---|---|
| 2-1 | 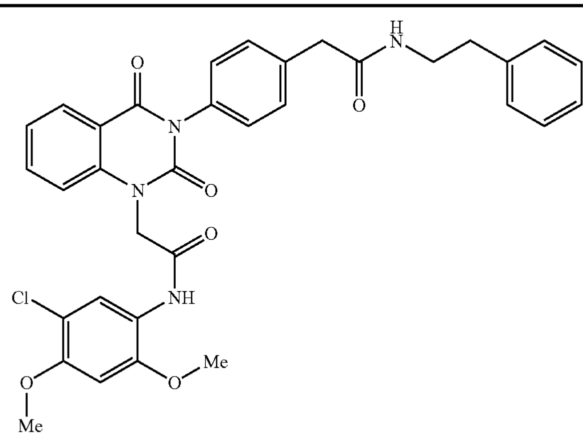 | 2-(4-{1-[(5-Chloro-2,4-dimethoxy-phenylcarbamoyl)-methyl]-2,4-dioxo-1,4-dihydro-2H-quinazolin-3-yl}-phenyl)-N-phenethyl-acetamide | 627 |
| 2-2 | 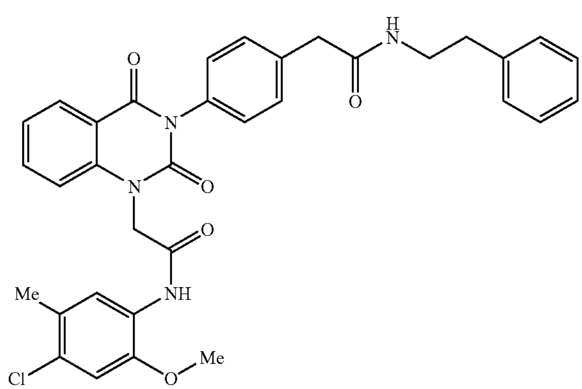 [SMILES: COc1cc(Cl)c(C)cc1NC(=O)Cn1c(=O)n(-c2ccc(CC(=O)NCCc3ccccc3)cc2)c(=O)c2ccccc21] | 2-(4-{1-[(4-Chloro-2-methoxy-5-methyl-phenylcarbamoyl)-methyl]-2,4-dioxo-1,4-dihydro-2H-quinazolin-3-yl}-phenyl)-N-phenethyl-acetamide | 611 |

TABLE 2-continued

| Ex. | Structure | Name | [M + H]⁺ |
|---|---|---|---|
| 2-3 | 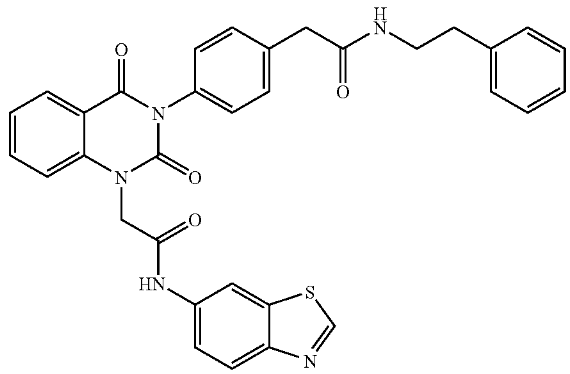 [SMILES: O=C(Cc1ccc(-n2c(=O)c3ccccc3n(CC(=O)Nc3ccc4ncsc4c3)c2=O)cc1)NCCc1ccccc1] | 2-{4-[1-Benzothiazol-6-ylcarbamoylmethyl)-2,4-dioxo-1,4-dihydro-2H-quinazolin-3-yl]-phenyl}-N-phenethyl-acetamide | 590 |
| 2-4 | 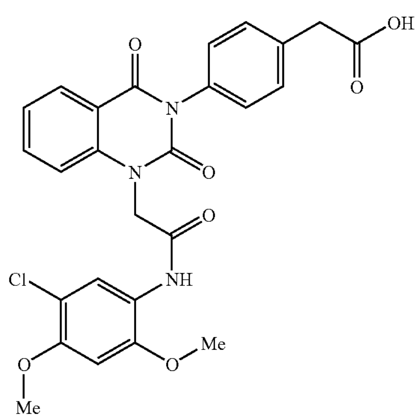 [SMILES: COc1cc(OC)c(NC(=O)Cn2c(=O)n(-c3ccc(CC(=O)O)cc3)c(=O)c3ccccc32)cc1Cl] | (4-{1-[(5-Chloro-2,4-dimethoxy-phenylcarbamoyl)-methyl]-2,4-dioxo-1,4-dihydro-2H-quinazolin-3-yl}-phenyl)-acetic acid | 524 |

Further preferred compounds of the present invention are shown as Examples 3-1 and 3-10 to 3-17 in Table 3 below. Compounds 3-2 to 3-9 are known compounds.

COMPOUNDS 3-2 TO 3-9 AND EXAMPLES 3-1 AND 3-10 TO 3-17

TABLE 3

| | Structure | Chemical Name | [M + H]⁺ |
|---|---|---|---|
| 3-1 | 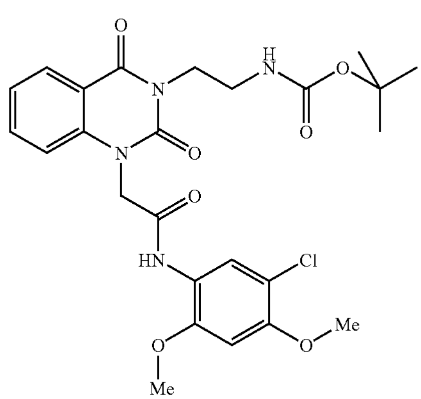 [SMILES: COc1cc(OC)c(NC(=O)Cn2c(=O)n(CCNC(=O)OC(C)(C)C)c(=O)c3ccccc32)cc1Cl] | (2-{1-[(5-Chloro-2,4-dimethoxy-phenylcarbamoyl)-methyl]-2,4-dioxo-1,4-dihydro-2H-quinazolin-3-yl}-ethyl)-carbamic acid tert-butyl ester | 533 |

TABLE 3-continued

| | Structure | Chemical Name | [M + H]+ |
|---|---|---|---|
| 3-2 | 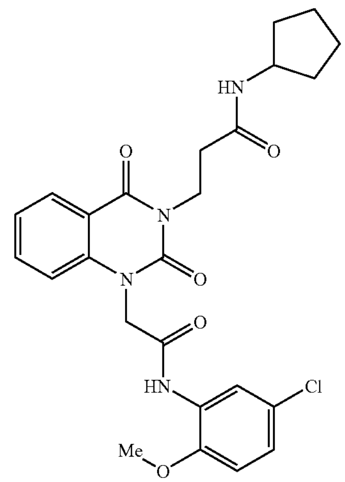 [SMILES: COc1ccc(Cl)cc1NC(=O)Cn1c(=O)n(CCC(=O)NC2CCCC2)c(=O)c2ccccc21] | 3-{1-[(5-Chloro-2-methoxy-phenylcarbamoyl)-methyl]-2,4-dioxo-1,4-dihydro-2H-quinazolin-3-yl}-N-cyclopentyl-propionamide | |
| 3-3 | 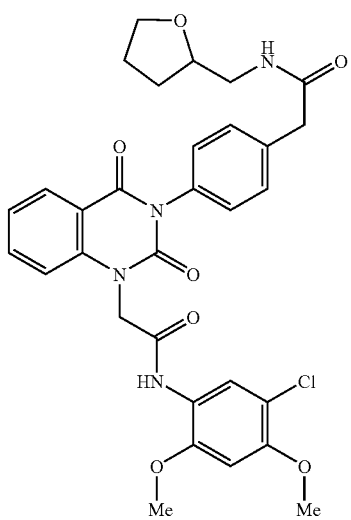 [SMILES: COc1cc(OC)c(NC(=O)Cn2c(=O)n(-c3ccc(CC(=O)NCC4CCCO4)cc3)c(=O)c3ccccc32)cc1Cl] | N-(5-Chloro-2,4-dimethoxy-phenyl)-2-[2,4-dioxo-3-(4-{[(tetrahydro-furan-2-ylmethyl)-carbamoyl]-methyl}-phenyl)-3,4-dihydro-2H-quinazolin-1-yl]-acetamide | |
| 3-4 | 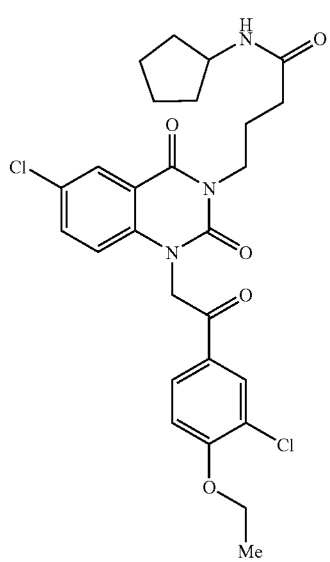 [SMILES: CCOc1ccc(C(=O)Cn2c(=O)n(CCCC(=O)NC3CCCC3)c(=O)c3cc(Cl)ccc32)cc1Cl] | 4-{6-Chloro-1-[2-(3-chloro-4-ethoxy-phenyl)-2-oxo-ethyl]-2,4-dioxo-1,4-dihydro-2H quinazolin-3-yl}-N-cyclopentyl-butyramide | |

TABLE 3-continued
| Structure | Chemical Name | [M + H]+ |
|---|---|---|
| 3-5 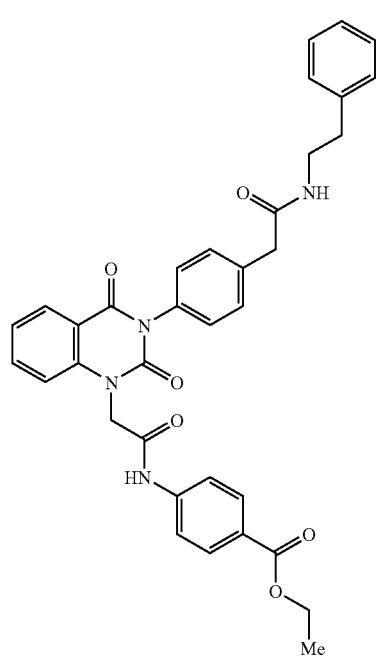 [SMILES: CCOC(=O)c1ccc(NC(=O)Cn2c(=O)n(-c3ccc(CC(=O)NCCc4ccccc4)cc3)c(=O)c3ccccc32)cc1] | 4-(2-{2,4-Dioxo-3-[4-(phenethylcarbamoyl-methyl)phenyl]-3,4-dihydro-2H-quinazolin-1-yl}-acetylamino)-benzoic acid ethyl ester | |
| 3-6 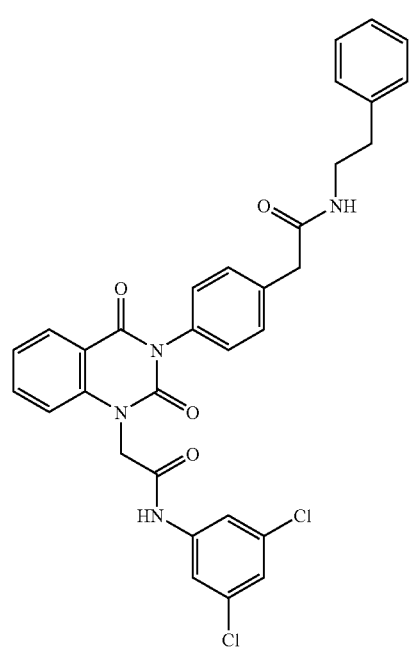 [SMILES: O=C(Cc1ccc(-n2c(=O)c3ccccc3n(CC(=O)Nc3cc(Cl)cc(Cl)c3)c2=O)cc1)NCCc1ccccc1] | N-(3,5-Dichloro-phenyl)-2-{2,4-dioxo-3-[4-(phenethycarbamoyl-methyl)-phenyl]-3,4-dihydro-2H-quinazolin-1-yl}-acetamide | |

TABLE 3-continued

| | Structure | Chemical Name | [M + H]+ |
|---|---|---|---|
| 3-7 | 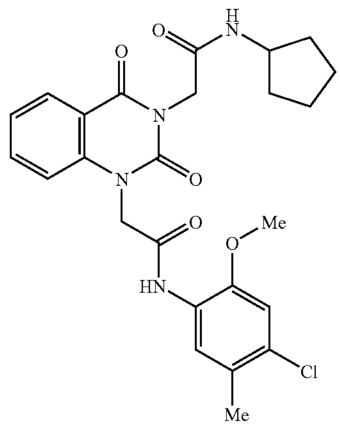 [SMILES: COc1cc(Cl)c(C)cc1NC(=O)Cn1c(=O)n(CC(=O)NC2CCCC2)c(=O)c2ccccc21] | 2-{1-[(4-Chloro-2-methoxy-5-methyl-phenylcarbamoyl)-methyl]-2,4-dioxo-1,4-dihydro-2H-quinazolin-3-yl}-N-cyclopentyl-acetamide | |
| 3-8 | 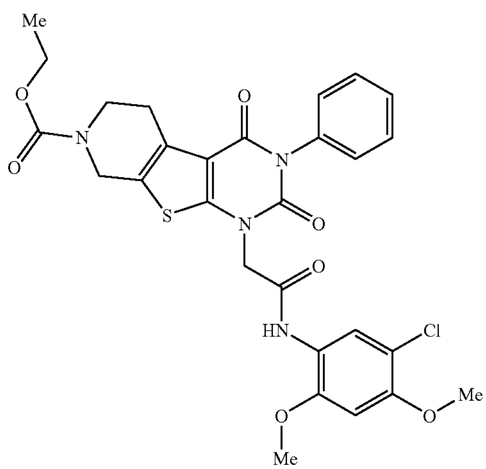 [SMILES: CCOC(=O)N1CCc2c(sc3c2c(=O)n(-c2ccccc2)c(=O)n3CC(=O)Nc2cc(Cl)c(OC)cc2OC)C1] | 1-[(5-Chloro-2,4-dimethoxy-phenylcarbamoyl)-methyl]-2,4-dioxo-3-phenyl-1,3,4,5,6,8-hexahydro-2H-pyrido[4',3':4,5]thieno[2,3-d]pyrimidine-7-carboxylic acid ethyl ester | |
| 3-9 | 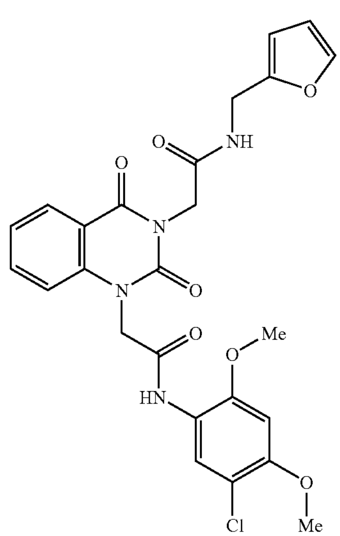 [SMILES: COc1cc(OC)c(NC(=O)Cn2c(=O)n(CC(=O)NCc3ccco3)c(=O)c3ccccc32)cc1Cl] | 2-{1-[(5-Chloro-2,4-dimethoxy-phenylcarbamoyl)-methyl]-2,4-dioxo-1,4-dihydro-2H-quinazolin-3-yl}-N-furan-2-ylmethyl-acetamide | |

TABLE 3-continued

| | Structure | Chemical Name | [M + H]⁺ |
|---|---|---|---|
| 3-10 | 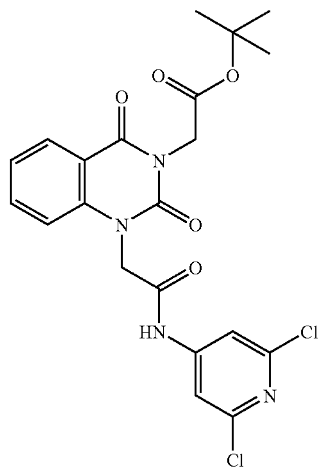 [SMILES: CC(C)(C)OC(=O)Cn1c(=O)c2ccccc2n(CC(=O)Nc2cc(Cl)nc(Cl)c2)c1=O] | {1-[(2,6-Dichloro-pyridin-4-ylcarbamoyl)-methyl]-2,4-dioxo-1,4-dihydro-2H-quinazolin-3-yl}-acetic acid tert-butyl ester | 479 |
| 3-11 | 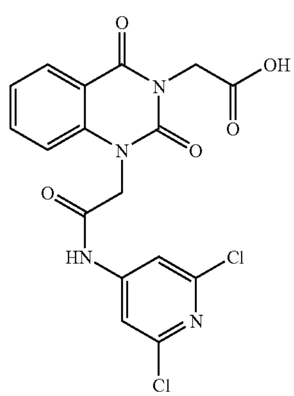 [SMILES: O=C(O)Cn1c(=O)c2ccccc2n(CC(=O)Nc2cc(Cl)nc(Cl)c2)c1=O] | {1-[(2,6-Dichloro-pyridin-4-ylcarbamoyl)-methyl]-2,4-dioxo-1,4-dihydro-2H-quinazolin-3-yl}-acetic acid | 422 |
| 3-12 | 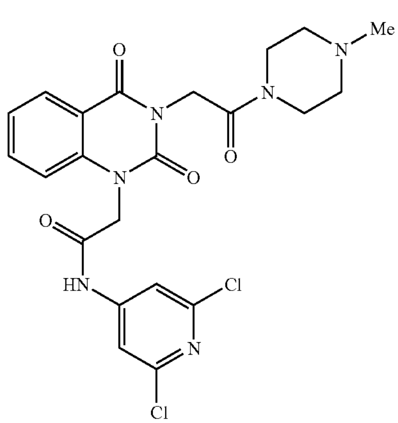 [SMILES: CN1CCN(C(=O)Cn2c(=O)c3ccccc3n(CC(=O)Nc3cc(Cl)nc(Cl)c3)c2=O)CC1] | N-(2,6-Dichloro-pyridin-4-yl)-2-{3-[2-(4-methyl-piperazin-1-yl)-2-oxo-ethyl]-2,4-dioxo-3,4-dihydro-2H-quinazolin-1-yl}-acetamide | 505 |

TABLE 3-continued

| | Structure | Chemical Name | [M + H]+ |
|---|---|---|---|
| 3-13 | 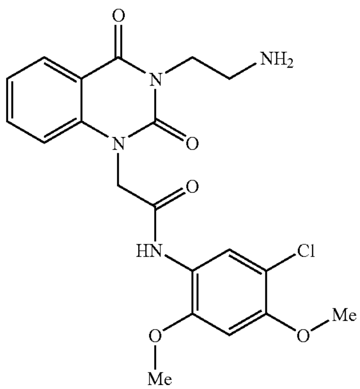 [SMILES: COc1cc(OC)c(NC(=O)Cn2c(=O)n(CCN)c(=O)c3ccccc32)cc1Cl] | 2-[3-(2-Amino-ethyl)-2,4-dioxo-3,4-dihydro-2H-quinazolin-1-yl]-N-(5-chloro-2,4-dimethoxy-phenyl)-acetamide | 433 |
| 3-14 | 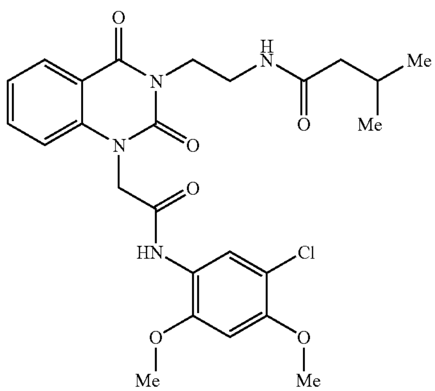 [SMILES: COc1cc(OC)c(NC(=O)Cn2c(=O)n(CCNC(=O)CC(C)C)c(=O)c3ccccc32)cc1Cl] | N-(2-{1-[(5-Chloro-2,4-dimethoxy-phenylcarbamoyl)-methyl]-2,4-dioxo-1,4-dihydro-2H-quinazolin-3-yl}-ethyl)-3-methyl-butyramide | 517.3 |
| 3-15 | 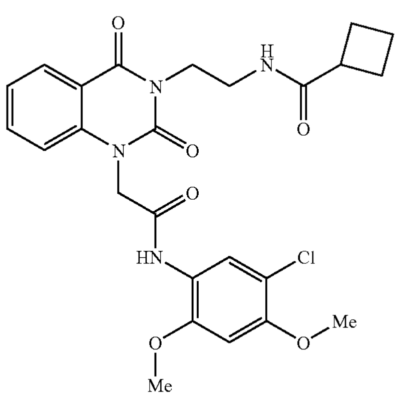 [SMILES: COc1cc(OC)c(NC(=O)Cn2c(=O)n(CCNC(=O)C3CCC3)c(=O)c3ccccc32)cc1Cl] | Cyclobutanecarboxylic acid (2-{1-[(5-chloro-2,4-dimethoxy-phenylcarbamoyl)-methyl]-2,4-dioxo-1,4-dihydro-2H-quinazolin-3-yl}-ethyl)-amide | 515 |
| 3-16 | 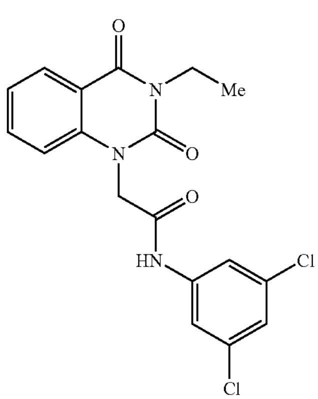 [SMILES: CCn1c(=O)c2ccccc2n(CC(=O)Nc2cc(Cl)cc(Cl)c2)c1=O] | N-(3,5-Dichloro-phenyl)-2-(3-ethyl-2,4-dioxo-3,4-dihydro-2H-quinazolin-1-yl)-acetamide | |

TABLE 3-continued

| | Structure | Chemical Name | [M + H]⁺ |
|---|---|---|---|
| 3-17 | 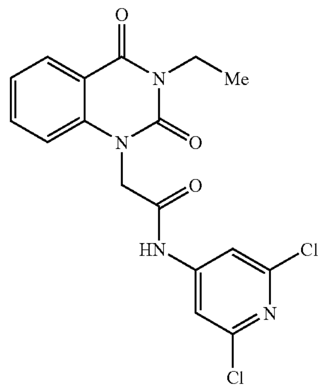 [SMILES: CCn1c(=O)c2ccccc2n(CC(=O)Nc2cc(Cl)nc(Cl)c2)c1=O] | N-(2,6-Dichloro-pyridin-4-yl)-2-(3-ethyl-2,4-dioxo-3,4-dihydro-2H-quinazolin-1-yl)-acetamide | 393 |
| 4-1 | 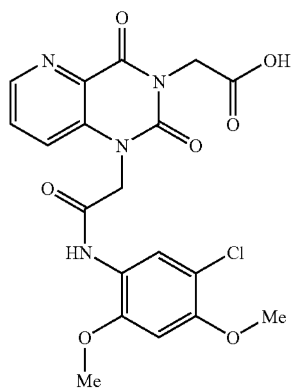 [SMILES: COc1cc(OC)c(NC(=O)Cn2c(=O)n(CC(=O)O)c(=O)c3ncccc32)cc1Cl] | {1-[(5-Chloro-2,4-dimethoxy-phenylcarbamoyl)-methyl]-2,4-dioxo-1,4-dihydro-2H-pyrido[3,2-d]pyrimidin-3-yl}-acetic acid | 449 |
| 4-2 | 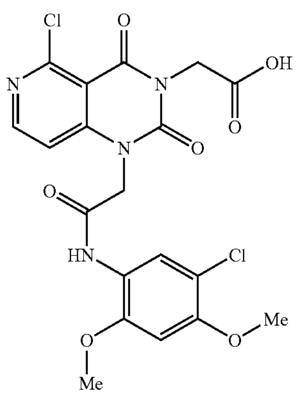 [SMILES: COc1cc(OC)c(NC(=O)Cn2c(=O)n(CC(=O)O)c(=O)c3c(Cl)nccc32)cc1Cl] | {5-Chloro-1-[(5-chloro-2,4-dimethoxy-phenylcarbamoyl)-methyl]-2,4-dioxo-1,4-dihydro-2H-pyrido[4,3-d]pyrimidin-3-yl}-acetic acid | |
| 4-3 | 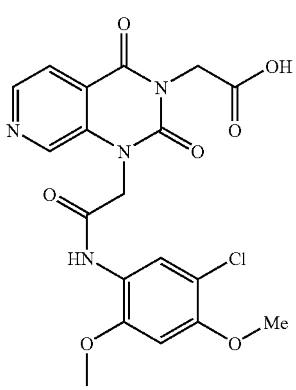 [SMILES: COc1cc(OC)c(NC(=O)Cn2c(=O)n(CC(=O)O)c(=O)c3ccncc32)cc1Cl] | {1-[(5-Chloro-2,4-dimethoxy-phenylcarbamoyl)-methyl]-2,4-dioxo-1,4-dihydro-2H-pyrido[3,4-d]pyrimidin-3-yl}-acetic acid | 449 |

Further preferred compounds of the present invention are as shown in Table 5 below.

EXAMPLES 5-1 TO 5-10

TABLE 5

| Ex. | | Name | [M + H]$^+$ |
|---|---|---|---|
| 5-1 | 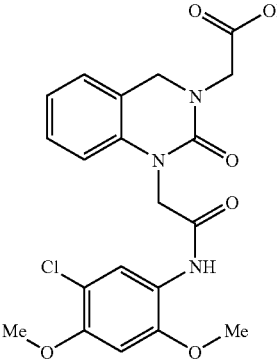 | {1-[(5-Chloro-2,4-dimethoxy-phenylcarbamoyl)-methyl]-2-oxo-1,4-dihydro-2H-quinazolin-3-yl}-acetic acid | 434 |
| 5-2 | 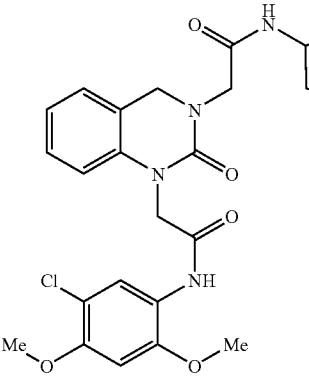 | N-(5-Chloro-2,4-dimethoxy-phenyl)-2-(3-cyclopentylcarbamoylmethyl-2-oxo-3,4-dihydro-2H-quinazolin-1-yl)-acetamide | 501 |
| 5-3 | 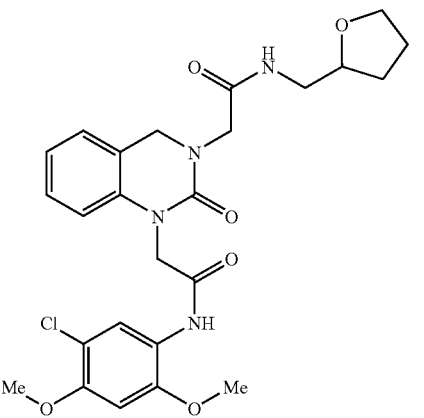 [SMILES: COc1cc(OC)c(NC(=O)CN2C(=O)N(CC(=O)NCC3CCCO3)Cc3ccccc32)cc1Cl] | N-(5-Chloro-2,4-dimethoxy-phenyl)-2-(2-oxo-3-{[(tetrahydro-furan-2-ylmethyl)-carbamoyl]-methyl}-3,4-dihydro-2H-quinazolin-1-yl)-acetamide | 517 |

TABLE 5-continued

| Ex. | Name | [M + H]⁺ |
|---|---|---|
| 5-4 | N-(5-Chloro-2,4-dimethoxy-phenyl)-2-[3-(2-morpholin-4-yl-2-oxo-ethyl)-2-oxo-3,4-dihydro-2H-quinazolin-1-yl]-acetamide | 503 |
| 5-5 | N-(5-Chloro-2,4-dimethoxy-phenyl)-2-(3-cyclopropylcarbamoylmethyl-2-oxo-3,4-dihydro-2H-quinazolin-1-yl)-acetamide | 471 |
| 5-6 | N-(5-Chloro-2,4-dimethoxy-phenyl)-2-[3-(indan-2-ylcarbamoylmethyl)-2-oxo-3,4-dihydro-2H-quinazolin-1-yl]-acetamide | 549 |
| 5-7 | N-(5-Chloro-2,4-dimethoxy-phenyl)-2-{3-[(methyl-phenethyl-carbamoyl)-methyl]-2-oxo-3,4-dihydro-2H-quinazolin-1-yl}-acetamide | 551 |

TABLE 5-continued
| Ex. | | Name | [M + H]+ |
|---|---|---|---|
| 5-8 | 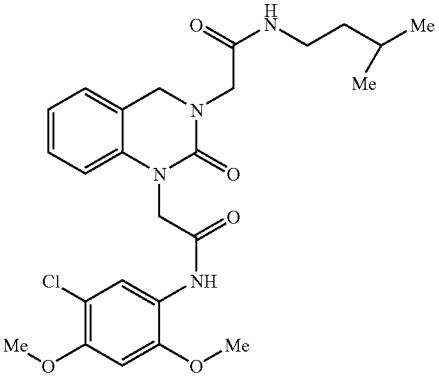 [SMILES: COc1cc(OC)c(NC(=O)CN2C(=O)N(CC(=O)NCCC(C)C)Cc3ccccc32)cc1Cl] | N-(5-Chloro-2,4-dimethoxy-phenyl)-2-{3-[(3-methyl-butylcarbamoyl)-methyl]-2-oxo-3,4-dihydro-2H-quinazolin-1-yl}-acetamide | 503 |
| 5-9 | 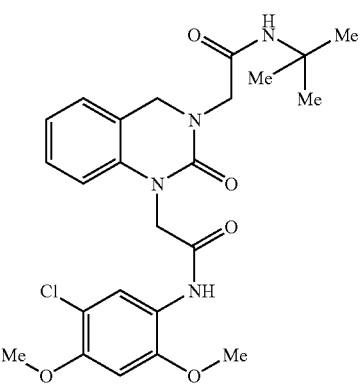 [SMILES: COc1cc(OC)c(NC(=O)CN2C(=O)N(CC(=O)NC(C)(C)C)Cc3ccccc32)cc1Cl] | 2-[3-(tert-Butylcarbamoyl-methyl)-2-oxo-3,4-dihydro-2H-quinazolin-1-yl]-N-(5-chloro-2,4-dimethoxy-phenyl)-acetamide | 489 |
| 5-10 | 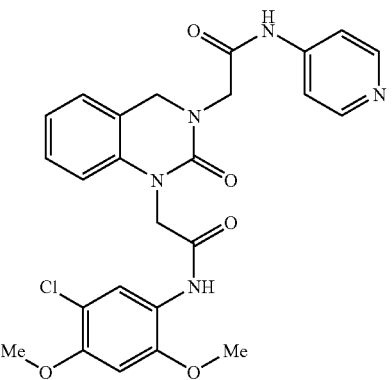 [SMILES: COc1cc(OC)c(NC(=O)CN2C(=O)N(CC(=O)Nc3ccncc3)Cc3ccccc32)cc1Cl] | N-(5-Chloro-2,4-dimethoxy-phenyl)-2-[2-oxo-3-(pyridin-4-ylcarbamoylmethyl)-3,4-dihydro-2H-quinazolin-1-yl]-acetamide | 510 |

Further compounds are as shown in Table 6 below.
COMPOUNDS 6-1 TO 6-3
TABLE 6
| Ex. | | Name |
|---|---|---|
| 6-1 | 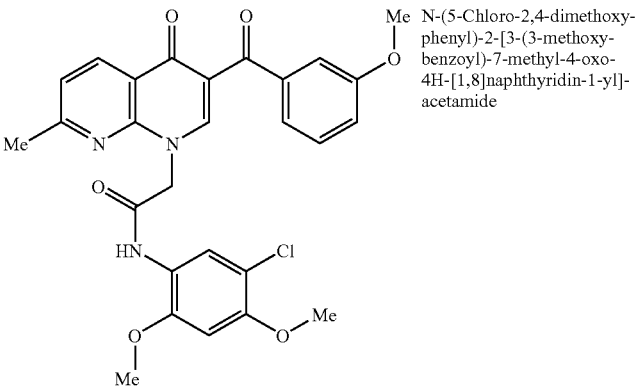 | N-(5-Chloro-2,4-dimethoxy-phenyl)-2-[3-(3-methoxy-benzoyl)-7-methyl-4-oxo-4H-[1,8]naphthyridin-1-yl]-acetamide |
| 6-2 | 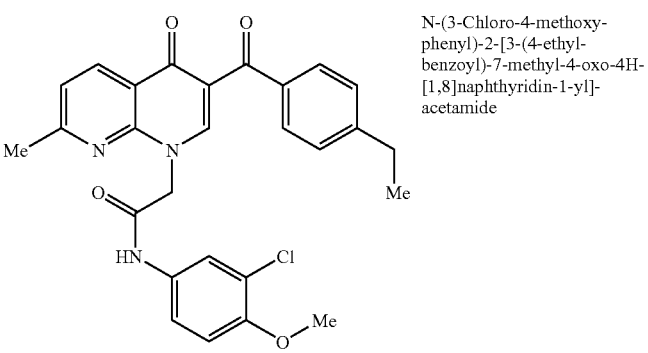 | N-(3-Chloro-4-methoxy-phenyl)-2-[3-(4-ethyl-benzoyl)-7-methyl-4-oxo-4H-[1,8]naphthyridin-1-yl]-acetamide |
| 6-3 | 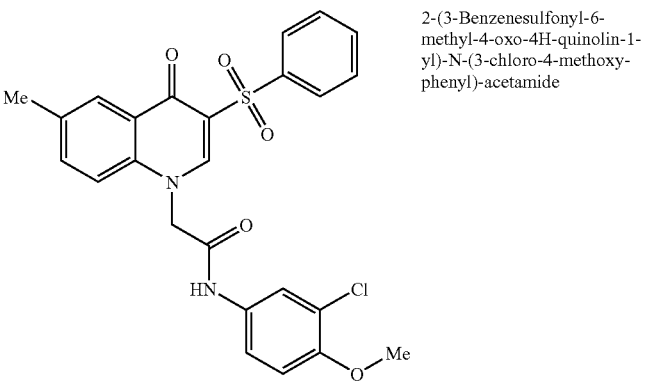 | 2-(3-Benzenesulfonyl-6-methyl-4-oxo-4H-quinolin-1-yl)-N-(3-chloro-4-methoxy-phenyl)-acetamide |

Further preferred compounds of the present invention are as shown in Table 7 below.

EXAMPLES 7-1 TO 7-6

TABLE 7

| Ex. | | Name | [M + H]$^+$ |
|---|---|---|---|
| 7-1 | 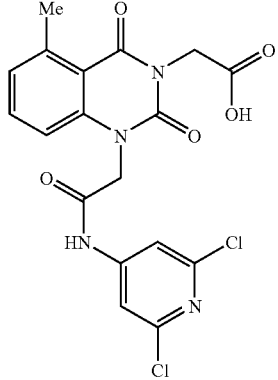 [SMILES: Cc1cccc2c1c(=O)n(CC(=O)O)c(=O)n2CC(=O)Nc1cc(Cl)nc(Cl)c1] | {1-[(2,6-Dichloro-pyridin-4-ylcarbamoyl)-methyl]-5-methyl-2,4-dioxo-1,4-dihydro-2H-quinazolin-3-yl}-acetic acid | 437.5 |
| 7-2 | 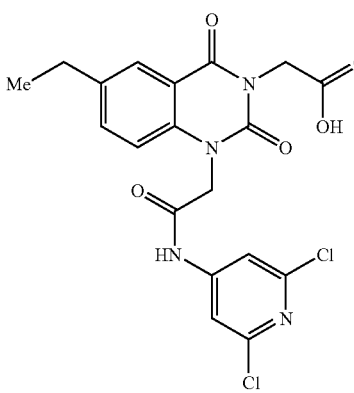 | {1-[(2,6-Dichloro-pyridin-4-ylcarbamoyl)-methyl]-6-ethyl-2,4-dioxo-1,4-dihydro-2H-quinazolin-3-yl}-acetic acid | 451.5 |
| 7-3 | 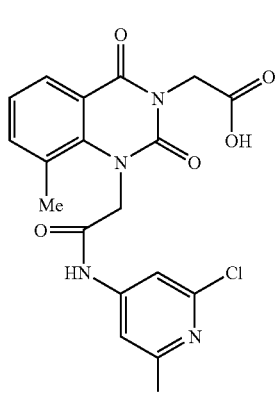 | {1-[(2,6-Dichloro-pyridin-4-ylcarbamoyl)-methyl]-8-methyl-2,4-dioxo-1,4-dihydro-2H-quinazolin-3-yl}-acetic acid | 437.0 |

TABLE 7-continued

| Ex. | | Name | [M + H]⁺ |
|---|---|---|---|
| 7-4 | 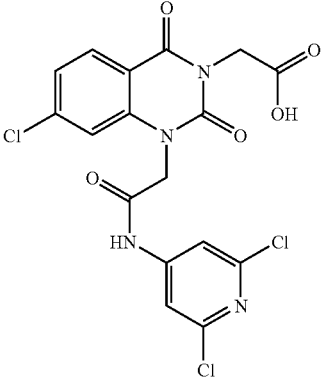 [SMILES: O=C(O)Cn1c(=O)c2ccc(Cl)cc2n(CC(=O)Nc2cc(Cl)nc(Cl)c2)c1=O] | {7-Chloro-1-[(2,6-dichloro-pyridin-4-ylcarbamoyl)-methyl]-2,4-dioxo-1,4-dihydro-2H-quinazolin-3-yl}-acetic acid | 458.9 |
| 7-5 | 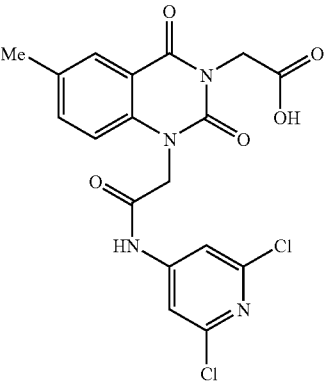 [SMILES: Cc1ccc2c(c1)c(=O)n(CC(=O)O)c(=O)n2CC(=O)Nc1cc(Cl)nc(Cl)c1] | {1-[(2,6-Dichloro-pyridin-4-ylcarbamoyl)-methyl]-6-methyl-2,4-dioxo-1,4-dihydro-2H-quinazolin-3-yl}-acetic acid | 437.0 |
| 7-6 | 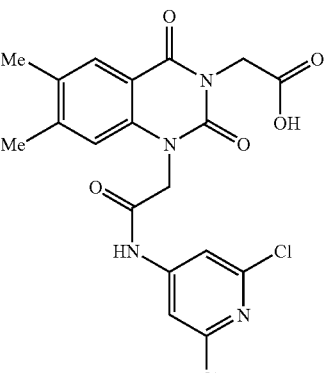 | {1-[(2,6-Dichloro-pyridin-4-ylcarbamoyl)-methyl]-6,7-dimethyl-2,4-dioxo-1,4-dihydro-2H-quinazolin-3-yl}-acetic acid | 451.4 |

Referring to the examples that follow, compounds of the embodiments are synthesized using the methods described herein, or other methods, which are known in the art.

It should be understood that the organic compounds according to certain of the embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

General Conditions:

Mass spectra are run on LCMS systems using electrospray ionization. These are either Agilent 1100 HPLC/Micromass Platform Mass Spectrometer combinations or Waters Acquity HPLC with SQD Mass Spectrometer. [M+H]+ refers to mono-isotopic molecular weights.

NMR spectra are run on open access Bruker AVANCE 400 NMR spectrometers using ICON-NMR. Spectra are measured at 298K and are referenced using the solvent peak.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

In addition various trade reagents and materials available from have been utilized. Such reagents and materials include:

[include examples such as Isolute™ (available from Biotage)] and can be readily obtained from the suppliers indicated.

For the examples below as well as throughout the application, the following abbreviations have the following meanings. If not defined, the terms have their generally accepted meanings.

| Abbreviations used are as follows: | |
|---|---|
| $Cs_2CO_3$ | cesium carbonate |
| DCM | dichloromethane |
| DIPEA | diisopropylethylamine |
| DMAP | 4-dimethylamino pyridine |
| DMF | dimethylformamide |
| DMSO | dimethyl sulfoxide |
| EtOAc | ethyl acetate |
| EtOH | ethanol |
| HATU | O-(7-Azabenzotriazol-1-yl)-N,N,N',N'-tetramethyluronium hexafluorophosphate |
| HCl | hydrochloric acid |
| $K_2CO_3$ | potassium carbonate |
| LCMS | liquid chromatographic mass spectroscopy |
| MeOH | methanol |
| $NaHCO_3$ | sodium hydrogen carbonate |
| NMP | 1-methyl-2-pyrrolidone |
| NMR | nuclear magnetic resonance |
| RT | room temperature |
| TEA | triethylamine |
| TFA | trifluoroacetic acid |
| THF | tetrahydrofuran |

PREPARATION OF EXAMPLES

Example 1-1

{1-[(5-Chloro-2,4-dimethoxy-phenylcarbamoyl)-methyl]-2,4-dioxo-1,4-dihydro-2H-quinazolin-3-yl}-acetic acid A white suspension of {1-[(5-chloro-2,4-dimethoxy-phenylcarbamoyl)-methyl]-2,4-dioxo-1,4-dihydro-2H-quinazolin-3-yl}-acetic acid methyl ester (Intermediate B) (10 mg) in MeOH (300 μL) is treated with 5 M KOH (200 μL). The white suspension is left to stir at RT overnight. The reaction mixture is diluted with water to give a thick white precipitate which is filtered-off, washed with water and vacuum dried. The aqueous phase is acidified to pH 4 with dilute HCl followed by extraction with EtOAc (3×). The organic phase is dried over $Na_2SO_4$, filtered and concentrated in vacuo to give the title compound as off-white solid. This is taken up in a minimal amount of DMF and purified further by reverse phase column chromatography (Isolute™ C18: 0-100% MeCN in water—0.1% TFA) to afford the title compound, $[M+H]^+$ 448.

Example 1-2

N-(5-Chloro-2,4-dimethoxy-phenyl)-2-(3-cyclopentylcarbamoylmethyl-2,4-dioxo-3,4-dihydro-2H-quinazolin-1-yl)-acetamide (20 mg, 44.74 mmol), cyclopentylamine (4 mg, 46.98 mmol) and HATU (18.7 mg, 49.21 mmol) are placed in a vial and treated with DMSO (1 ml). DIPEA (19.4 μL, 111.9 mmol) is added to the suspension and the reaction mixture is stirred at RT 24 hours. LCMS analysis indicated major product formation. DMSO is removed in vacuo overnight. The residue is diluted with 1 M HCl and extracted with DCM (2×15 ml). The separated organic phase is washed with aqueous saturated $NaHCO_3$, filtered and the solvent is removed in vacuo to afford the titled compound.

Examples 1-3 to 1-7, 1-9 to 1-29, 1-31, 1-32, 1-35 and 1-37

These compounds are made analogously to Example 1-2 by replacing cyclopentylamine with the appropriate commercial amines.

Example 1-8

N-(5-Chloro-2,4-dimethoxy-phenyl)-2-{3-[2-(4-methyl-piperazin-1-yl)-2-oxo-ethyl]-2,4-dioxo-3,4-dihydro-2H-quinazolin-1-yl}-acetamide To a solution of {1-[(5-Chloro-2,4-dimethoxy-phenylcarbamoyl)-methyl]-2,4-dioxo-1,4-dihydro-2H-quinazolin-3-yl}-acetic acid (0.515 g, 1.14 mmol) in NMP (8 ml), triethylamine (0.166 ml, 1.26 mmol) is added followed by HATU (0.452 g, 1.26 mmol). The mixture is stirred at RT for 5 minutes and then treated with 1-methylpiperazine (140.3 μL, 1.26 mmol). After 5 minutes at RT the reaction mixture is partitioned between EtOAc (25 ml) and water (25 ml). The phases are separated and the aqueous phase is washed further with EtOAc (2×20 ml). The organic extracts are combined, washed with saturated $NaHCO_3$ (40 ml), brine (40 ml), dried ($MgSO_4$), filtered and concentrated to give a brown oil. The residue is taken up in MeCN (5 ml) and passed through a 10 g Varian pre packed silica cartridge, eluting with MeCN then EtOAc to remove the impurities. The product is eluted off the column with MeOH. The MeOH fractions are combined and concentrated in vacuo and dried to afford the title compound, $[M+H]^+$ 530.

Example 1-30

N-(5-Chloro-2,4-dimethoxy-phenyl)-2-{3-[2-((S)-3-dimethylamino-pyrrolidin-1-yl)-2-oxo-ethyl]-2,4-dioxo-3,4-dihydro-2H-quinazolin-1-yl}-acetamide To a vial charged with {1-[(5-chloro-2,4-dimethoxy-phenylcarbamoyl)-methyl]-2,4-dioxo-1,4-dihydro-2H-quinazolin-3-yl}-acetic acid (50 mg, 0.11 mmol), HATU (46.6 mg, 0.12 mmol), and dimethyl-(S)-pyrrolidin-3-yl-amine (14.0 mg, 0.12 mmol) DCM (2 ml) is added. The mixture is treated with DIPEA (48.6 μL, 2.79 mmol) and stirred at RT for 1 hour. DCM (5 ml) is added to the mixture and washed with 1M HCl. The acidic aqueous phase is treated with 1M NaOH until the pH is adjusted to pH of 7-8. The product is extracted from the aqueous phase with EtOAc (3×10 ml). The organic portions are combined, washed with water (10 ml), dried ($MgSO_4$), filtered and concentrated to afford the title compound, $[M+H]^+$ 544

Example 1-33

[(R)-1-(2-{1-[(5-Chloro-2,4-dimethoxy-phenylcarbamoyl)-methyl]-2,4-dioxo-1,4-dihydro-2H-quinazolin-3-yl}-acetyl)-pyrrolidin-3-yl]-carbamic acid tert-butyl ester To a vial charged with {1-[(5-Chloro-2,4-dimethoxy-phenylcarbamoyl)-methyl]-2,4-dioxo-1,4-dihydro-2H-quinazolin-3-yl}-acetic acid (50.9 mg, 0.11 mmol), HATU (49.4 mg, 0.12 mmol), and (R)-Pyrrolidin-3-yl-carbamic acid tert butyl ester (25.7 mg, 0.12 mmol), DMF (3 ml) is added. The stirring mixture is treated with DIPEA (33 µL, 0.275 mmol) and stirred at RT for 1 hour. Water is added to the mixture with stirring giving rise to a solid. This is filtered off and washed with water to afford the title compound, [M+H]$^+$ 616

Example 1-34

[(S)-1-(2-{1-[(5-Chloro-2,4-dimethoxy-phenylcarbamoyl)-methyl]-2,4-dioxo-1,4-dihydro-2H-quinazolin-3-yl}-acetyl)-pyrrolidin-3-yl]-carbamic acid tert-butyl ester To a vial charged with {1-[(5-chloro-2,4-dimethoxy-phenylcarbamoyl)-methyl]-2,4-dioxo-1,4-dihydro-2H-quinazolin-3-yl}-acetic acid (50.1 mg, 0.11 mmol), HATU (50.1 mg, 0.12 mmol), and (R)-pyrrolidin-3-yl-carbamic acid tert butyl ester (22.8 mg, 0.12 mmol), DMF (3 ml) was added. The stirring mixture is treated with DIPEA (33 µL, 0.275 mmol) and stirred at RT. Water is added to the mixture with stirring giving rise to a solid. This is filtered off and washed with water to afford the title compound; [M+H]$^+$ 616

Example 1-37

{1-[(5-Chloro-2,4-dimethoxy-phenylcarbamoyl)-methyl]-2,4-dioxo-1,4-dihydro-2H-quinazolin-3-yl}-acetic acid tert butyl ester Example 1-37 is made analogously to Example 3-10 by replacing 2-Bromo-N-(2,6-dichloro-pyridine-4-yl)-acetamide (Intermediate N) with 2-Bromo-N-(5-chloro-2,4-dimethoxy-phenyl)-acetamide (Intermediate C).

Example 2-1

N-(5-Chloro-2,4-dimethoxy-phenyl)-2-{2,4-dioxo-3-[4-(phenethylcarbamoyl-methyl)-phenyl]-3,4-dihydro-2H-quinazolin-1-yl}-acetamide This compound is made analogously to Example 1-2 by replacing {1-[(5-chloro-2,4-dimethoxy-phenylcarbamoyl)-methyl]-2,4-dioxo-1,4-dihydro-2H-quinazolin-3-yl}-acetic acid (Intermediate A) with ({2,4-dioxo-3-[4-(phenethylcarbamoyl-methyl)-phenyl]-3,4-dihydro-2H-quinazolin-1-yl}-acetic acid) (Intermediate D) and by replacing cyclopentylamine with 5-chloro-2,4-dimethoxy-phenylamine to afford the title compound. The reaction is carried out using DMF as the solvent.

Examples 2-2 to 2-3

These compounds are made analogously to Example 2-1 by replacing 5-chloro-2,4-dimethoxy-phenylamine with the appropriate commercial amines.

Example 2-4

(4-{1-[(5-Chloro-2,4-dimethoxy-phenylcarbamoyl)-methyl]-2,4-dioxo-1,4-dihydro-2H-quinazolin-3-yl}-phenyl)-acetic acid (4-[1-[(5-Chloro-2,4-dimethoxy-phenylcarbamoyl)-methyl]-2,4-dioxo-1,4-dihydro-2H-quinazolin-3-yl}-phenyl)-acetic acid ethyl ester (Intermediate K) (105.4 mg, 0.19 mmol) is added to a stirred solution of Bis(tributyltin)oxide (2 eq, 0.38 mmol, 193.1 µL) in toluene (10 ml). The mixture is heated at reflux at 120° C. for 72 hours. The toluene is removed in vacuo, and the red/brown oily residue is partitioned between EtOAc and saturated NaHCO$_3$ (5 ml). The resultant precipitate is filtered, washed with NaHCO$_3$, EtOAc, 1M HCl, water, and dried to give the title compound, [M+H]$^+$ 524

Example 3-1

(2-{1-[(5-Chloro-2,4-dimethoxy-phenylcarbamoyl)-methyl]-2,4-dioxo-1,4-dihydro-2H-quinazolin-3-yl}-ethyl)-carbamic acid tert-butyl ester This compound is made analogously to Example 1-2 by replacing Intermediate A with [3-(2-tert-butoxycarbonylamino-ethyl)-2,4-dioxo-3,4-dihydro-2H-quinazolin-1-yl]-acetic acid and by replacing cyclopentylamine with 5-chloro-2,4-dimethoxyaniline to afford the title compound. The reaction is carried out in DCM.

Compounds 3-2 to 3-9

These compounds and their methods of manufacture are known.

Example 3-10

{1-[(2,6-Dichloro-pyridin-4-ylcarbamoyl)-methyl]-2,4-dioxo-1,4-dihydro-2H-quinazolin-3-yl}-acetic acid tert-butyl ester A mixture comprising (2,4-dioxo-1,4-dihydro-2H-quinazolin-3-yl)-acetic acid tert-butyl ester (Intermediate L) (226.7 mg, 0.82 mmol), 2-bromo-N-(2,6-dichloro-pyridine-4-yl)-acetamide (Intermediate N) (256.5 mg, 0.902 mmol) and Cs$_2$CO$_3$ (545.1 mg, 1.64 mmol) in DMF (5 ml) is stirred at RT for 3 hours. The resulting mixture is treated with water and the precipitate is filtered under vacuum. The solid is washed with water, iso-hexane and then dried to give the title compound, [M+H]$^+$ 479

Example 3-11

{1-[(2,6-Dichloro-pyridin-4-ylcarbamoyl)-methyl]-2,4-dioxo-1,4-dihydro-2H-quinazolin-3-yl}-acetic acid A round bottomed flask is charged with {1-[(2,6-Dichloro-pyridin-4-ylcarbamoyl)-methyl]-2,4-dioxo-1,4-dihydro-2H-quinazolin-3-yl}-acetic acid tert-butyl ester (50.9 mg, 0.106 mmol) is treated with DCM (1.5 ml) and TFA (1.5 ml). The reaction mixture is stirred at RT for 2 hours and then concentrated in vacuo. The residue is taken up in a minimal amount of DCM and concentrated in vacuo. This process is repeated twice with EtOAc, and twice with MeOH to give the title compound, [M+H]$^+$ 422

Example 3-12

N-(2,6-Dichloro-pyridin-4-yl)-2-{3-[2-(4-methyl-piperazin-1-yl)-2-oxo-ethyl]-2,4-dioxo-3,4-dihydro-2H-quinazolin-1-yl}-acetamide To a solution of {1-[(2,6-dichloro-pyridin-4-ylcarbamoyl)-methyl]-2,4-dioxo-1,4-dihydro-2H-quinazolin-3-yl}-acetic acid (13.5 mg, 0.0318 mmol) in dry NMP (1.5 ml), HATU (13.3 mg, 0.035 mmol) is added followed by triethylamine (4.89 μL, 0.035 mmol). The orange solution is stirred at RT for 10 minutes, then treated with 1-methyl piperazine (3.89 μL, 0.035 mmol). The reaction mixture is stirred at RT and monitored by HPLC/LCMS until the starting material is consumed. The reaction mixture is partitioned between EtOAc (5 ml) and water (5 ml). The organic layer is separated and washed with brine (5 ml), dried (MgSO$_4$), filtered and concentrated in vacuo. The crude product is purified by passing down a 5 g Isolute™ SCX2 (solid-supported sulfonic acid resin) cartridge, eluting with DCM (20 ml), MeOH (20 ml), and 7N NH$_3$ in MeOH. The basic ammonia wash is concentrated in vacuo to afford the title compound as a white solid, [M+H]$^+$ 505.

Example 3-13

2-[3-(2-Amino-ethyl)-2,4-dioxo-3,4-dihydro-2H-quinazolin-1-yl]-N-(5-chloro-2,4-dimethoxy-phenyl)-acetamide trifluoroacetate (2-{1-[(5-Chloro-2,4-dimethoxy-phenylcarbamoyl)-methyl]-2,4-dioxo-1,4-dihydro-2H-quinazolin-3-yl}-ethyl)-carbamic acid tert-butyl ester (100 mg, 1.88 mmol) is taken up in DCM (2 ml) and treated with TFA (2 ml). The reaction is stirred at RT for 2 hours and then treated with EtOAc (20 ml). After 5 minutes, the white solid present is filtered, washed with EtOAc, ether and dried under vacuum to give the title compound as a white solid; [M+H]$^+$ 433, Example 3-14

N-(2-{1-[(5-Chloro-2,4-dimethoxy-phenylcarbamoyl)-methyl]-2,4-dioxo-1,4-dihydro-2H-quinazolin-3-yl}-ethyl)-3-methyl-butyramide To a suspension of 2-[3-(2-amino-ethyl)-2,4-dioxo-3,4-dihydro-2H-quinazolin-1-yl]-N-(5-chloro-2,4-dimethoxy-phenyl)-acetamide trifluoroacetate (75 mg, 0.17 mmol) in THF (1 ml), triethylamine is added (0.06 ml, 0.43 mmol) followed by isovaleryl chloride (30 mg, 0.26 mmol). The mixture is stirred overnight at RT and then treated with water (3 ml). The resulting solid is filtered and washed with water to afford the title compound; [M+H]$^+$ 517.3.

Example 3-15

Cyclobutanecarboxylic acid (2-{1-[(5-chloro-2,4-dimethoxy-phenylcarbamoyl)-methyl]-2,4-dioxo-1,4-dihydro-2H-quinazolin-3-yl}-ethyl)-amide To a suspension of 2-[3-(2-Amino-ethyl)-2,4-dioxo-3,4-dihydro-2H-quinazolin-1-yl]-N-(5-chloro-2,4-dimethoxy-phenyl)-acetamide trifluoroacetate (75 mg, 0.17 mmol) in THF (1 ml), triethylamine is added (0.06 ml, 0.43 mmol) followed cyclobutane carbonyl chloride (30 mg, 0.26 mmol). The mixture is stirred overnight at RT. Water (3 ml) and then EtOAc is added to the mixture to give a suspension which is filtered to remove the solid. The filtrate is washed with water, dried and evaporated to afford the title compound, [M+H]$^+$ 515

Example 3-16

N-(3,5-Dichloro-phenyl)-2-(3-ethyl-2,4-dioxo-3,4-dihydro-2H-quinazolin-1-yl)-acetamide To a round bottomed flask charged with (3-ethyl-2,4-dioxo-3,4-dihydro-2H-quinazolin-1-yl)-acetic) acid (72 mg, 0.26 mmol) and diisopropylethylamine (Hunig's Base; 0.11 ml, 0.63 mmol) in DCM (1.5 ml), 3,5-dichlorophenylamine (47 mg, 0.29 mmol) and HATU (109 mg, 0.29 mmol) are added. The reaction mixture is stirred overnight and then treated with water (3 ml) and ether (2 ml). The resulting solid is filtered and washed with water (3×), ether and then dried. Trituration with MeOH affords the title compound.

Example 3-17

N-(2,6-Dichloro-pyridin-4-yl)-2-(3-ethyl-2,4-dioxo-3,4-dihydro-2H-quinazolin-1-yl)-acetamide To a round bottomed flask charged with (3-Ethyl-2,4-dioxo-3,4-dihydro-2H-quinazolin-1-yl)-acetic) acid (72 mg, 0.26 mmol) and diisopropylethylamine (Hunig's Base; 0.11 ml, 0.63 mmol) in DCM (1.5 ml), 2,6-dichloro-pyridin-4-ylamine (47 mg, 0.29 mmol) and HATU (109 mg, 0.29 mmol) are added. The reaction mixture is stirred overnight and then water (3 ml) and ether (2 ml) are added. The resulting mixture was purified by preparative HPLC to give the title compound; [M+H]$^+$ 393

Example 4-1

{1-[(5-Chloro-2,4-dimethoxy-phenylcarbamoyl)-methyl]-2,4-dioxo-1,4-dihydro-2H-pyrido[3,2-d]pyrimidin-3-yl}-acetic acid A stirring solution of {1-[(5-chloro-2,4-dimethoxy-phenylcarbamoyl)-methyl]-2,4-dioxo-1,4-dihydro-2H-pyrido[3,2-d]pyrimidin-3-yl}-acetic acid tert-butyl ester (Intermediate R) (22.1 mg, 0.044 mmol) in DCM (1 ml) is treated with TFA (1 ml). The reaction mixture is stirred at RT and monitored by HPLC/LCMS until the starting material is consumed. After 3 hours, the reaction mixture is diluted with a minimal amount of DCM and concentrated in vacuo. The residue is taken up in a minimal amount of MeOH, concentrated in vacuo, the again in a minimal amount of EtOAc and concentrated in vacuo to afford the title compound as an off white solid; [M+H]$^+$ 449

Example 4-2

{5-Chloro-1-[(5-chloro-2,4-dimethoxy-phenylcarbamoyl)-methyl]-2,4-dioxo-1,4-dihydro-2H-pyrido[4,3-d]pyrimidin-3-yl}-acetic acid To a vial containing a solution of {5-Chloro-1-[(5-chloro-2,4-dimethoxy-phenylcarbamoyl)-methyl]-2,4-dioxo-1,4-dihydro-2H-pyrido[4,3-d]pyrimidin-3-yl}-acetic acid tert-butyl ester (Intermediate T) (10.1 mg, 0.019 mmol) in DCM (1 ml), TFA (1 ml) is added. The reaction mixture is stirred at RT for 2 hours, transferred to a 10 ml round bottomed flask, diluted with a minimal amount of DCM and concentrated in vacuo. The residue is taken up in a minimal amount of DCM and concentrated in vacuo. This process is repeated once with DCM, twice with EtOAc, and once with MeOH, the solvent being concentrated in vacuo each time, finally giving the title compound.

Example 4-3

{1-[(5-Chloro-2,4-dimethoxy-phenylcarbamoyl)-methyl]-2,4-dioxo-1,4-dihydro-2H-pyrido[3,4-d]pyrimidin-3-yl}-acetic acid To a vial containing a solution of {1-[(5-Chloro-2,4-dimethoxy-phenylcarbamoyl)-methyl]-2,4-dioxo-1,4-dihydro-2H-pyrido[3,4-d]pyrimidin-3-yl}-acetic acid tert-butyl ester (Intermediate V) (15 mg, 0.029 mmol) in DCM (1 ml), TFA (1 ml) is added. The mixture is stirred at RT overnight. The reaction mixture is then transferred to a 10 ml round bottomed flask, diluted with a minimal amount of DCM and concentrated in vacuo. This process is repeated once with DCM, twice with EtOAc, and once with MeOH, the solvent being concentrated in vacuo each time, finally giving the title, [M+H]$^+$ 448.93.

Example 5-1

{1-[(5-Chloro-2,4-dimethoxy-phenylcarbamoyl)-methyl]-2-oxo-1,4-dihydro-2H-quinazolin-3-yl}-acetic acid An off-white suspension of {1-[(5-chloro-2,4-dimethoxy-phenylcarbamoyl)-methyl]-2-oxo-1,4-dihydro-2H-quinazolin-3-yl}-acetic acid methyl ester (Intermediate I) (400 mg, 0.893 mmol) in MeOH (10 ml) is treated with 5 M KOH (5 ml). The resulting white suspension is left to stir at RT overnight to give clear solution. The aqueous reaction mixture is acidified with dilute HCl (1 M) to pH 4 to give a thick white precipitate which is filtered, washed with water and vacuum dried to afford the title compound as pale yellow solid; [M+H]$^+$ 434.

Example 5.2

N-(5-Chloro-2,4-dimethoxy-phenyl)-2-(3-cyclopentylcarbamoylmethyl-2-oxo-3,4-dihydro-2H-quinazolin-1-yl)-acetamide A solution of {1-[(5-chloro-2,4-dimethoxy-phenylcarbamoyl)-methyl]-2-oxo-1,4-dihydro-2H-quinazolin-3-yl}-acetic acid (Example 5-1) (20 mg, 0.046 mmol) in DMSO (1 ml) is treated with a solution of HATU (19.3 mg, 0.05 mmol) in DMSO (2 ml). The reaction mixture is then treated with cyclopentylamine (4.12 mg, 0.048 mmol) and the reaction left to stand at RT overnight. The reactions are analysed by HPLC/LCMS and concentrated in vacuo. The residue is taken up in DCM and washed with 1M HCl The organic phase is washed with saturated NaHCO$_3$ and concentrated in vacuo to give the title compound; [M+H]$^+$ 501

Examples 5-3 to 5-10

These compounds are made analogously to Example 5-2 by replacing cyclopentylamine with the appropriate commercial amines.

Compounds 6-1 to 6-3

These compounds and their method of manufacture are known.

Example 7-1

{1-[(2,6-Dichloro-pyridin-4-ylcarbamoyl)-methyl]-5-methyl-2,4-dioxo-1,4-dihydro-2H-quinazolin-3-yl}-acetic acid Step 1: (2-Amino-6-methyl-benzoylamino)-acetoyl polystyrene To a portion of FMoc glycine on Wang resin (500 mg, 0.45 mmol, loading=0.85 mmol/g) is added piperidine (5 ml of a 20% solution in DMF). The resulting slurry is shaken at RT for 1 hour then filtered and washed with DMF (3×1 ml). The resulting resin is treated with piperidine (20% in DMF, 5 ml) and shaken at RT. After 1 hour the resin is filtered, washed with DMF (3×1 ml) and concentrated in vacuo. The resin was then treated with 5-methyl-1H-benzo[d][1,3]oxazine-2,4-dione (prepared according to the method described in WO2006074187) (250 mg) in DMF (5 ml) and shaken at RT for 12 days. The resin is then filtered, washed with MeOH (3×5 ml), CH$_2$Cl$_2$ (5 ml) and THF (3×5 ml) and then dried in vacuo to afford the title compound.

Step 2: (5-Methyl-2,4-dioxo-1,4-dihydro-2H-quinazolin-3-yl)-acetoyl polystyrene

To (2-amino-6-methyl-benzoylamino)-acetoyl polystyrene (crude product from step 1) is added a solution of triphosgene (60 mg, 0.2 mmol) in THF (5 ml). The resin is shaken at RT for 2 days and then filtered under vacuum. The resin is then washed with THF (3×5 ml), CH$_2$Cl$_2$ (2×5 ml) and THF (5 ml) and concentrated in vacuo to afford the title compound.

Step 3: {1-[(2,6-Dichloro-pyridin-4-ylcarbamoyl)-methyl]-5-methyl-2,4-dioxo-1,4-dihydro-2H-quinazolin-3-yl}-acetic acid To (5-methyl-2,4-dioxo-1,4-dihydro-2H-quinazolin-3-yl)-acetoyl polystyrene (crude product from step 2) is added a solution of 2-bromo-N-(2,6-dichloro-pyridine-4-yl)-acetamide (Intermediate N) (0.45 M) in N-methylpyrrolidone (4 ml) followed by tetramethylguanidine (0.2 ml). The resin is shaken at RT for 6 days and then filtered and washed with CH$_2$Cl$_2$ (6×2 ml). Cleavage of the resin by treatment of with TFA (1.25 ml) in CH$_2$Cl$_2$ (1.25 ml) followed by purification using preparative HPLC (eluting with MeCN, H$_2$O and TFA) affords the title compound. [M+H]$^+$ 438.

Examples 7-2-7-6

These compounds named in Table 7 are prepared analogously to Example 7-1 by replacing 5-methyl-1H-benzo[d][1,3]oxazine-2,4-dione with the appropriate isatoic anhydride derivatives. The isatoic anhydride derivatives are either commercially available or are prepared using literature methods.

Preparation of Intermediates

Intermediate A {1-[(5-Chloro-2,4-dimethoxy-phenylcarbamoyl)-methyl]-2,4-dioxo-1,4-dihydro-2H-quinazolin-3-yl}-acetic acid The preparation of this compound is described as Example 1-1; [M+H]$^+$ 448.

Intermediate B {1-[(5-Chloro-2,4-dimethoxy-phenylcarbamoyl)-methyl]-2,4-dioxo-1,4-dihydro-2H-quinazolin-3-yl}-acetic acid methyl ester A mixture of (2,4-dioxo-1,4-dihydro-2H-quinazolin-3-yl)-acetic acid methyl ester (1 g, 4.27 mmol), K$_2$CO$_3$ (910 mg, 6.404 mmol) and 2-bromo-N-(5-chloro-2,4-dimethoxy-phenyl)-acetamide (Intermediate C) (1.42 g, 4.697 mmol) in dry DMF (6 ml) is left to stir at RT overnight. The reaction mixture is diluted with water resulting in a cream precipitate which is filtered, washed with water and dried under vacuum to give the title compound as a pale yellow solid [M+H]$^+$ 462.

Intermediate C 2-Bromo-N-(5-chloro-2,4-dimethoxy-phenyl)-acetamide

A cooled (0° C.) solution of 5-chloro-2,4-dimethoxyaniline (5 g) in DCM under an atmosphere of argon is treated dropwise with bromoacetyl bromide (2.4 ml). After 5 minutes, TEA (7.5 ml) is added dropwise and after stirring for 20 minutes the reaction mixture is diluted with water and extracted with DCM). The organic phase is washed with distilled water, dried over Na$_2$SO$_4$, filtered and evaporated to give a beige solid. This is purified by flash column chromatography on silica, eluting with 20-100% n-hexane in DCM to afford the title compound. [M+H]$^+$ 308.

Intermediate D {2,4-Dioxo-3-[4-(phenethylcarbamoyl-methyl)-phenyl]-3,4-dihydro-2H-quinazolin-1-yl}-acetic acid A stirred solution of {2,4-dioxo-3-[4-(phenethylcarbamoyl-methyl)-phenyl]-3,4-dihydro-2H-quinazolin-1-yl}-acetic acid tert-butyl ester (Intermediate E) (470 mg, 0.916 mmol) and triethylsilane (0.37 ml, 2.9 mmol) in dry DCM (2.5 ml) under argon is treated dropwise with TFA (2.5 ml). After 18 hours, the reaction mixture is evaporated in vacuo and the residue is triturated with MeOH resulting in a white solid. The solid is filtered and dried under vacuum to afford the title compound.
$^1$H NMR (CDCl$_3$, 400 MHz); 8.2 (t, 1H), 8.1 (d, 1H), 7.45 (d, 1H), 7.2 (d, 3H), 4.9 (s, 2H), 3.5 (s, 2H), 3.32 (q, 2H), 2.75 (t, 2H). [M+H]$^+$ 458.

Intermediate E {2,4-Dioxo-3-[4-(phenethylcarbamoyl-methyl)-phenyl]-3,4-dihydro-2H-quinazolin-1-yl}-acetic acid tert-butyl ester A stirred suspension of [4-(1-tert-butoxycarbonylmethyl-2,4-dioxo-1,4-dihydro-2H-quinazolin-3-yl)-phenyl]-acetic acid (Intermediate F) (932 mg, 2.27 mmol), 2-(aminoethyl)benzene (1.2 eq, 344 mg, 2.72 mmol) and HATU (1.2 eq, 1.035 g. 2.72 mmol) in DCM (8 ml) is treated with DIPEA (2 eq, 711 µL, 4.54 mmol). The reaction mixture is stirred at RT for 48 hours. The mixture is diluted with distilled water (5 ml) followed by 0.1 M HCl (5 ml) and extracted with EtOAc (2×15 ml). The combined organic portions are washed with aqueous saturated aqueous NaHCO$_3$, dried (MgSO$_4$) and concentrated in vacuo.
Purification by flash column chromatography (Varian Mega Bond silica 70 g n-hexane/EtOAc 10-80%) affords the title compound as a white crystalline solid.
$^1$H NMR (CDCl$_3$, 400 MHz); 8.3 (d, 1H), 7.25 (t, 1H), 7.35 (d, 4H), 7.3 (d, 3H), 7.25 (t, 1H), 7.15 (d, 2H), 7.05 (d, 1H), 4.35 (s, 2H), 3.65 (s, 2H), 3.55 (q, 2H), 2.8 (t, 3H), 1.5 (s, 9H). [M+H]$^+$ 514.

Intermediate F [4-(1-tert-Butoxycarbonylmethyl-2,4-dioxo-1,4-dihydro-2H-quinazolin-3-yl)-phenyl]-acetic acid A solution of [4-(1-tert-butoxycarbonylmethyl-2,4-dioxo-1,4-dihydro-2H-quinazolin-3-yl)-phenyl]-acetic acid ethyl ester (Intermediate G) (1.4 g, 3.2 mmol) in MeOH (25 ml) is treated with aqueous sodium hydroxide (0.5 M, 10 ml). After stirring at RT for 30 minutes, the MeOH is removed in vacuo and the resulting mixture is diluted with distilled water and washed with EtOAc (2×) to remove impurities. The separated aqueous phase is acidified with dilute HCl (0.1 M) to pH 3 and extracted with EtOAc (2×). The combined organic portions are dried over MgSO$_4$, filtered and concentrated in vacuo to afford the title compound as an off-white solid.
$^1$H NMR (CDCl$_3$, 400 MHz); 8.1 (d, 1H), 7.8 (t, 1H), 7.4 (d of d, 4H), 7.25 (d, 2H), 4.88 (s, 2H), 3.68 (s, 2H), 1.45 (s, 9H). [M+H]$^+$ 411.

Intermediate G [4-(1-tert-Butoxycarbonylmethyl-2,4-dioxo-1,4-dihydro-2H-quinazolin-3-yl)-phenyl]-acetic acid ethyl ester A mixture of [4-(2,4-dioxo-1,4-dihydro-2H-quinazolin-3-yl)-phenyl]-acetic acid ethyl ester (Intermediate H) (9.5 g, 29.3 mmol) and K$_2$CO$_3$ (2.5 eq, 10.31 g, 73.3 mmol) in a round bottom flask is treated with dry DMF. tert-Butyl bromoacetate (1.02 eq, 4.2 ml, 30 mmol) is added dropwise via syringe under argon. The reaction suspension is stirred at RT for 1 hour. The reaction mixture is diluted with distilled water and extracted with EtOAc (3×). The separated organic layer is dried over MgSO$_4$, filtered and the solvent is concentrated in vacuo. The title compound is obtained as a brown viscous oil, crystallizing on standing.
$^1$H NMR (CDCl$_3$, 400 MHz); 8.2 (d, 1H), 7.62 (t, 1H), 7.4 (d, 2H), 7.25 (t, 1H), 7.2 (s, 2H), 6.95 (d, 1H), 4.75 (s, 2H), 4.1 (q, 2H), 3.6 (s, 2H), 1.4 (s, 9H), 1.2 (t, 3H). [M+H]$^+$ 439.

Intermediate H [4-(2,4-Dioxo-1,4-dihydro-2H-quinazolin-3-yl)-phenyl]-acetic acid ethyl ester Step 1: [4-(2-Amino-benzoylamino)-phenyl]-acetic acid ethyl ester A round bottomed flask is charged with isatoic anhydride (5 g, 30.6 mmol) and (4-amino-phenyl)-acetic acid ethyl ester (6.05 g, 33.7 mmol). Acetic acid (11 ml) is added and the reaction is heated at 90° C. for 40 minutes and then allowed to cool to RT. The resulting suspension is diluted with distilled water to give a white precipitate. The precipitate is filtered, washed with water and vacuum dried to afford the title compound.
$^1$H NMR (CDCl$_3$, 400 MHz); 7.75 (s, 1H), 7.55 (d, 2H), 7.5 (d, 1H), 7.35 (d, 2H), 6.75 (d of d, 2H), 5.56 (s broad, NH2), 3.85 (q, 3H), 3.62 (s, 2H) [M+H]$^+$ 299.

Step 2: [4-(2,4-Dioxo-1,4-dihydro-2H-quinazolin-3-yl)-phenyl]-acetic acid ethyl ester A mixture of [4-(2-amino-benzoylamino)-phenyl]-acetic acid ethyl ester (14.2 g, 47 mmol) and triphosgene (0.5 eq, 7.03 g, 23.5 mmol) in DCM (200 ml) is treated with DIPEA (2 eq, 16.5 ml, 94 mmol) dropwise via dropping funnel while stirring at RT. After 1 hour, the reaction mixture is diluted with DCM and washed with saturated aqueous NaHCO$_3$. The separated organic layer is washed with distilled water (2×), dried over MgSO$_4$, filtered and the solvent removed in vacuo. The title compound is obtained as pure white solid.
$^1$H NMR (CDCl$_3$, 400 MHz); 8.3 (s, 1H), 8.1 (d, 1H), 7.55 (t, 1H), 7.4 (d, 2H), 7.2 (d, 1H), 6.98 (d, 2H), 4.1 (q, 3H), 3.6 (s, 2H), 1.22 (t, 2H). [M+H]$^+$ 325.

Intermediate I {1-[(5-Chloro-2,4-dimethoxy-phenylcarbamoyl)-methyl]-2-oxo-1,4-dihydro-2H-quinazolin-3-yl}-acetic acid methyl ester A mixture of (3-methoxycarbonylmethyl-2-oxo-3,4-dihydro-2H-quinazolin-1-yl)-acetic acid (Intermediate J) (395 mg, 1.078 mmol), HATU (594 mg, 1.186 mmol) and 5-chloro-2,4-dimethoxy-phenylamine (293 mg, 1.186 mmol) in DCM (5 ml) is treated with DIPEA (2.5 eq, 618 μL). The reaction solution is stirred at RT and after 24 hours the reaction mixture is diluted with 1 M HCl (5 ml) and extracted with DCM (2×15 ml). The combined separated organic layers are washed with aqueous saturated NaHCO$_3$. The organic phase is dried over MgSO$_4$, filtered and is concentrated in vacuo to afford the title compound as off-white solid; [M+H]$^+$ 448.

Intermediate J (3-Methoxycarbonylmethyl-2-oxo-3, 4-dihydro-2H-quinazolin-1-yl)-acetic acid Step 1: (2-Amino-benzylamino)-acetic acid methyl ester 2-Aminomethyl-phenylamine (1.54 g, 10.1 mmol) and TEA (3.06 ml, 20.2 mmol) are refluxed in 1,4-dioxane. A solution of ethyl bromoacetate (1.12 ml, 10.1 mmol) in 1,4-dioxane (5 ml) is added slowly over 1 hour resulting in a precipitate. The reaction mixture is stirred at reflux for 2 hours. The reaction mixture is cooled to RT, treated with water and extracted with EtOAc, the organic phase is dried over MgSO$_4$, filtered and is concentrated in vacuo. Purification by flash column chromatography on silica, eluting with DCM:MeOH (40:1) affords the title compound; [M+H]$^+$ 195.

Step 2: (2-Oxo-1,4-dihydro-2H-quinazolin-3-yl)-acetic acid methyl ester (2-Amino-benzylamino)-acetic acid methyl ester (0.50 g, 2 mmol) and bis(trichloromethyl)carbonate (0.54 g, 2 mmol) are dissolved in dioxane (5 ml) and stirred at RT for 24 hours. The reaction mixture is treated with water and extracted with EtOAc, the organic phase is dried over MgSO$_4$, filtered and is concentrated in vacuo. Purification by flash column chromatography on silica, eluting with DCM:MeOH (10:1) affords the title compound. [M+H]$^+$ 221.

Step 3: 1-tert-butoxycarbonylmethyl-2-oxo-1,4-dihydro-2H-quinazolin-3-yl)-acetic acid methyl ester A mixture of (2-oxo-1,4-dihydro-2H-quinazolin-3-yl)-acetic acid methyl ester (9.5 g, 29.3 mmol) and K$_2$CO$_3$ (2.5 eq, 10.31 g, 73.3 mmol) in a round bottom flask are treated with dry DMF. Tert-Butyl bromoacetate (1.02 eq, 4.2 ml, 30 mmol) is added dropwise via syringe under argon. The reaction suspension is stirred at RT for one hour. The reaction mixture is diluted with distilled water and extracted with EtOAc (3×). The separated organic layer is dried over MgSO$_4$, filtered and the solvent concentrated in vacuo. The title compound is obtained as brown viscous oil crystallizing on standing. [M+H]$^+$ 335.

Step 4: (3-Methoxycarbonylmethyl-2-oxo-3,4-dihydro-2H-quinazolin-1-yl)-acetic acid A solution of 1-tert-butoxycarbonylmethyl-2-oxo-1,4-dihydro-2H-quinazolin-3-yl)-acetic acid methyl ester (470 mg, 0.916 mmol) in dry DCM is treated dropwise under argon with TFA followed by addition of triethylsilane. After 5 hours, the reaction mixture is concentrated in vacuo and the residue is triturated with MeOH to give a white solid. The title compound is obtained by filtration, followed by vacuum drying as a white solid. [M+H]$^+$ 279.

Intermediate K [4-{1-[(5-Chloro-2,4-dimethoxy-phenylcarbamoyl)-methyl]-2,4-dioxo-1,4-dihydro-2H-quinazolin-3-yl}-phenyl)-acetic acid ethyl ester A round bottomed flask charged with [4-(2,4-dioxo-1,4-dihydro-2H-quinazolin-3-yl)-phenyl]-acetic acid ethyl ester (Intermediate H) (2.0 g, 6.17 mmol), K$_2$CO$_3$ (2.5 eq, 2.14 g, 15.52 mmol), and 2-bromo-N-(5-chloro-2,4-dimethoxy-phenyl)-acetamide (Intermediate C) (1.02 eq, 1.99 g, 6.49 mmol) is treated with dry DMF (20 ml). The reaction is stirred at RT for 72 hours. The reaction mixture is diluted with distilled water and stirred for 15 minutes. The precipitate formed was filtered, washed with water and dried under vacuum to give the title compound; [M+H]$^+$ 552

Intermediate L (2,4-Dioxo-1,4-dihydro-2H-quinazolin-3-yl)-acetic acid tert butyl ester To a cooled (<5° C.) solution of (2-amino-benzoylamino)-acetic acid tert-butyl ester (33 g, 0.132 mol) in DCM (200 ml), a solution of triphosgene (14.08 g, 0.047 mol) in DCM (70 ml) is added dropwise over 30 minutes, keeping the temperature below 5° C. The resulting white/cream precipitate is treated dropwise with triethylamine (21 ml, 0.145 mol), keeping the temperature of the reaction below 5° C. The bright yellow reaction mixture is gradually allowed to warm to RT and stirred overnight. Water (250 ml) is added to the reaction mixture with stirring. Mixture is partitioned and the aqueous phase is washed with DCM (100 ml). The organic extracts are combined, washed with NaHCO$_3$ (2×200 ml), water (2×150 ml), brine (200 ml), and concentrated in vacuo to give a pale orange solid. This is then slurried in isohexane for 30 minutes, filtered, then taken up in DCM (90 ml) with heating. The solution is then placed in the fridge over the weekend. The crystalline material formed is filtered and washed with a minimal amount of cold DCM to afford the title compound.

Intermediate M (2-Amino-benzoylamino)-acetic acid tert-butyl ester

To a stirring solution of isatoic anhydride (25 g, 0.15 mol) in DMF (250 ml), glycine tert butyl ester (30.64 g, 0.18 mol) is added, followed by the dropwise addition of triethylamine (52 ml, 0.37 mol) over a period of 30 minutes. The resulting suspension is heated at 50° C. for 3 hours, 60° C. for 30 minutes, then at 70° C. for 30 minutes. The reaction mixture is then allowed to cool to RT and treated with water (300 ml). The resulting solution is stirred at RT for 30 minutes, diluted further with water (200 ml), and the product extracted with EtOAc (2×500 ml). The organic extracts are combined, washed with water (2×300 ml), brine (1×300 ml), dried (MgSO$_4$), filtered, concentrated in vacuo, and dried under vacuum to give the title compound as a peachy white solid.

Intermediate N 2-Bromo-N-(2,6-dichloro-pyridin-4-yl)-acetamide

To a stirring solution of 4-amino-2,6-dichloro-pyridine (4.7 g, 28.8 mmol) in DCM, bromoacetyl bromide (2.56 ml, 29.4 mmol) is added. The solution is cooled to 0° C. and stirred for 5 minutes before treating dropwise with triethylamine (7.87 ml, 57.7 mmol). The reaction mixture is gradually allowed to warm to RT and stirred for 48 hours. The reaction mixture is diluted with DCM and washed with water several times. The organic extracts are dried, filtered and concentrated in vacuo. The crude product is purified using flash column chromatography on silica (DCM/Isohexane) to afford the title compound.

Intermediate P Ureido-acetic acid tert-butyl ester

To a solution of glycine tert-butyl ester hydrochloride (15.13 g, 89.5 mmol) in water (12 ml), a warm solution of potassium cyanate (8.89 g, 107.4 mmol) in water (12 ml) is added in one portion. The clear solution is heated to 65° C. to 70° C. for 15 minutes before removing from heat and cooling to 0° C. in an ice bath. MeOH (approximately 5 ml) is added to dissolve the oil formed and the mixture allowed to sit at 0° C. The crystals formed are filtered, washed with ice water (3×2 ml) and dried to give the title compound; [M+H]$^+$ 174

Intermediate Q (2,4-Dioxo-1,4-dihydro-2H-pyrido[3,2-d]pyrimidin-3-yl)-acetic acid t-butyl ester A 2-5 ml Biotage microwave vial is charged with Pd(OAc)$_2$ (2.5 mol %, 4.6 mg, 0.019 mmol), Xantphos (5 mol %, 22.3 mg, 0.038 mmol), ureido-acetic acid tert-butyl ester (223.7 mg, 1.216 mmol), and Cs$_2$CO$_3$ (736.6 mg, 1.9 mmol). Methyl 3-iodopyridine-2-carboxylate (200.4 mg, 0.76 mmol) is added, followed by 1-4-dioxane (4 ml). The vessel is sealed and treated in the microwave at 120° C. for 5400 seconds. EtOAc was added to the mixture and decanted off. LCMS of this (+ELS) indicated no product. Water added to the residue giving rise to a white solid. LCMS of this material (+ELS) showed product. Material taken up in EtOAc, washed with brine (3×20 ml), then water (2×20 ml). The organic portions are passed through Celite® and the solvent removed in vacuo to give the title compound; [M+H]$^+$ 278

Intermediate R {1-[(5-Chloro-2,4-dimethoxy-phenylcarbamoyl)-methyl]-2,4-dioxo-1,4-dihydro-2H-pyrido[3,2-d]pyrimidin-3-yl}-acetic acid tert-butyl ester A 25 ml round bottomed flask charged with (2,4-Dioxo-1,4-dihydro-2H-pyrido[3,2-d]pyrimidin-3-yl)-acetic acid t-butyl ester (14.9 mg, 0.054 mmol), 2-Bromo-N-(5-chloro-2,4-dimethoxy-phenyl)-acetamide (26.5 mg, 0.06 mmol), and Cs$_2$CO$_3$ (50.9 mg, 0.11 mmol) is treated with DMF (3 ml) and the solution stirred at RT. After 2 hours, the reaction mixture is treated with water and stirred for 10 minutes. The product is extracted into EtOAc and washed with water (3×10 ml). The organic portions are dried (MgSO$_4$), filtered and concentrated to give the title compound, [M+H]$^+$ 505

Intermediate S (5-Chloro-2,4-dioxo-1,4-dihydro-2H-pyrido[4,3-d]pyrimidin-3-yl)-acetic acid tert-butyl ester A 2-5 ml microwave vial is charged with Pd(OAc)$_2$ (2.5 mol %, 4.1 mg, 0.016 mmol), Xantphos (5 mol %, 24.9 mg, 0.0321 mmol), ureido-acetic acid tert-butyl ester (190.3 mg, 1.03 mmol), and Cs$_2$CO$_3$ (578.9 mg, 1.605 mmol). 2-Chloro-4-iodo-nicotinic acid ethyl ester (208.9 mg, 0.642 mmol) is added followed by 1,4-dioxane (4 ml). The vessel is sealed and treated in the microwave at 120° C. for 3600 seconds. EtOAc is added to the mixture, washed with brine (3×20 ml), then water (2×20 ml). The organic portions are passed through Celite® and the solvent removed in vacuo. The crude material is taken up in a minimal amount of DCM and loaded onto a 10 g Isolute™ pre packed Silica II cartridge, eluted with 100% iso-hexane to 50% EtOAc:Isohexane to afford the title compound; [M+H]$^+$ 312

Intermediate T {5-Chloro-1-[(5-chloro-2,4-dimethoxy-phenylcarbamoyl)-methyl]-2,4-dioxo-1,4-dihydro-2H-pyrido[4,3-d]pyrimidin-3-yl}-acetic acid tert-butyl ester A vial is charged with (5-Chloro-2,4-dioxo-1,4-dihydro-2H-pyrido[4,3-d]pyrimidin-3-yl)-acetic acid tert-butyl ester (53.1 mg, 0.17 mmol), 2-Bromo-N-(5-chloro-2,4-dimethoxy-phenyl)-acetamide (58.1 mg, 0.187 mmol), and Cs$_2$CO$_3$ (124.3 mg, 0.34 mmol). The mixture is treated with DMF (3 ml) and the solution stirred at RT overnight. The reaction mixture is treated with water and the product extracted with EtOAc (3×10 ml). The organic extracts are combined and washed with water (2×10 ml), dried (MgSO$_4$), filtered and concentrated in vacuo. The crude material is purified using flash column chromatography with an eluent system of isohexane:EtOAc to give the title compound; [M+H]$^+$ 539.

Intermediate U (2,4-Dioxo-1,4-dihydro-2H-pyrido[3,4-d]pyrimidin-3-yl)-acetic acid tert-butyl ester A 2-5 ml microwave vial is charged with Pd(OAc)$_2$ (2.5 mol %, 6.6 mg, 0.0231 mmol), Xantphos (5 mol %, 27.1 mg, 0.0463 mmol), ureido-acetic acid tert-butyl ester (259 mg, 1.482 mmol), and Cs$_2$CO$_3$ (770.2 mg, 2.315 mmol). 3-Bromo-isonicotinic acid methyl ester (216.3 mg, 0.926 mmol) is added, followed by 1,4-dioxane (4 ml). The vessel is sealed and treated in the microwave at 120° C. for 3×3600 seconds. EtOAc is added to the reaction mixture which is then washed with brine (3×20 ml) and water (2×10 ml). The organic phase is passed through Celite® (filter material), dried (MgSO$_4$), filtered and concentrated. The material is purified via flash column chromatography, eluting with iso-hexane:EtOAc to afford the title compound; [M+H]$^+$ 278.

Intermediate V {1-[(5-Chloro-2,4-dimethoxy-phenylcarbamoyl)-methyl]-2,4-dioxo-1,4-dihydro-2H-pyrido[3,4-d]pyrimidin-3-yl}-acetic acid tert-butyl ester A 25 ml round bottomed flask is charged with (2,4-dioxo-1,4-dihydro-2H-pyrido[3,4-d]pyrimidin-3-yl)-acetic acid tert-butyl ester (23.9 mg, 0.086 mmol), 2-bromo-N-(5-chloro-2,4-dimethoxy-phenyl)-acetamide (30.5 mg, 0.095 mmol) and Cs$_2$CO$_3$ (84.6 mg, 0.172 mmol). The mixture is treated with DMF (2 ml) and the solution stirred at RT overnight. Water is added to the mixture giving rise to a solid. This is filtered, dried, and purified via flash column chromatography, eluting with iso-hexane:EtOAc to give the title compound.

The invention claimed is:
1. A compound of formula (I):

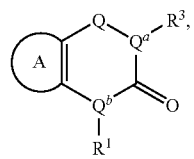

or a pharmaceutically acceptable salt thereof, wherein

Q is selected from $CH_2$, and $C(O)$;

is selected from $C_6$-$C_{15}$-aromatic carbocyclic group, a $C_5$-$C_{15}$-carbocyclic group, and a 4- to 15-membered heterocyclic group having one or more heteroatoms selected from the group consisting of oxygen, nitrogen and sulphur;

$R^1$ is selected from —$C(R^{1a}R^{1b})_mC(O)NR^{1c}R^{1d}$, —$C(R^{1a}R^{1b})_mC(O)CR^{1c}R^{1d}R^{1e}$, —$C(R^{1a}R^{1b})_nNR^{1c}R^{1d}$, $C(R^{1a}R^{1b})_mCR^{1c}R^{1d}R^{1c}$, and $C(R^{1a}R^{1b})_mSO_2R^{1f}$;

$R^{1a}$ and $R^{1b}$ are independently selected from H, —OH, and $C_1$-$C_8$-alkyl optionally substituted by —OH and halogen;

$R^{1c}$ is selected from H;

$C_6$-$C_{15}$-aromatic carbocyclic group, $C_7$-$C_{15}$-aralkyl, $C_3$-$C_{15}$-carbocyclic group, a 4- to 15-membered heterocyclic group having one or more heteroatoms selected from the group consisting of oxygen, nitrogen and sulphur;

$C_1$-$C_8$-alkoxy optionally substituted by OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$C_2$-$C_8$-alkenyl optionally substituted by —OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$C_2$-$C_8$-alkynyl optionally substituted by —OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur; and $C_1$-$C_8$-alkyl optionally substituted by —OH, —CN, halogen, $NR^4R^5$, $C_1$-$C_8$-alkoxycarbonyl, COOH, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$R^{1d}$ and $R^{1e}$ are H;

$R^{1f}$ is selected from $C_6$-$C_{15}$-aromatic carbocyclic group, a $C_3$-$C_{15}$-carbocyclic group, $C_1$-$C_8$-haloalkyl and a 4- to 10-membered heterocyclic group having one or more heteroatoms selected from the group consisting of oxygen, nitrogen and sulphur;

$R^3$ is selected from $C_6$-$C_{15}$-aromatic carbocyclic group optionally substituted by —$C(R^{3a}R^{3b})_nC(O)NR^{3c}R^{3d}$ or —$C(R^{3a}R^{3b})_nC(O)OH$, $C_3$-$C_{15}$-carbocyclic group, $C_{1-8}$-alkylaminocarbonyl, —$C(R^{3a}R^{3b})_nC(O)NR^{3c}R^{3d}$ and —$C(R^{3a}R^{3b})C(O)OH$;

$R^{3a}$ and $R^{3b}$ are independently selected from H, —OH, and $C_1$-$C_8$-alkyl optionally substituted by —OH, halogen;

$R^{3c}$ and $R^{3d}$ are independently selected from H;

$C_6$-$C_{15}$-aromatic carbocyclic group, $C_3$-$C_{15}$-carbocyclic group;

a 4- to 15-membered heterocyclic group having one or more heteroatoms selected from the group consisting of oxygen, nitrogen and sulphur, and $C_1$-$C_8$-alkyl optionally substituted by —OH, —CN, halogen, $NR^4R^5$, a $C_6$-$C_{15}$-aromatic carbocyclic group, $C_3$-$C_{15}$-carbocyclic group and a 4- to 15-membered heterocyclic group having one or more heteroatoms selected from the group consisting of oxygen, nitrogen and sulphur;

$R^4$ and $R^5$ are independently selected from H and $C_1$-$C_8$-alkyl;

m and n are independently selected from an integer of 0, 1 and 2; and t is an integer selected from 1 and 2;

wherein said $C_6$-$C_{15}$-aromatic carbocyclic group, $C_7$-$C_{15}$-aralkyl, $C_3$-$C_{15}$-carbocyclic group and 4- to 15-membered heterocyclic group having one or more heteroatoms selected from the group consisting of oxygen, nitrogen and sulphur, unless otherwise stated, are each optionally substituted by $C_7$-$C_{15}$-aralkyl, $C_1$-$C_8$-alkyl, CN, $C_1$-$C_8$-alkylsulfonyl, $C_1$-$C_8$-haloalkylsulfonyl, halogen, $C_1$-$C_8$-alkoxy, OH, $C_1$-$C_8$-alkylcarbonyl, —$C(O)$—$C_6$-$C_{15}$-aromatic carbocyclic group, —$C(O)$—$C_3$-$C_{15}$-carbocyclic group, —$C(O)$-4- to 15-membered heterocyclic group having one or more heteroatoms selected from the group consisting of oxygen, nitrogen and sulphur, $C_1$-$C_8$-cyanoalkyl, $C_1$-$C_8$-cyanoalkoxy, $C_1$-$C_8$-haloalkyl, $C_1$-$C_8$-haloalkoxy, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, COOH, $C_1$-$C_8$-alkoxycarbonyl, 4- to 15-membered heterocyclic group having one or more heteroatoms selected from the group consisting of oxygen, nitrogen and sulphur optionally substituted by $C_7$-$C_{15}$-aralkyl, $C_1$-$C_8$-alkyl, CN, $C_1$-$C_8$-alkylsulfonyl, $C_1$-$C_8$-haloalkylsulfonyl, halogen, $C_1$-$C_8$-alkoxy, OH, $C_1$-$C_8$-alkylcarbonyl, $C_1$-$C_8$-Cyanoalkyl, $C_1$-$C_8$-Cyanoalkoxy, $C_1$-$C_8$-haloalkyl, $C_1$-$C_8$-haloalkoxy, $C_1$-$C_8$-alkylaminocarbonyl, di($C_1$-$C_8$-alkyl)aminocarbonyl, $C_1$-$C_8$-alkylamino, di($C_1$-$C_8$-alkyl) amino COOH, or $C_1$-$C_8$-alkoxycarbony, a $C_6$-$C_{15}$-aromatic carbocyclic group optionally substituted by $C_7$-$C_{15}$-aralkyl, $C_1$-$C_8$-alkyl, CN, halogen, $C_1$-$C_8$-alkoxy, OH, $C_1$-$C_8$-alkylcarbonyl, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, COOH, $CF_3$, or $C_1$-$C_8$-alkoxycarbonyl or a $C_3$-$C_{15}$-carbocyclic group optionally substituted by $C_7$-$C_{15}$-aralkyl, $C_1$-$C_8$-alkyl, CN, halogen, $C_1$-$C_8$-alkoxy, OH, $C_1$-$C_8$-alkylcarbonyl, $C_1$-$C_8$-alkylaminocarbonyl, di($C_1$-$C_8$-alkyl)aminocarbonyl, $C_1$-$C_8$-alkylamino, di($C_1$-$C_8$-alkyl)amino, COOH, $CF_3$, or $C_1$-$C_8$-alkoxycarbonyl;

with the proviso that said compound of formula (I) is not 3-{1-[(5-chloro-2-methoxy-phenylcarbamoyl)-methyl]-2,4-dioxo-1,4-dihydro-2H-quinazolin-3-yl}-N-cyclopentyl-propionamide, N-(5-chloro-2,4-dimethoxy-phenyl)-2-[2,4-dioxo-3 {[(tetrahydro-furan-2-ylmethyl)-carbamoyl]-methyl}-phenyl)-3,4-dihydro-2H-quinazolin-1-yl] acetamide, 4-{6-chloro-1-[2-(3-chloro-4-ethoxy-phenyl)-2-oxoethyl]-2,4-dioxo-1,4-dihydro-2H-quinazolin-3-yl}-N-cyclopentyl-butyramide, 2-{1-[(5-chloro-2,4-dimethoxy-phenylcarbamoyl)-methyl]-2,4-dioxo-1,4-dihydro-2H-quinazolin-3-yl}-N-furan-2-ylmethyl-acetamide, 4-(2-{2,4-dioxo-3-[4-(phenethylcarbamoyl-methyl)-phenyl]-3,4-dihydro-2H-quinazolin-1-yl}-acetylamino)-benzoic acid ethyl ester, N-(3,5-dichloro-phenyl)-2-{2,4-dioxo-3-[4-(phenethylcarbamoyl-methyl)-phenyl]-3,4-dihydro-2H-quinazolin-1-yl}-acetamide, 2-{1-[(4-chloro-2-methoxy-5-methyl-phenylcarbamoyl)-methyl]-2,4-dioxo-1,4-dihydro-2H-quinazolin-3-yl}-N-cyclopentyl-acetamide, 2-{1-[(5-chloro-2,4-dimethoxy-phenylcarbamoyl)-methyl]-2,4-dioxo-1,4-dihydro-2H-quinazolin-3-yl}-N-phenethyl-acetamide and 1-[(5-chloro-2,4-dimethoxyphenylcarbamoyl)-methyl]-2,4-dioxo-3-phenyl-1,3,4,5,6,8-hexahydro-2H-pyrido[4',3':4,5]thieno[2,d]pyrimidine-7-carboxylic acid ethyl ester.

2. A compound according to claim 1, where said compound is of formula (Ia):

(Ia)

where
- $R^1$ is $-C(R^{1a}R^{1b})_mC(O)NR^{1c}R^{1d}$, where $R^{1a}R^{1b}$ and $R^{1c}$ are H;
- $R^{1d}$ is a $C_6$-$C_{15}$-aromatic carbocyclic group or a 4- to 15-membered heterocyclic group having one or more heteroatoms selected from the group consisting of oxygen, nitrogen and sulphur, $-C(R^{1a}R^{1b})_tNR^{1c}R^{1d}$ where $R^{1a}$ and $R^{1c}$ are H;
- t is 1;
- or $R^{1d}$ is a $C_1$-$C_8$-alkyl substituted by a $C_6$-$C_{15}$-aromatic carbocyclic group; and

A is selected from:

where
- $R^7$ is selected from H and $C_1$-$C_8$-alkoxycarbonyl;
- each $R^8$ is selected from H, halo, CN, $CO_2H$, $CH_2NH_2$ and $C_1$-$C_8$-alkyl;
- p is an integer selected of 1 to 3; and
- q is an integer selected from 1 to 4;

or a pharmaceutically acceptable salt thereof.

3. The compound of claim 2, wherein $R^{1d}$ is a 4- to 15-membered heterocyclic group selected from pyridine, pyrazine, piperidine and benzothiazole.

4. The compound of claim 3, wherein substituents for the heterocyclic group are selected from $C_1$-$C_8$ alkyl, OH, and halogen.

5. The compound of claim 2, wherein $R^3$ is $-C(R^{3a}R^{3b})_nC(O)NR^{3c}R^{3d}$.

6. The compound of claim 2, wherein

A is phenyl.

7. A pharmaceutical composition comprising the compound of claim 1 and at least one pharmaceutically acceptable diluent or carrier.

8. The pharmaceutical composition of claim 7, further comprising a co-therapeutic agent that is an anti-inflammatory, broncho-dilatory, antihistamine, or antitussive drug.

* * * * *